US012753148B2

(12) United States Patent
Kelly et al.

(10) Patent No.: US 12,753,148 B2
(45) **Date of Patent: *Oct. 6, 2026**

(54) SOLID FORMS, SALTS AND POLYMORPHS OF ANTI-FIBROTIC COMPOUNDS

(71) Applicant: Certa Therapeutics Pty Ltd, Melbourne (AU)

(72) Inventors: Darren James Kelly, Melbourne (AU); Gareth Rhys Lewis, Melbourne (AU); Lorna Helen Mitchell, Auckland (NZ)

(73) Assignee: Certa Therapeutics Pty Ltd, Melbourne (AU)

( * ) Notice: Subject to any disclaimer, the term of this patent is extended or adjusted under 35 U.S.C. 154(b) by 291 days.

This patent is subject to a terminal disclaimer.

(21) Appl. No.: 18/537,184

(22) Filed: Dec. 12, 2023

(65) Prior Publication Data

US 2024/0262785 A1 Aug. 8, 2024

Related U.S. Application Data

(63) Continuation of application No. 18/354,467, filed on Jul. 18, 2023, now Pat. No. 11,905,231.

(30) Foreign Application Priority Data

Jan. 31, 2023 (AU) ................................ 2023900229

(51) Int. Cl.
*C07C 229/66* (2006.01)

(52) U.S. Cl.
CPC ........ *C07C 229/66* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 8,765,812 | B2 | 7/2014 | Williams et al. |
| 9,561,201 | B2 | 2/2017 | Williams et al. |

FOREIGN PATENT DOCUMENTS

| | | | |
|---|---|---|---|
| WO | 2008/003141 | A1 | 1/2008 |
| WO | WO 2008113095 | A1 | 9/2008 |
| WO | 2008/131481 | A1 | 11/2008 |
| WO | 2012/068612 | A1 | 5/2012 |

OTHER PUBLICATIONS

Gilbert et al., “A Purpose-Synthesised Anti-Fibrotic Agent Attenuates Experimental Kidney Diseases in the Rat”, vol. 7, Oct. 10, 2012 (Year: 2012).

International Search Report for International Application No. PCT/AU2023/051332, dated Feb. 2, 2024 (five pages).

Written Opinion of the International Searching Authority for International Application No. PCT/AU2023/051332, dated Feb. 2, 2024 (eight pages).

Balbach, S. and Korn, C., “Pharmaceutical evaluation of early development candidates ‘the 100 mg-approach,’” International Journal of Pharmaceutics, 275, pp. 1-12 (2004).

Deliyanti, D., et al., “FT011, a Novel Cardiorenal Protective Drug, Reduces Inflammation, Gliosis and Vascular Injury in Rats with Diabetic Retinopathy,” PLoS ONE 10(7): e0134392 (2015) (sixteen pages).

Singhal, D. and Curatolo, W., “Drug polymorphism and dosage form design: a practical perspective,” Advanced Drug Delivery Reviews, 56, pp. 335-347 (2004).

Li, X., et al., “Drugs and Targets in Fibrosis,” Frontiers in Pharmacology, 8:855, pp. 1-21.

Zammit, S., et al., “Evaluation and optimization of antifibrotic activity of cinnamoyl anthranilates,” Bioorganic & Medicinal Chemistry Letters, 19, pp. 7003-7006 (2009).

*Primary Examiner* — Adam C Milligan
*Assistant Examiner* — Jed A Kucharczk
(74) *Attorney, Agent, or Firm* — Finnegan, Henderson, Farabow, Garrett & Dunner, LLP

(57) ABSTRACT

The present disclosure relates to solid forms and salts, crystalline and otherwise, of (E)-2-[[3-(3-methoxy-4-propargyloxy)phenyl)-1-oxo-2-propenyl]amino]benzoic acid and pharmaceutical compositions comprising same. The use of such solid forms, salts, and pharmaceutical compositions, for treating, preventing, or ameliorating diseases or conditions associated with fibrosis, inflammation and/or proliferation are disclosed.

30 Claims, 19 Drawing Sheets

A

B

SOLID FORMS, SALTS AND POLYMORPHS OF ANTI-FIBROTIC COMPOUNDS

CROSS REFERENCE TO RELATED APPLICATION

This application is a continuation of U.S. application Ser. No. 18/354,467, filed Jul. 18, 2023, which claims the benefit of Australian Provisional Application No. 2023900229, filed Jan. 31, 2023; the disclosures of each of which are incorporated herein by reference in their entirety.

TECHNICAL FIELD

The present disclosure relates to solid forms and salts of (E)-2-[[3-(3-methoxy-4-propargyloxy)phenyl)-1-oxo-2-propenyl]amino]benzoic acid (FT011) in amorphous and crystalline forms, processes of preparation thereof, and pharmaceutical compositions thereof. The present disclosure also relates to methods of using such solid forms and salts and their pharmaceutical compositions for treating, preventing, or ameliorating diseases or conditions associated with fibrosis, inflammation and/or proliferation.

BACKGROUND

Fibrosis is an abnormal accumulation of a collagen matrix following injury or inflammation which alters the structure and function of various tissues. Irrespective of location, the major pathology of fibrosis involves an excessive deposition of a collagen matrix which replaces the normal tissue at that site. Progressive fibrosis in the kidney, liver, lung, heart, bone or bone marrow, and skin is a major cause of death and suffering. While the etiology and causative mechanisms of individual fibrotic disorders may vary (e.g., ischemic event, exposure to a chemical, radiation, or infectious agent) and are poorly understood, they all share the common feature of abnormal and excessive deposition of extracellular matrix in affected tissues (Wynn and Ramalingam, Nat. Med. 2012, 18:1028). Fibrosis presents a serious and unmet clinical need responsible for 45 percent (45%) of all deaths globally in the industrialised world.

Chronic heart failure (CHF) is a growing public health problem in industrialized nations. It is well recognized that the causes of CHF are multifactorial. The most common risk factors include coronary heart disease (especially previous myocardial infarction), long-term high blood pressure, diabetes, and idiopathic cardiomyopathy. However, the impending epidemic of obesity and diabetes, coupled with an ageing population and improved survival from heart attack, warn of a significant increase in the number of people with HF due to diabetes and related disorders as well as the subsequent future economic health burden (Najafi et al., Eur J Heart Fail 2009; 11:472).

Individuals with diabetes mellitus are at high risk of developing CHF. Even in the absence of other co-morbid conditions such as atherosclerosis or hypertension, diabetes alone still manifests as primary myocardial disease termed diabetic cardiomyopathy (DCM), with data from the Framingham heart study indicating that diabetes results in a 4- to 5-fold increased risk of developing HF. Diabetic cardiomyopathy in humans is characterized in its early stages by abnormal diastolic function along with subtle changes in systolic function such as reduced longitudinal fibre contractility. Pathologically, DCM is associated with microvascular disease and shares important similarities with diabetic nephropathy. Examination of left ventricular (LV)

biopsies from patients with diabetes shows that, at the cellular level, DCM is associated with myocyte hypertrophy, necrosis, apoptosis, fibroblast proliferation, and, importantly, increased deposition of fibrillar collagen (fibrosis) in the interstitial regions. Elevated levels of cardiac fibrosis in these patients correlate with cardiac dysfunction including increased end-diastolic pressure (EDP), end-diastolic pressure-volume relationship (EDPVR), and end-diastolic volume (EDV), and reduced ejection fraction (EF). Thus, pathological fibrosis impacts greatly on ventricular compliance, resulting in impaired diastolic function due to increase myocardial stiffness.

Pathological fibrosis underlying cardiac remodelling in diabetes is probably mediated by locally active cytokines such as tumour necrosis factor-α (TNF-α), nuclear factor κ-light-chain-enhancer of activated B cells (NF-κB), and transforming growth factor-β (TGF-β).

Current treatment of CHF (including diabetic HF) includes good glycaemic control and treatment with beta-blockers, angiotensin-converting enzyme inhibitors, angiotensin receptor antagonists, and mineralocorticoid receptor blockade, all of which have been shown to reduce overall mortality and improve clinical symptoms. However, despite such therapy, cardiac dysfunction continues to progress in the majority of patients.

The rising epidemic of diabetes and the clear indication that pathological fibrosis underlies the decline in diastolic function in CHF in diabetes indicate the need for additional therapies for the treatment of DCM. Current therapies do not directly target the pro-inflammatory and pro-fibrotic processes that occur in the heart in diabetes.

Chronic kidney disease (CKD) is a major cause of morbidity, recurrent hospitalisation and accelerated death, affecting 10-11% of the population in both Europe and the United States (Hallan et al., J Am Soc Nephrol. 2006, 17: 2275). In a substantial proportion of such patients, deteriorating kidney function leads to the development of end-stage kidney disease (ESKD), requiring dialysis or transplantation to preserve life. Studies conducted almost 20 years ago highlighted the importance of blood pressure control and blockade of the renin-angiotensin system in attenuating the progression of CKD towards its end stage. Unfortunately, while substantial progress has been made in our understanding of renal pathophysiology, there has been little in the way of new therapies since that time.

Possessing only a limited capacity for regeneration, sustained or repeated injury to the kidney leads to the deposition of excessive quantities of extracellular matrix in both the glomerulus and tubulointerstitium. These expansive pathological changes, recognised histologically as glomerulosclerosis and tubulointerstitial fibrosis, encroach on surrounding structures inevitably leading to capillary rarefaction with consequent hypoxia, tubular atrophy and inflammatory cell infiltration. These structural changes, in turn, result in a loss of GFR that is frequently, though not invariably, accompanied by worsening proteinuria. This final common pathway, occurring in most forms of chronic kidney disease, ensues almost regardless of primary aetiology, developing in response to seemingly diverse disorders that include metabolic, immunological and infectious causes.

Studies conducted over more than a decade have consistently indicated a major role for the prosclerotic growth factor, transforming growth factor-β (TGF-β) in renal fibrosis and dysfunction. However, other locally-active growth factors have also been implicated in the fibrogenic process, particularly platelet-derived growth factor (PDGF), a potent inducer of matrix synthesis and the proliferation of fibrogenic mesenchymal cells such as fibroblasts and mesangial cells. Consistent with these actions, kidney tissue from a range of human and experimental kidney diseases demonstrates increased expression in the components of both the TGF-β and PDGF pathways, such that each has become an important therapeutic targets in an attempt to develop new therapies for chronic kidney disease.

There continues to be a need for new therapies to ameliorate, treat and/or prevent diseases or conditions associated with fibrosis, inflammation and/or proliferation, such as fibrosis of the diabetic heart, chronic kidney disease, or cancer.

SUMMARY

The present disclosure relates, in part, to solid forms and pharmaceutically acceptable salts of (E)-2-[[3-(3-methoxy-4-propargyloxy)phenyl)-1-oxo-2-propenyl]amino]benzoic acid, including crystalline forms thereof. In some embodiments, the pharmaceutically acceptable salt of (E)-2-[[3-(3-methoxy-4-propargyloxy)phenyl)-1-oxo-2-propenyl]amino]benzoic acid is selected from the group consisting of a salt, potassium salt, a meglumine an ethanolamine salt, a tris(hydroxymethyl)aminomethane salt, a tert-butylamine salt, an ammonium salt, and a lysine salt of (E)-2-[[3-(3-methoxy-4-propargyloxy)phenyl)-1-oxo-2-propenyl]amino]benzoic acid. In some embodiments, the pharmaceutically acceptable salt of (E)-2-[[3-(3-methoxy-4-propargyloxy)phenyl)-1-oxo-2-propenyl]amino]benzoic acid is an ethanolamine salt or a tert-butylamine salt of (E)-2-[[3-(3-methoxy-4-propargyloxy)phenyl)-1-oxo-2-propenyl]amino]benzoic acid. In certain embodiments, the pharmaceutically acceptable salt of (E)-2-[[3-(3-methoxy-4-propargyloxy)phenyl)-1-oxo-2-propenyl]amino]benzoic acid is an ethanolamine salt of (E)-2-[[3-(3-methoxy-4-propargyloxy)phenyl)-1-oxo-2-propenyl]amino]benzoic acid (also referred to herein as ethanolammonium (E)-2-[[3-(3-Methoxy-4-propargyloxy)phenyl)-1-oxo-2-propenyl]amino]benzoate).

The novel salts described herein of the anti-fibrotic, anti-inflammatory compound (E)-2-[[3-(3-methoxy-4-propargyloxy)phenyl)-1-oxo-2-propenyl]amino]benzoic acid, such as the ethanolamine and tert-butylamine salts of (E)-2-[[3-(3-methoxy-4-propargyloxy)phenyl)-1-oxo-2-propenyl]amino]benzoic acid, are solids with excellent chemical and physical properties such as high thermal stability and low hygroscopicity, and possess superior pharmacokinetic properties such as high bioavailability. Accordingly, they are particularly valuable as therapeutic agents for the treatment, prevention, or amelioration of fibrotic, inflammatory or proliferative diseases or conditions, and are particularly adapted for use in various pharmaceutical dosage forms, including those designed for oral, topical or parenteral administration.

The compound (E)-2-[[3-(3-Methoxy-4-propargyloxy)phenyl)-1-oxo-2-propenyl]amino]benzoic acid has the structure of Formula (I):

Formula (I)

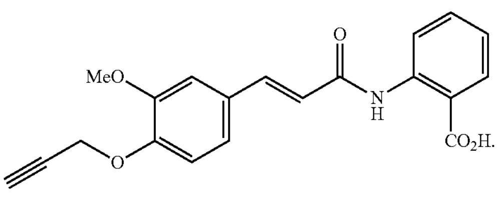

Accordingly, in one aspect of the present disclosure, there is provided a crystalline form of a pharmaceutically acceptable salt of the compound of Formula (I):

Formula (I)

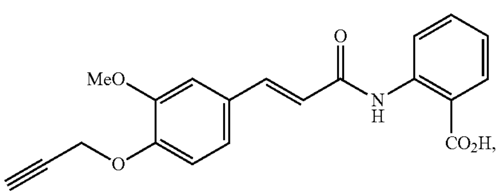

wherein the crystalline form has a water sorption of less than 1.7% at 25° C. and 80% relative humidity as determined by dynamic vapor sorption.

In embodiments, the crystalline form has a weight loss of from 0.07% to 8.94% when heated from 25° C. to 120° C. as determined by thermogravimetric analysis.

In embodiments, the crystalline form has a weight loss of from 0.07% to 8.94%, or from 0.07% to 0.94% when heated from 25° C. to 120° C. as determined by thermogravimetric analysis.

In embodiments, the crystalline form has one or more of the following properties:

a solubility of from 2.5 mg/ml to greater than 5.0 mg/ml at 24 hours in FaSSIF media (pH 7.5);

a solubility of from 3.4 mg/ml to greater than 5.0 mg/ml at 24 hours in FeSSIF media (pH 7.8);

a solubility of from 0.07 mg/ml to 0.090 mg/ml at 24 hours in media at pH 6.8.

In embodiments, the crystalline form has bioavailability of from 39 F % to 82 F %, from 50 F % to 82 F %, or from 64 F % to 82 F %.

In embodiments, the pharmaceutically acceptable salt is selected from the group consisting of: a meglumine salt, an ethanolamine salt, a tris(hydroxymethyl)aminomethane salt, and a tert-butylamine salt.

In embodiments, a pharmaceutical composition comprises a crystalline form disclosed herein and a pharmaceutically acceptable carrier. In embodiments, said pharmaceutical composition is suitable for oral administration.

There is also provided a crystalline form of an ethanolamine salt of the compound of Formula (I):

Formula (I)

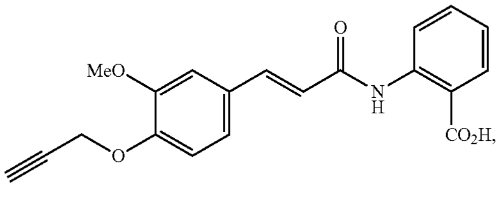

wherein the crystalline form has a bioavailability of at least about 1.5× compared to bioavailability of the free form of the compound of Formula (I).

In embodiments, the crystalline form has a bioavailability of at least about 1.8×, at least about 2.0×, or at least about 2.3× compared to bioavailability of the free form of the compound of Formula (I).

In embodiments, the crystalline form has a bioavailability of about 82 F %.

In embodiments, the crystalline form has a water sorption of 0.49% at 25° C. and 80% relative humidity as determined by dynamic vapor sorption.

In embodiments, the crystalline form has an endothermic onset of 176° C. as measured by differential scanning calorimetry.

In embodiments, the crystalline form has a melting point of 178° C. as measured by differential scanning calorimetry.

In embodiments, the crystalline form has a weight loss of 0.10% when heated from 25° C. to 120° C. as determined by thermogravimetric analysis.

In embodiments, the crystalline form has one or more of the following properties:

a solubility of greater than 7.99 mg/ml at 24 hours in FaSSIF media (pH 7.5);

a solubility of greater than 8.02 mg/ml at 24 hours in FeSSIF media (pH 7.8);

a solubility of 0.088 mg/ml at 24 hours in media at pH 6.8.

In embodiments, a pharmaceutical composition comprises a crystalline form disclosed herein and a pharmaceutically acceptable carrier. In embodiments, said pharmaceutical composition is for oral administration.

There is also provided a crystalline form of an ethanolamine salt of the compound of Formula (I):

Formula (I)

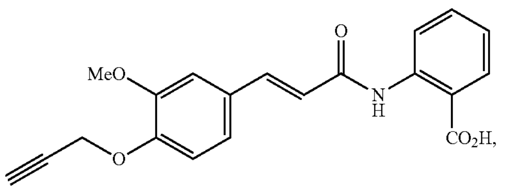

wherein the crystalline form exhibits an X-ray powder diffraction pattern having at least one peak selected from 6.6±0.2, 11.7±0.2, 15.0±0.2, 15.9±0.2, 17.7±0.2, 18.7±0.2, 19.2±0.2, 23.7±0.2, and 26.6±0.2 degrees 2θ.

In embodiments, the crystalline form exhibits an X-ray powder diffraction pattern having at least two, at least three, at least four, or at least five peaks selected from 6.6±0.2, 11.7±0.2, 15.0±0.2, 15.9±0.2, 17.7±0.2, 18.7±0.2, 19.2±0.2, 23.7±0.2, and 26.6±0.2 degrees 2θ.

In embodiments, the crystalline form exhibits an X-ray powder diffraction pattern having at least one peak selected from 6.6±0.2, 11.7±0.2, 15.0±0.2, 15.9±0.2, 17.7±0.2, 18.7±0.2 and 19.2±0.2 degrees 2θ.

In embodiments, the crystalline form exhibits an X-ray powder diffraction pattern having at least one peak selected from 6.6±0.2, 15.0±0.2, 18.7±0.2 and 19.2±0.2 degrees 2θ.

In embodiments, the crystalline form exhibits an X-ray powder diffraction pattern having at least two peaks selected from 6.6±0.2, 15.0±0.2, 18.7±0.2 and 19.2±0.2 degrees 2θ.

In embodiments, the crystalline form exhibits an X-ray powder diffraction pattern having at least three peaks selected from 6.6±0.2, 15.0±0.2, 18.7±0.2 and 19.2±0.2 degrees 2θ.

In embodiments, the crystalline form exhibits an X-ray powder diffraction pattern having peaks at 6.6±0.2, 15.0±0.2, 18.7±0.2 and 19.2±0.2 degrees 2θ.

In embodiments, the crystalline form exhibits a single X-ray crystallographic analysis with the following parameters:

| Parameter | Value |
|---|---|
| Molecular formula | $C_{20}H_{16}NO_5 \bullet C_2H_8NO$ |
| Formula weight | 412.43 |
| space group | $P2_1/c$ (No. 14) |
| a, Å | 4.7710 ± (8) |
| b, Å | 29.645 ± (4) |
| c, Å | 14.223 ± (2) |
| α, deg | 90 |
| ß, deg | 90.120 ± (11) |
| γ, deg | 90 |
| V, $Å^3$ | 2011.6 (5) |
| Z | 4 |
| temperature, K | 170 |
| radiation (wavelength, Å) | Cu Kα (1.54178) |

In embodiments, a crystalline form of an ethanolamine salt of the compound of Formula (I):

Formula (I)

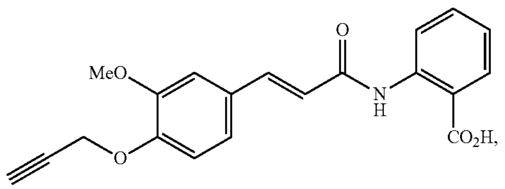

exhibits a single X-ray crystallographic analysis with the following parameters:

| Parameter | Value |
|---|---|
| Molecular formula | $C_{20}H_{16}NO_5 \bullet C_2H_8NO$ |
| Formula weight | 412.43 |
| space group | $P2_1/c$ (No. 14) |
| a, Å | 4.7710 ± (8) |
| b, Å | 29.645 ± (4) |
| c, Å | 14.223 ± (2) |
| α, deg | 90 |
| ß, deg | 90.120 ± (11) |
| γ, deg | 90 |
| V, $Å^3$ | 2011.6 (5) |
| Z | 4 |
| temperature, K | 170 |
| radiation (wavelength, Å) | Cu Kα (1.54178) |

In embodiments, the crystalline form has an endothermic onset of 176° C. as measured by differential scanning calorimetry.

In embodiments, a pharmaceutical composition comprises a crystalline form disclosed herein and a pharmaceutically acceptable carrier. In embodiments, said pharmaceutical composition is for oral administration.

There is also provided a pharmaceutical composition comprising a crystalline form disclosed herein, and a pharmaceutically acceptable excipient.

In embodiments, the pharmaceutical composition is formulated for single dose administration.

In embodiments, the pharmaceutical composition is formulated as an oral, parenteral, or intravenous dosage form. In some embodiments, the pharmaceutical composition is formulated as an oral dosage form. In some embodiments, the oral dosage form is a tablet or capsule.

In embodiments, the pharmaceutical composition comprises from about 1 to about 2000 mg of a crystalline form disclosed herein. In embodiments, the pharmaceutical composition comprises about 50, about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 mg of a crystalline form disclosed herein. In embodiments, the pharmaceutical composition comprises about 20, about 30, about 40, about 50, about 100, about 150, about 200, about 250, about 300, about 350, or about 400 mg of a crystalline form disclosed herein. In embodiments, the pharmaceutical composition comprises about 1, about 2, about 3, about 4, about 5, about 6, about 7, about 8, about 9, about 10, about 11, about 12, about 13, about 14, about 15, about 16, about 17, about 18, about 19, or about 20 mg of a crystalline form disclosed herein.

In embodiments, the pharmaceutical composition comprises a crystalline form disclosed herein in an amount effective to provide a dose of from about 1 mg/kg to about 500 mg/kg of the compound of Formula (I). In embodiments, the pharmaceutical composition comprises a crystalline form disclosed herein in an amount effective to provide a dose of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, or about 400 mg/kg of the compound of Formula (I). In embodiments, the pharmaceutical composition comprises a crystalline form disclosed herein in an amount effective to provide a dose of between about 10 and about 400 mg/kg, or between about 50 and about 300 mg/kg, or between about 100 and about 250 mg/kg of the compound of Formula (I). In embodiments, the pharmaceutical composition comprises a crystalline form disclosed herein in an amount effective to provide a dose of about 200 mg/kg of the compound of Formula (I).

In embodiments, the pharmaceutical composition comprises a crystalline form disclosed herein in an amount effective to provide a concentration of from 10 UM to 200 μM, or from 10 μM to 100 μM, or from 10 μM to 50 μM of the compound of Formula (I) at a site of its action. In embodiments, the pharmaceutical composition comprises a crystalline form disclosed herein in an amount effective to provide a concentration of about 20 to about 40 μM, about 25 to about 35 μM, or about 30 μM of the compound of Formula (I) at a site of its action.

There is also provided a method of treating, preventing, or ameliorating a fibrotic, inflammatory or proliferative disease or condition in a subject, comprising administering to the subject a therapeutically effective amount of a crystalline form as defined herein, or a pharmaceutical composition as defined herein.

In embodiments, the fibrotic, inflammatory or proliferative disease or condition is selected from fibrosis of skin, lung, heart, kidney, pancreas, eye and liver.

In embodiments, the fibrotic, inflammatory or proliferative disease or condition is selected from diabetic cardiomyopathy, congestive heart failure, ischemic heart disease, hypertension, peripheral artery disease, cerebrovascular disease, kidney disease, systemic sclerosis (scleroderma), hypertrophic scars, keloids, pulmonary fibrosis, non-alcoholic steatohepatitis (NASH), non-alcoholic fatty liver disease (NAFLD), primary biliary cirrhosis (PBC), and primary sclerosis cholangitis (PSC).

In embodiments, the fibrotic, inflammatory or proliferative disease or condition is a kidney disease.

In embodiments, the fibrotic, inflammatory or proliferative disease or condition is selected from chronic kidney disease, progressive kidney disease, diabetic nephropathy, diabetic kidney disease, glomerulonephritis, focal segmental glomerulosclerosis, systemic lupus, lupus nephritis, primary glomerulonephritis, membranous nephropathy, membranoproliferative glomerulonephritis, diffuse proliferative glomerulonephritis, membranous focal segmental glomerulosclerosis, secondary glomerulonephritis, membranous nephropathy, IgA nephropathy, or ischemic nephropathy.

In embodiments, the fibrotic, inflammatory or proliferative disease or condition is chronic kidney disease.

In embodiments, the fibrotic, inflammatory or proliferative disease or condition is diabetic nephropathy.

In embodiments, the fibrotic, inflammatory or proliferative disease or condition is focal segmental glomerulosclerosis.

In embodiments, the fibrotic, inflammatory or proliferative disease or condition is diabetic cardiomyopathy, congestive heart failure, or ischemic heart disease.

In embodiments, the fibrotic, inflammatory or proliferative disease or condition is systemic sclerosis or Scleroderma.

In embodiments, the fibrotic, inflammatory or proliferative disease or condition is pulmonary fibrosis. In embodiments, the pulmonary fibrosis is idiopathic pulmonary fibrosis (IPF).

In embodiments, the fibrotic, inflammatory or proliferative disease or condition is selected from chronic obstructive pulmonary disorder (COPD), asthma, and cystic fibrosis.

In embodiments, the fibrotic, inflammatory or proliferative disease or condition is a fibrotic eye disease. In embodiments, the fibrotic eye disease is selected from diabetic retinopathy, wet age related macular degeneration, and diabetic macular edema.

In embodiments, the fibrotic, inflammatory or proliferative disease or condition is a cancer. In embodiments, the cancer is selected from a breast cancer, skin cancer (melanoma), pancreatic cancer, lung cancer, prostate cancer, colon cancer, liver cancer (hepatocellular carcinoma), head and neck cancer, ovarian cancer and kidney cancer.

In embodiments, the fibrotic, inflammatory or proliferative disease or condition is selected from diabetic retinopathy, diabetic macular edema, macular degeneration, retinopathy of prematurity (ROP), and proliferative vitreoretinopathy (PVR).

In embodiments, the fibrotic, inflammatory or proliferative disease or condition is an autoimmune disease or condition. In embodiments, the autoimmune disease or condition is selected from systemic lupus erythematosus (SLE), inflammatory bowel disease, Crohn's disease, ulcerative colitis, graft versus host disease, multiple sclerosis, and rheumatoid arthritis.

In embodiments, a crystalline form disclosed herein, or the pharmaceutical composition as defined herein, is administered orally.

In embodiments, a crystalline form disclosed herein, or the pharmaceutical composition as defined herein, is administered daily.

In embodiments, a crystalline form disclosed herein, or the pharmaceutical composition as defined herein, is administered at a dose of between about 10 and about 400 mg/kg/day, or between about 50 and about 300 mg/kg/day, or between 100 and 250 mg/kg/day of the compound of Formula (I). In embodiments, a crystalline form disclosed herein, or the pharmaceutical composition as defined herein, is administered at a dose of about 200 mg/kg/day of the compound of Formula (I).

In embodiments, the subject is a human.

DETAILED DESCRIPTION

Figure 1:
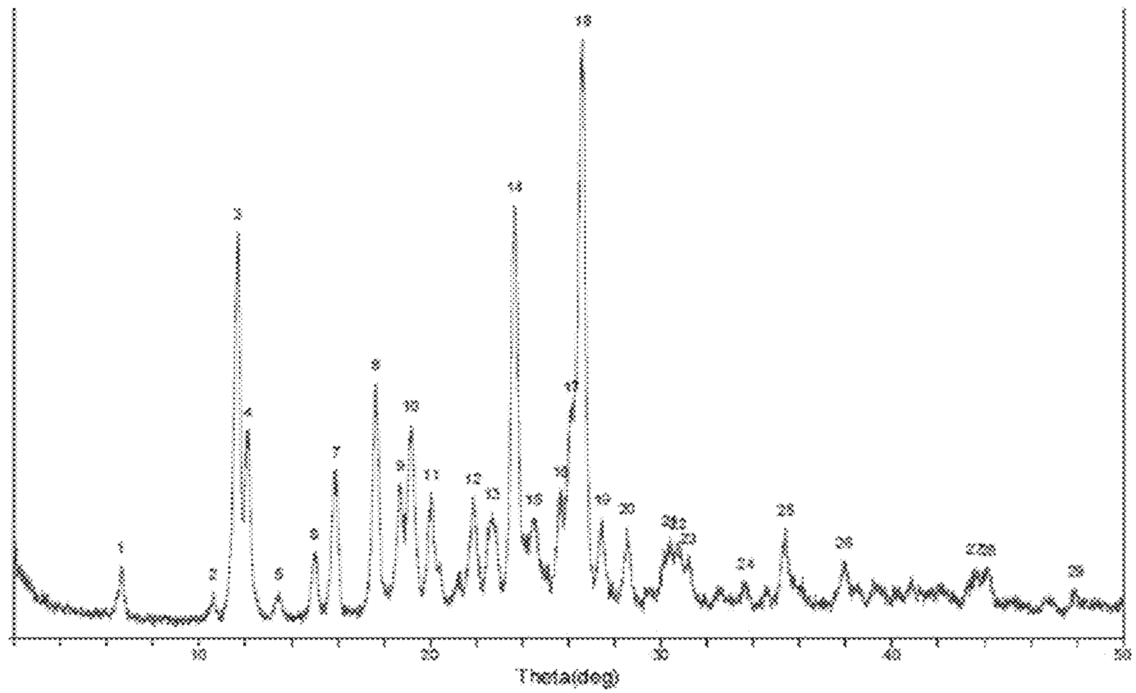
FIG. 1 shows an exemplary X-Ray Powder Diffraction (XRPD) pattern of a sample of the ethanolamine salt of (E)-2-[[3-(3-methoxy-4-propargyloxy)phenyl)-1-oxo-2-propenyl]amino]benzoic acid in crystalline Form I.

Generally, the nomenclature used herein and the laboratory procedures in organic chemistry, medicinal chemistry, pharmacology, formulation science and medicine described herein are those well-known and commonly employed in the art. Unless defined otherwise, all technical and scientific terms used herein generally have the same meaning as commonly understood by one of ordinary skill in the art.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

As used herein, and unless otherwise specified, the terms "manage," "managing" and "management" refer to preventing or slowing the progression, spread or worsening of a disease, disorder, or condition, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, amelioration of the symptoms of a particular disorder by administration of a particular pharmaceutical composition refers to any lessening, whether permanent or temporary, lasting or transient, that can be attributed to or associated with administration of the composition.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and symptoms.

The term "therapeutically effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

A "fibrotic condition", "fibrotic disease", and "fibrotic disorder" are used interchangeably herein to refer to a condition, disease or disorder that is characterized by dysregulated proliferation or activity of fibroblasts and/or abnormal accumulation of fibronectin and/or pathologic or excessive accumulation of collagenous tissue. Typically, any such disease, disorder or condition is amenable to treatment by administration of a compound having anti-fibrotic activity. Fibrotic disorders include, but are not limited to, renal fibrosis, dermal fibrosis, pancreatic fibrosis, liver fibrosis (e.g., hepatic fibrosis associated with chronic active hepatitis), and pulmonary fibrosis, including idiopathic pulmonary fibrosis (IPF) and pulmonary fibrosis from a known etiology.

"Cardiac fibrosis" refers to the formation of fibrous tissue, including cellular and extracellular components, in the lining and muscle of the heart. If present in sufficient quantities, the fibrous tissue will result in a decrease in the contractility and/or relaxation of one or more regions of the heart, resulting in functional deficit in cardiac output.

"Diabetic cardiomyopathy" refers to any one or more cardiac pathology and/or dysfunction in a subject, which is a complication of either Type I or Type II diabetes in the subject. The diabetes may be symptomatic or asymptomatic. Cardiac pathology which is characteristic of diabetic cardiomyopathy includes myocellular hypertrophy, myocardial fibrosis, and in some cases left ventricular hypertrophy. The pathologies which are contemplated arise independently from complications arising from coronary artery disease, although both diabetic complications and coronary artery complications may be present in the same subject. Diastolic dysfunction, such as an impairment in early diastolic filling, a prolongation of isovolumetric relaxation and increased atrial filling is also characteristic of diabetic cardiomyopathy, and may be identified using Doppler methods such as Doppler 2-dimensional echocardiography (for example Redford M M et al, "Burden of systolic and diastolic dysfunction in the community". JAMA (2003) 289:194-203) or radionuclide imaging for early or mild dysfunction and by standard echocardiograph testing for more severe dysfunction.

The term "kidney disease", as used herein, may refer to a disorder of at least one kidney in a subject that compromises the function of the kidney. The kidney disease may result from a primary pathology of the kidney (e.g., injury to the glomerulus or tubule), or another organ (e.g., pancreas) which adversely affects the ability of the kidney to perform biological functions. A kidney disease in a human can be the direct or indirect effect of disease. Examples of a kidney disease as a result or consequence of an indirect effect on the kidneys is kidney disease as a consequence of diabetes or systemic lupus. A kidney disease may be the result or a consequence of any change, damage, or trauma to the glomerulus, tubules or interstitial tissue in either the renal cortex or renal medulla of the kidney. The term "kidney disease", as used herein, may refer to a progressive kidney disease that over time (e.g., days, weeks, months, years) leads to a loss of renal function.

The kidney disease may include, but is not limited to, a progressive glomerular kidney disease including, without limitation, diabetic nephropathy (e.g., as a consequence of Type I or Type II diabetes or systemic lupus), primary glomerulonephritis (e.g., membranous nephropathy, focal segmental glomerulosclerosis, membranoproliferative glomerulonephritis, diffuse proliferative glomerulonephritis, membranous focal segmental glomerulosclerosis) or secondary glomerulonephritis (e.g., diabetic nephropathy, ischemic nephropathy).

The term "renal function", as used herein, refers to a physiological property of the kidney, such as the ability to retain protein thereby preventing proteinuria. Renal function can be assessed using methods known in the art such as determining one or more of glomerular filtration rate (e.g., creatinine clearance), excretion of protein in urine, blood urea nitrogen, and serum or plasma creatinine.

A progressive kidney disease treated by the salts, pharmaceutical compositions and methods described herein includes any kidney disease that can, ultimately, lead to end-stage renal disease. A progressive kidney disease that can be treated by the compositions and methods of the invention can be, for example, associated with endogenous iron deposit in the kidney (e.g., glomerulus, tubules).

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 22nd ed.; Pharmaceutical Press: 2012; Handbook of Pharmaceutical Excipients, 7th ed.; Rowe et al., Eds.; The Pharmaceutical Press: 2012; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, F L, 2009.

As used in the specification and the accompanying claims, the indefinite articles "a" and "an" and the definite article "the" include plural as well as singular referents, unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. In certain embodiments, "about" or "approximately" with reference to X-ray powder diffraction two-theta peaks means within ±0.2°.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer or an isotopic variant of a compound described herein.

The term "anti-solvent" refers to a liquid that is added to a solvent to reduce the solubility of a compound in that solvent, in some instances, resulting in precipitation of the compound.

The terms "drug", "therapeutic agent", and "chemotherapeutic agent" refer to a compound, or a pharmaceutical composition thereof, which is administered to a subject for treating, preventing, or ameliorating one or more symptoms of a disorder, disease, or condition.

The term "solvate" refers to a complex or aggregate formed by one or more molecules of a solute, e.g., a compound provided herein, and one or more molecules of a solvent, which present in stoichiometric or non-stoichiometric amounts. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "solid form" of a compound can refer to any crystalline form of the compound or any amorphous form of the compound as a free acid, the compound as a free base, as an acid addition salt of the compound, a base addition salt of the compound, a complex of the compound, or a solvate (including hydrate) of the compound, or a co-precipitation of the compound. The term "crystalline form" of a compound can refer to any crystalline form of the compound as a free acid, the compound as a free base, as an acid addition salt of the compound, a base addition salt of the compound, a complex of the compound, a solvate (including hydrate) of the compound, or a co-crystal of the compound. In many instances, the terms "crystalline form" and "solid form" can refer to those that are pharmaceutically acceptable, including, for example, those of pharmaceutically acceptable addition salts, pharmaceutically acceptable complexes, pharmaceutically acceptable solvates, pharmaceutically acceptable co-crystals, and pharmaceutically acceptable co-precipitations.

Furthermore, compounds disclosed herein may exist in one or more crystalline or amorphous forms. Unless otherwise indicated, all such forms are included in the scope of the compounds disclosed herein including any polymorphic forms.

"Pharmaceutically acceptable salt", as used herein, refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to salts formed when an acidic proton present in the parent compound either (a) is replaced by a metal ion, e.g., an alkali metal ion, an alkaline earth ion or an aluminium ion, or alkali metal or alkaline earth metal hydroxides, such as sodium, potassium, or magnesium, or (b) reacts with an organic base, such as aliphatic, alicyclic, or aromatic organic amines, such as ammonia, ethanolamine (also referred to as monoethanolamine, or 'MEA'), lysine, arginine, choline, meglumine, tert-butylamine (also referred to as 'TBA', 2-methylpropan-2-amine, or 2-amino-2-methylpropane), tris(hydroxymethyl)aminomethane (also referred to as 'Tris' or 'Tris base'), and the like. As used in the present disclosure, the term "pharmaceutically acceptable salt" excludes a piperidinium salt.

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single enantiomer, a racemic mixture, a mixture of enantiomers, or a diastereomeric mixture thereof, as determined by standard analytical methods.

Unless otherwise stated, the X-ray powder diffraction (XRPD) data provided herein was determined using a Cu Kα radiation source. The XRPD peaks recited herein should be understood to reflect a precision of ±0.2 for the 2θ peaks, and the equivalent precision for d-spacings as per Bragg's law.

The term "water sorption" refers to an observed change in water content during the course of an experiment and thereby indicating hygroscopicity, as determined by dynamic vapor sorption (DVS), of a sample of a form of (E)-2-[[3-(3-methoxy-4-propargyloxy)phenyl)-1-oxo-2-propenyl]amino]benzoic acid including a solid form, a crystalline form or a pharmaceutically acceptable salt of either, as described herein. The change in water content is recited as a % change in mass of the starting sample and all such water sorption (DVS) values recited herein will be understood to explicitly include numerical values within a +/−0.2% variance. When hygroscopicity values are recited at a particular humidity this is a reference to values as measured during the sorption cycle, for example when the stated humidity value was reached during a process of increasing humidity from 0% RH to 95% RH in the presence of the sample.

The term "weight loss" refers to an observed loss of weight, determined by thermogravimetric analysis (TGA), of a sample of a form of (E)-2-[[3-(3-methoxy-4-propargyloxy)phenyl)-1-oxo-2-propenyl]amino]benzoic acid including a solid form, a crystalline form or a pharmaceutically acceptable salt of either, as described herein. The weight loss is recited as a % loss in mass of the starting sample and all such weight loss values recited herein will be understood to explicitly include numerical values within a +/−0.2% mass unit variance.

The term "bioavailability" refers to bioavailability of one or more forms of (E)-2-[[3-(3-methoxy-4-propargyloxy) phenyl)-1-oxo-2-propenyl]amino]benzoic acid including solid forms, crystalline forms and pharmaceutically acceptable salts of either, as described herein, in plasma. Bioavailability is determined by the equation $AUC=F \cdot D/CL_T$, wherein AUC is the area under the plot of plasma concentration, F is the absolute bioavailability, D is the dose, and $CL_T$ is the total clearance. Furthermore, the term bioavailability refers to bioavailability as determined according to the experiment recited in Example 6, and referred to at Table 22, wherein bioavailability (F) is calculated using the extrapolated area under the curve ($AUC_{inf}$). Bioavailability values as recited herein will be understood to explicitly include numerical values within a +/−10% variance.

The term "endothermic onset" refers to a temperature at which an endothermic event occurs, as measured by differential scanning calorimetry (DSC), of a sample of a form of (E)-2-[[3-(3-methoxy-4-propargyloxy)phenyl)-1-oxo-2-propenyl]amino]benzoic acid including a solid form, a crystalline form or a pharmaceutically acceptable salt of either, as described herein. Endothermic onset values as recited herein will be understood to explicitly include numerical values within a +/−2.0° C. variance.

The term "melting point" refers to the temperature, as measured by differential scanning calorimetry (DSC), at which a change in state from solid to liquid occurs in a sample of a form of (E)-2-[[3-(3-methoxy-4-propargyloxy) phenyl)-1-oxo-2-propenyl]amino]benzoic acid including a solid form, a crystalline form or a pharmaceutically acceptable salt of either, as described herein. Melting point values as recited herein will be understood to explicitly include numerical values within a +/−2.0° C. variance.

The term "FaSSIF media" refers to Fasted State Simulated Intestinal Fluid media prepared using FaSSIF powder and buffer concentrate obtained from the commercial source Biorelevant (London, UK, biorelevant.com). The FaSSIF powder contains sodium taurocholate, lecithin, sodium chloride, monobasic sodium phosphate and sodium hydroxide. The FaSSIF media is prepared as described at https://biorelevant.com/learning_center/what-is-fassif/. Briefly the pH6.5 buffer containing 0.42 g of NaOH, 3.95 g of $NaH_2PO_4 \cdot H_2O$ and 6.19 g of NaCl was dissolved in 0.9 L of purified water and the pH of the solution was adjusted to 6.5 using sodium hydroxide 1N or hydrochloric acid 1N and made up to volume (1 L) with purified water at room temperature. Dissolve 2.24 g of the FaSSIF powder in 0.5 L of the pH6.5 buffer, stirring until the powder is completely dissolved, and then make up to volume (1 L) with buffer at room temperature. The prepared media contains sodium taurocholate at a concentration of 3.0 mM, lecithin at a concentration of 0.75 mM; sodium chloride at a concentration of 106 mM, and monobasic sodium phosphate at a concentration of 28.4 mM. When required, FaSSIF (pH 7.5) media was prepared as described and adjusted to the desired pH using sodium hydroxide 1N or hydrochloric acid 1N.

The term "FeSSIF media" refers to Fed State Simulated Intestinal Fluid media prepared using FeSSIF powder and buffer concentrate obtained from the commercial source Biorelevant (London, UK, biorelevant.com). The FeSSIF powder contains sodium taurocholate, lecithin, sodium chloride, sodium hydroxide and acetic acid. The FeSSIF media is prepared as described at https://biorelevant.com/learning_center/what-is-fessif/. Briefly, the pH5.0 buffer containing 44.04 g of NaOH, 8.65 g of glacial acetic acid and 11.87 g of NaCl was dissolved in 0.9 L of purified water and the pH of the solution was adjusted to 5.0 using sodium hydroxide 1N or hydrochloric acid 1N and made up to volume (1 L) with purified water at room temperature. Dissolve 11.20 g of FeSSIF powder in 0.5 L of the pH5.0 buffer, stirring until the powder was completely dissolved, and then make up to volume (1 L) with buffer at room temperature. The prepared media contains 15.0 mM sodium taurocholate, 3.75 mM lecithin, 203 mM sodium chloride, and 144 mM acetic acid. When required, FeSSIF (pH 7.8) media was prepared as described and adjusted to the desired pH using sodium hydroxide 1N or hydrochloric acid 1N.

Solid Forms

The present disclosure relates, in part, to solid forms (e.g., crystalline forms) of (E)-2-[[3-(3-methoxy-4-propargyloxy) phenyl)-1-oxo-2-propenyl]amino]benzoic acid or pharmaceutically acceptable salts thereof having useful physicochemical and/or pharmacokinetic properties. The present disclosure also relates to certain pharmaceutically acceptable salts of (E)-2-[[3-(3-methoxy-4-propargyloxy)phenyl)-1-oxo-2-propenyl]amino]benzoic acid and solid or crystalline forms of those salts, which may provide for one or more surprising advantages over (E)-2-[[3-(3-methoxy-4-propargyloxy)phenyl)-1-oxo-2-propenyl]amino]benzoic acid, which is also referred to herein as the "non-salt form," "free form," or the "free acid form" of (E)-2-[[3-(3-methoxy-4-propargyloxy)phenyl)-1-oxo-2-propenyl]amino]benzoic acid, as described herein. Some embodiments disclosed herein include crystalline forms of certain pharmaceutically acceptable salts of (E)-2-[[3-(3-methoxy-4-propargyloxy) phenyl)-1-oxo-2-propenyl]amino]benzoic acid.

The compound (E)-2-[[3-(3-methoxy-4-propargyloxy) phenyl)-1-oxo-2-propenyl]amino]benzoic acid, also known as, for example, (E)-2-(3-(3-methoxy-4-(prop-2-yn-1-yloxy)phenyl)acrylamido)benzoic acid, (E)-2-[[3-(3-methoxy-4-propargyloxy)phenyl)-1-oxo-2-propenyl]amino] benzoic acid, 3-methoxy-4-propargyloxycinnamoyl anthranilic acid, or 'FT011', has been described, including its preparation and biological evaluation, in International Patent Application WO 2008/003141, the disclosure of which is incorporated herein by reference in its entirety.

The solid forms, pharmaceutically acceptable salts, and crystalline forms thereof described herein may be characterized using a number of methods known to a person skilled in the art, including thin layer chromatography (TLC), gel electrophoresis, high performance liquid chromatography (HPLC), gas chromatography (GC), nuclear magnetic resonance (NMR), and mass spectrometry (MS), single crystal X-ray diffraction, X-ray powder diffraction (XRPD), microscopy (e.g., scanning electron microscopy (SEM)), thermal analysis (e.g., differential scanning calorimetry (DSC), thermogravimetric analysis (TGA), and hot-stage microscopy, and spectroscopy (e.g., infrared, Raman, solid-state nuclear magnetic resonance). For solid forms, the particle size and size distribution may be determined by conventional methods, such as laser light scattering technique. The purity of the solid forms, pharmaceutically acceptable salts, and crystalline forms thereof provided herein may be determined by standard analytical methods, such as thin layer chromatography (TLC), gel electrophoresis, gas chromatography, high performance liquid chromatography (HPLC), and mass spectrometry (MS).

In embodiments, provided herein is (E)-2-[[3-(3-methoxy-4-propargyloxy)phenyl)-1-oxo-2-propenyl]amino] benzoic acid in a solid form. In some embodiments, the solid form is crystalline.

In some embodiments, the solid form of (E)-2-[[3-(3-methoxy-4-propargyloxy)phenyl)-1-oxo-2-propenyl]amino] benzoic acid is a solid form of a pharmaceutically acceptable salt of (E)-2-[[3-(3-methoxy-4-propargyloxy)phenyl)-1-oxo-2-propenyl]amino]benzoic acid. In some embodiments, the solid form of (E)-2-[[3-(3-methoxy-4-propargyloxy)phenyl)-1-oxo-2-propenyl]amino]benzoic acid is a crystalline form of a pharmaceutically acceptable salt of (E)-2-[[3-(3-methoxy-4-propargyloxy)phenyl)-1-oxo-2-propenyl]amino] benzoic acid, or a solvate thereof.

In any embodiments described herein, the term "pharmaceutically acceptable salt" excludes a piperidinium salt.

The pharmaceutically acceptable salt of (E)-2-[[3-(3-methoxy-4-propargyloxy)phenyl)-1-oxo-2-propenyl]amino] benzoic acid may be selected from, but not limited to, a potassium salt, meglumine salt, ethanolamine salt, tris(hydroxymethyl)aminomethane (Tris) salt, tert-butylamine (TBA) salt, ammonium salt, or lysine salt. In some embodiments, the pharmaceutically acceptable salt is a meglumine salt, ethanolamine salt, tris(hydroxymethyl)aminomethane (Tris) salt, or tert-butylamine (TBA) salt. In some embodiments, the pharmaceutically acceptable salt is an ethanolamine salt or a tert-butylamine salt. In certain embodiments, the pharmaceutically acceptable salt is an ethanolamine salt.

In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein may be solvated. In various embodiments, the solvent in the solvate is pharmaceutically acceptable. In one embodiment, the solvent in the solvate is an alcohol. In another embodiment, the solvent in the solvate is methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, or ethyleneglycol. In yet another embodiment, the solvent in the solvate is methanol or ethanol. In other embodiments, the solvent in the solvate is water, methanol, ethanol, n-propanol, isopropanol, acetic acid, or ethyl acetate. In yet other embodiments, the solvent in the solvate is acetic acid or ethyl acetate. In some embodiments, the solid form (e.g., crystalline form) of (E)-2-[[3-(3-methoxy-4-propargyloxy) phenyl)-1-oxo-2-propenyl]amino]benzoic acid or a pharmaceutically acceptable salt thereof provided herein is unsolvated.

In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein may be a hydrate. Accordingly, in one embodiment, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein may be a hemihydrate. In another embodiment, the solid form (e.g., crystalline form) of (E)-2-[[3-(3-methoxy-4-propargyloxy) phenyl)-1-oxo-2-propenyl]amino]benzoic acid or a pharmaceutically acceptable salt thereof provided herein may be a monohydrate. In another embodiment, the solid form (e.g., crystalline form) of (E)-2-[[3-(3-methoxy-4-propargyloxy) phenyl)-1-oxo-2-propenyl]amino]benzoic acid or a pharmaceutically acceptable salt thereof provided herein may be a dihydrate. In yet another embodiment, the solid form (e.g., crystalline form) of (E)-2-[[3-(3-methoxy-4-propargyloxy) phenyl)-1-oxo-2-propenyl]amino]benzoic acid or a pharmaceutically acceptable salt thereof provided herein may be a trihydrate. In yet another embodiment, the solid form (e.g., crystalline form) of (E)-2-[[3-(3-methoxy-4-propargyloxy) phenyl)-1-oxo-2-propenyl]amino]benzoic acid or a pharmaceutically acceptable salt thereof provided herein may be a tetrahydrate. In still another embodiment, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein may be a pentahydrate.

In various embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein exhibits advantageous solubility, bioavailability, stability, processability, ease of manufacture, and/or pharmacokinetic properties. For example, the solid form (e.g., crystalline form) of (E)-2-[[3-(3-methoxy-4-propargyloxy)phenyl)-1-oxo-2-propenyl] amino]benzoic acid provided herein may provide long-term stability, low hygroscopicity, improved dissolution, and superior pharmacokinetic properties. In some embodiments, the solid form (e.g., crystalline form) of (E)-2-[[3-(3-methoxy-4-propargyloxy)phenyl)-1-oxo-2-propenyl]amino] benzoic acid or a pharmaceutically acceptable salt thereof provided herein has an improved property selected from the group consisting of: increased stability, increased solubility, increased dissolution, increased bioavailability, increased dose response, or another property described herein. In some embodiments, the increased stability is characterised by modulated (e.g., reduced) water sorption as determined by dynamic vapor sorption (DVS), modulated (e.g., increased) endothermic onset as measured by differential scanning calorimetry (DSC), and/or modulated (e.g., reduced) weight loss as determined by thermogravimetric analysis (TGA).

In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a water sorption of less than 10%, 9%, 8%, 7%, 6%, 5%, 4%, 3%, 2%, 1.9%, 1.8%, 1.7%, 1.6%, 1.5%, 1.4%, 1.3%, 1.2%, 1%, 0.9%, 0.8%, 0.7%, 0.6%, 0.5%, 0.4%, 0.3%, 0.2%, or 0.1% at 25° C. and 80% relative humidity as determined by dynamic vapor sorption (DVS). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a water sorption of from 0.1% to 10% at 25° C. and 80% relative humidity as determined by dynamic vapor sorption (DVS). In one embodiment, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a water sorption of from 0.1 to 10%, from 0.1 to 9%, from 0.1 to 8%, from 0.1 to 7%, from 0.1 to 6%, from 0.1 to 5%, from 0.1 to 4%, from 0.1 to 3%, from 0.1 to 2%, or from 0.1 to 1% at 25° C. and 80% relative humidity as determined by DVS. In one embodiment, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a water sorption of from 0.1 to 1.7% at 25° C. and 80% relative humidity as determined by DVS. In another embodiment, the solid form (e.g., crystalline form) of (E)-2-[[3-(3-methoxy-4-propargyloxy) phenyl)-1-oxo-2-propenyl]amino]benzoic acid or a pharmaceutically acceptable salt thereof provided herein has a water sorption of from 0.49% to 8.82% at 25° C. and 80% relative humidity as determined by DVS. In yet another embodiment, the solid form (e.g., crystalline form) of (E)-2-[[3-(3-methoxy-4-propargyloxy)phenyl)-1-oxo-2-propenyl]amino] benzoic acid or a pharmaceutically acceptable salt thereof provided herein has a water sorption of from 0.49% to 6.93% at 25° C. and 80% relative humidity as determined by DVS. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a water sorption of from 0.49% to 6.05% at 25° C. and 80% relative humidity as determined by DVS. In certain embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a water sorption of from 0.49% to 1.61% at 25° C. and 80% relative humidity as determined by DVS. In certain embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a water sorption of from 0.49% to 1.07% at 25° C. and 80% relative humidity as determined by DVS. In certain embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a water sorption of from 1.07% to 8.82% at 25° C. and 80% relative humidity as determined by DVS.

In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has an endothermic onset of from 29° C. to 187° C., as measured by differential scanning calorimetry (DSC). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has an endothermic onset of from 116° C. to 187° C., as measured by DSC. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a melting point of from 57° C. to 199° C., as measured by DSC. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a melting point of from 155° C. to 199° C., as measured by DSC. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has an endothermic onset of from 29° C. to 187° C., and a melting point of from 57° C. to 199° C., as measured by DSC. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has an endothermic onset of from 116° C. to 187° C., and a melting point of from 155° C. to 199° C., as measured by DSC.

In some embodiments, the solid form (e.g., crystalline form) of (E)-2-[[3-(3-methoxy-4-propargyloxy)phenyl)-1-oxo-2-propenyl]amino]benzoic acid a or pharmaceutically acceptable salt thereof provided herein has a weight loss of less than 3%, 2.5%, 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0.05% when heated from 25° C. to 120° C. as determined by thermogravimetric analysis (TGA). In some embodiments, the solid form (e.g., crystalline form) of (E)-2-[[3-(3-methoxy-4-propargyloxy) phenyl)-1-oxo-2-propenyl]amino]benzoic acid or a pharmaceutically acceptable salt thereof provided herein has a weight loss of from 0.05% to 3% when heated from 25° C. to 120° C. as determined by thermogravimetric analysis (TGA). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a weight loss of from 0.01% to 1% when heated from 25° C. to 120° C. as determined by TGA. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a weight loss of from 0.07% to 8.94%, or from 0.07% to 0.94% when heated from 25° C. to 120° C. as determined by TGA.

In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of at least 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml at 24 hours in FaSSIF media (pH 7.5). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of from about 2 mg/ml to about 10 mg/ml, about 2 mg/ml to about 9 mg/ml, about 2 mg/ml to about 8 mg/ml, about 2 mg/ml to about 7 mg/ml, about 2 mg/ml to about 6 mg/ml, or about 2 mg/ml to about 5 mg/ml at 24 hours in FaSSIF media (pH 7.5). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of from 2.4 mg/ml to 5.14 mg/ml at 24 hours in FaSSIF media (pH 7.5). In some embodiments, the solid form (e.g., crystalline form) of (E)-2-[[3-(3-methoxy-4-propargyloxy)phenyl)-1-oxo-2-propenyl]amino]benzoic acid a or pharmaceutically acceptable salt thereof provided herein has a solubility of from 2.4 mg/ml to greater than 5.14 mg/ml at 24 hours in FaSSIF media (pH 7.5).

In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of at least 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml at 24 hours in FeSSIF media (pH 7.8). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of from about 1 mg/ml to about 10 mg/ml, about 1 mg/ml to about 9 mg/ml, about 1 mg/ml to about 8 mg/ml, about 1 mg/ml to about 7 mg/ml, about 1 mg/ml to about 6 mg/ml, or about 1 mg/ml to about 5 mg/ml at 24 hours in FeSSIF media (pH 7.8). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of from 1.2 mg/ml to 5.14 mg/ml at 24 hours in FeSSIF media (pH 7.8). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of from 1.2 mg/ml to greater than 5.14 mg/ml at 24 hours in FeSSIF media (pH 7.8).

In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of from 2.4 mg/ml to 5.14 mg/ml at 24 hours in FaSSIF media (pH 7.5), and a solubility of from 1.2 mg/ml to 5.14 mg/ml at 24 hours in FeSSIF media (pH 7.8). In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a solubility of from 2.4 mg/ml to greater than 5.14 mg/ml at 24 hours in FaSSIF media (pH 7.5), and a solubility of from 1.2 mg/ml to greater than 5.14 mg/ml at 24 hours in FeSSIF media (pH 7.8).

In embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has improved bioavailability.

Bioavailability can be improved via an increase in AUC (area under the plot of plasma concentration), reduced time to $t_{max}$ (the time to reach peak blood serum levels), or increased $C_{max}$. For example, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein can result in higher plasma concentrations of (E)-2-[[3-(3-methoxy-4-propargyloxy)phenyl)-1-oxo-2-propenyl]amino]benzoic acid when compared to a reference form.

As will be appreciated by persons skilled in the art, AUC is useful in estimating bioavailability, and in estimating total clearance ($CL_T$). In some instances, $AUC=F \cdot D/CL_T$, where D is the dose, and F is the absolute bioavailability.

For example, in some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a bioavailability of at least 39 F %, 44 F %, 49 F %, 54 F %, 59 F %, 54 F %, 59 F %, 64 F %, 69 F %, 74 F %, 79 F %, 84 F %, 89 F %, 94 F %, or 99 F %. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a bioavailability of at least 50 F %, 55 F %, 60 F %, 65 F %, 70 F %, 75 F %, 80 F %, 85 F %, 90 F %, 95 F %, or 99 F %. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a bioavailability of from 39 F % to 99 F %, from 39 F % to 94 F %, from 39 F % to 89 F %, from 39 F % to 84 F %, from 39 F % to 79 F %, from 39 F % to 74 F %, from 39 F % to 69 F %, from 39 F % to 64 F %, from 39 F % to 59 F %, from 39 F % to 54 F %, from 39 F % to 49 F %, or from 39 F % to 44 F %. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a bioavailability of from 39 F % to 82 F %. In some embodiments, the bioavailability is oral bioavailability.

In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a bioavailability of at least about 1.1×, about 1.2×, about 1.3×, about 1.4×, about 1.5×, about 1.6×, about 1.7×, about 1.8×, about 1.9×, about 2.0×, about 2.1×, about 2.2×, about 2.3×, about 2.4×, about 2.5×, about 2.6×, about 2.7×, about 2.8×, about 2.9×, or about 3.0× compared to a bioavailability of the free form of (E)-2-[[3-(3-methoxy-4-propargyloxy)phenyl)-1-oxo-2-propenyl]amino]benzoic acid. In some embodiments, the solid form (e.g., crystalline form) of (E)-2-[[3-(3-methoxy-4-propargyloxy)phenyl)-1-oxo-2-propenyl]amino]benzoic acid or a pharmaceutically acceptable salt thereof provided herein has a bioavailability of at least about 1.4×, about 1.6×, about 1.8×, about 2.0×, or about 2.3× compared to a bioavailability of the free form of (E)-2-[[3-(3-methoxy-4-propargyloxy)phenyl)-1-oxo-2-propenyl]amino]benzoic acid. In some embodiments, the bioavailability is oral bioavailability.

Salts and Solid or Crystalline Forms of the Salts

In some embodiments, provided herein are pharmaceutically acceptable salts of (E)-2-[[3-(3-methoxy-4-propargyloxy)phenyl)-1-oxo-2-propenyl]amino]benzoic acid, and solid or crystalline forms thereof. In various embodiments, the pharmaceutically acceptable salt may be selected from, but is not limited to, a potassium salt, meglumine salt, ethanolamine salt, tris(hydroxymethyl)aminomethane (Tris)

salt, tert-butylamine (TBA) salt, ammonium salt, or lysine salt. In some embodiments, the pharmaceutically acceptable salt is a meglumine salt, ethanolamine salt, tris(hydroxymethyl)aminomethane (Tris) salt, or tert-butylamine (TBA) salt. In some embodiments, the pharmaceutically acceptable salt is an ethanolamine salt or a tert-butylamine salt. In certain embodiments, the pharmaceutically acceptable salt is an ethanolamine salt.

In some embodiments, provided herein is an ethanolamine salt of (E)-2-[[3-(3-methoxy-4-propargyloxy)phenyl)-1-oxo-2-propenyl]amino]benzoic acid, including solid or crystalline forms thereof.

The term "ethanolamine", as used herein, refers to a compound (and the related salt formed using said compound) also known as e.g. 2-aminoethan-1-ol, 2-aminoethanol, monoethanolamine, or "MEA".

In some embodiments, the ethanolamine salt of (E)-2-[[3-(3-methoxy-4-propargyloxy)phenyl)-1-oxo-2-propenyl]amino]benzoic acid may be represented by Formula (II):

Formula (II)

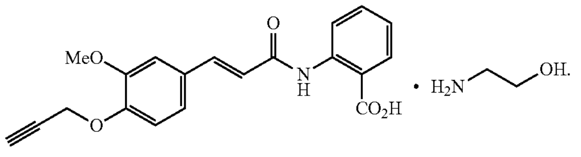

In some embodiments, provided herein is a tert-butylamine (TBA) salt of (E)-2-[[3-(3-methoxy-4-propargyloxy)phenyl)-1-oxo-2-propenyl]amino]benzoic acid, including solid or crystalline forms thereof.

In some embodiments, provided herein is a meglumine salt of (E)-2-[[3-(3-methoxy-4-propargyloxy)phenyl)-1-oxo-2-propenyl]amino]benzoic acid, including solid or crystalline forms thereof.

In some embodiments, provided herein is a tris(hydroxymethyl)aminomethane (Tris) salt of (E)-2-[[3-(3-methoxy-4-propargyloxy)phenyl)-1-oxo-2-propenyl]amino]benzoic acid, including solid or crystalline forms thereof.

In some embodiments, provided herein is a potassium salt of (E)-2-[[3-(3-methoxy-4-propargyloxy)phenyl)-1-oxo-2-propenyl]amino]benzoic acid, including solid or crystalline forms thereof.

In some embodiments, provided herein is an ammonium salt of (E)-2-[[3-(3-methoxy-4-propargyloxy)phenyl)-1-oxo-2-propenyl]amino]benzoic acid, including solid or crystalline forms thereof.

In some embodiments, provided herein is a lysine salt of (E)-2-[[3-(3-methoxy-4-propargyloxy)phenyl)-1-oxo-2-propenyl]amino]benzoic acid, including solid or crystalline forms thereof.

In various embodiments, the pharmaceutically acceptable salts of (E)-2-[[3-(3-methoxy-4-propargyloxy)phenyl)-1-oxo-2-propenyl]amino]benzoic acid, or solid or crystalline forms thereof, provided herein advantageously exhibit improved solubility, bioavailability, stability, processability, ease of manufacture, and/or pharmacokinetic properties. As a result, the pharmaceutically acceptable salts of (E)-2-[[3-(3-methoxy-4-propargyloxy)phenyl)-1-oxo-2-propenyl]amino]benzoic acid or solid or crystalline forms thereof provided herein may provide long-term stability, low hygroscopicity, improved dissolution, and superior pharmacokinetic properties compared to the free form of (E)-2-[[3-(3-methoxy-4-propargyloxy)phenyl)-1-oxo-2-propenyl]amino]benzoic acid. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have an improved property as compared to the free form of (E)-2-[[3-(3-methoxy-4-propargyloxy)phenyl)-1-oxo-2-propenyl]amino]benzoic acid, wherein the improved property is selected from the group consisting of: increased stability, increased solubility, increased dissolution, increased bioavailability, increased dose response, or another property described herein. In some embodiments, the increased stability is characterised by modulated (e.g., reduced) water sorption as determined by dynamic vapor sorption (DVS), modulated (e.g., increased) endothermic onset as measured by differential scanning calorimetry (DSC), and/or modulated (e.g., reduced) weight loss as determined by thermogravimetric analysis (TGA).

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a water sorption of less than 10%, 9%, 8%, 7%, 6%, 5%, 4%, 3%, 2%, 1.9%, 1.8%, 1.7%, 1.6%, 1.5%, 1.4%, 1.3%, 1.2%, 1%, 0.9%, 0.8%, 0.7%, 0.6%, 0.5%, 0.4%, 0.3%, 0.2%, or 0.1% at 25° C. and 80% relative humidity as determined by dynamic vapor sorption (DVS). In one embodiment, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a water sorption of from 0.1 to 10%, from 0.1 to 9%, from 0.1 to 8%, from 0.1 to 7%, from 0.1 to 6%, from 0.1 to 5%, from 0.1 to 4%, from 0.1 to 3%, from 0.1 to 2%, or from 0.1 to 1% at 25° C. and 80% relative humidity as determined by DVS. In another embodiment, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a water sorption of from 0.49% to 8.82% at 25° C. and 80% relative humidity as determined by DVS. In yet another embodiment, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a water sorption of from 0.49% to 6.93% at 25° C. and 80% relative humidity as determined by DVS. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a water sorption of from 0.49% to 6.05% at 25° C. and 80% relative humidity as determined by DVS. In certain embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a water sorption of from 0.49% to 1.61% at 25° C. and 80% relative humidity as determined by DVS. In certain embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a water sorption of from 0.49% to 1.07% at 25° C. and 80% relative humidity as determined by DVS.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have an endothermic onset of from 29° C. to 203° C., as measured by differential scanning calorimetry (DSC). In some embodiments, the pharmaceutically acceptable salts of (E)-2-[[3-(3-methoxy-4-propargloxy)phenyl)-1-oxo-2-propenyl]amino]benzoic acid or solid or crystalline forms thereof provided herein have an endothermic onset of from 116° C. to 203° C., as measured by DSC. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a melting point of from 57° C. to 204° C., as measured by DSC. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a melting point of from 155° C. to 204° C., as measured by DSC. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have an endothermic onset of from 29° C. to 203° C., and a melting point of from 57° C. to 204° C., as measured by DSC. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have an endothermic onset of from 116° C. to 203° C., and a melting point of from 155° C. to 204° C., as measured by DSC.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a weight loss of less than 3%, 2.5%, 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0.05% when heated from 25° C. to 120° C. as determined by thermogravimetric analysis (TGA). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a weight loss of from 0.05% to 3% when heated from 25° C. to 120° C. as determined by thermogravimetric analysis (TGA). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a weight loss of from 0.07% to 5.24% when heated from 25° C. to 120° C. as determined by TGA. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a weight loss of from 0.07% to 8.94%, or from 0.07% to 0.94% when heated from 25° C. to 120° C. as determined by TGA.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of at least 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml at 24 hours in FaSSIF media (pH 7.5). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of from about 2 mg/ml to about 10 mg/ml, about 2 mg/ml to about 9 mg/ml, about 2 mg/ml to about 8 mg/ml, about 2 mg/ml to about 7 mg/ml, about 2 mg/ml to about 6 mg/ml, or about 2 mg/ml to about 5 mg/ml at 24 hours in FaSSIF media (pH 7.5). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of from 2.4 mg/ml to 5.14 mg/ml at 24 hours in FaSSIF media (pH 7.5). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of from 2.4 mg/ml to greater than 5.14 mg/ml at 24 hours in FaSSIF media (pH 7.5).

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of at least 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml at 24 hours in FeSSIF media (pH 7.8). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of from about 1 mg/ml to about 10 mg/ml, about 1 mg/ml to about 9 mg/ml, about 1 mg/ml to about 8 mg/ml, about 1 mg/ml to about 7 mg/ml, about 1 mg/ml to about 6 mg/ml, or about 1 mg/ml to about 5 mg/ml at 24 hours in FeSSIF media (pH 7.8). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of from 1.2 mg/ml to 5.14 mg/ml at 24 hours in FeSSIF media (pH 7.8). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of from 1.2 mg/ml to greater than 5.14 mg/ml at 24 hours in FeSSIF media (pH 7.8).

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of from 2.4 mg/ml to 5.14 mg/ml at 24 hours in FaSSIF media (pH 7.5), and a solubility of from 1.2 mg/ml to 5.14 mg/ml at 24 hours in FeSSIF media (pH 7.8). In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of from 2.4 mg/ml to greater than 5.14 mg/ml at 24 hours in FaSSIF media (pH 7.5), and a solubility of from 1.2 mg/ml to greater than 5.14 mg/ml at 24 hours in FeSSIF media (pH 7.8).

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of at least 0.04 mg/ml, 0.05 mg/ml, 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1 mg/ml at 24 hours in media at pH 6.8. In certain embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a solubility of at least 0.06 mg/ml at 24 hours in media at pH 6.8. In some embodiments, the pharmaceutically acceptable salts of (E)-2-[[3-(3-methoxy- 4-propargyloxy)phenyl)-1-oxo-2-propenyl]amino]benzoic acid or solid or crystalline forms thereof provided herein have a solubility of from 0.048 mg/ml to 0.090 mg/ml at 24 hours in media at pH 6.8.

In embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have improved bioavailability.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a bioavailability of at least 39 F %, 44 F %, 49 F %, 54 F %, 59 F %, 54 F %, 59 F %, 64 F %, 69 F %, 74 F %, 79 F %, 84 F %, 89 F %, 94 F %, or 99 F %. In some embodiments, the pharmaceutically acceptable salts of (E)-2-[[3-(3-methoxy-4-propargyloxy) phenyl)-1-oxo-2-propenyl]amino]benzoic acid or solid or crystalline forms thereof provided herein have a bioavailability of at least 50 F %, 55 F %, 60 F %, 65 F %, 70 F %, 75 F %, 80 F %, 85 F %, 90 F %, 95 F %, or 99 F %. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a bioavailability of from 39 F % to 99 F %, from 39 F % to 94 F %, from 39 F % to 89 F %, from 39 F % to 84 F %, from 39 F % to 79 F %, from 39 F % to 74 F %, from 39 F % to 69 F %, from 39 F % to 64 F %, from 39 F % to 59 F %, from 39 F % to 54 F %, from 39 F % to 49 F %, or from 39 F % to 44 F %. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a bioavailability of from 39 F % to 82 F %. In some embodiments, the bioavailability is oral bioavailability.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a bioavailability of at least about 1.1×, about 1.2×, about 1.3×, about 1.4×, about 1.5×, about 1.6×, about 1.7×, about 1.8×, about 1.9×, about 2.0×, about 2.1×, about 2.2×, about 2.3×, about 2.4×, about 2.5×, about 2.6×, about 2.7×, about 2.8×, about 2.9×, or about 3.0× compared to a bioavailability of the free form of (E)-2-[[3-(3-methoxy-4-propargyloxy)phenyl)-1-oxo-2-propenyl]amino]benzoic acid. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a bioavailability of at least about 1.4×, about 1.6×, about 1.8×, about 2.0×, or about 2.3× compared to a bioavailability of the free form of (E)-2-[[3-(3-methoxy-4-propargyloxy)phenyl)-1-oxo-2-propenyl]amino]benzoic acid. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a bioavailability of from 1.1× to 3.0× a bioavailability of the free form of (E)-2-[[3-(3-methoxy-4-propargyloxy)phenyl)-1-oxo-2-propenyl]amino]benzoic acid. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a bioavailability of from 1.4× to 2.3× a bioavailability of the free form of (E)-2-[[3-(3-methoxy-4-propargyloxy) phenyl)-1-oxo-2-propenyl]amino]benzoic acid. In some embodiments, the bioavailability is oral bioavailability.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein may be solvated. In various embodiments, the solvent in the solvate is pharmaceutically acceptable. In one embodiment, the solvent in the solvate is an alcohol. In another embodiment, the solvent in the solvate is methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, or ethyleneglycol. In yet another embodiment, the solvent in the solvate is methanol or ethanol. In other embodiments, the solvent in the solvate is water, methanol, ethanol, n-propanol, isopropanol, acetic acid, or ethyl acetate. In yet other embodiments, the solvent in the solvate is acetic acid or ethyl acetate. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein are unsolvated.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein may be a hydrate. Accordingly, in one embodiment, the pharmaceutically acceptable salts of (E)-2-[[3-(3-methoxy-4-propargyloxy)phenyl)-1-oxo-2-propenyl]amino]benzoic acid or solid or crystalline forms thereof provided herein may be a hemihydrate. In another embodiment, the pharmaceutically acceptable salts of (E)-2-[[3-(3-methoxy-4-propargyloxy)phenyl)-1-oxo-2-propenyl]amino]benzoic acid or solid or crystalline forms thereof provided herein may be a monohydrate. In another embodiment, the pharmaceutically acceptable salts of (E)-2-[[3-(3-methoxy-4-propargyloxy)phenyl)-1-oxo-2-propenyl]amino]benzoic acid or solid or crystalline forms thereof provided herein may be a dihydrate. In yet another embodiment, the pharmaceutically acceptable salts of (E)-2-[[3-(3-methoxy-4-propargyloxy)phenyl)-1-oxo-2-propenyl]amino] benzoic acid or solid or crystalline forms thereof provided herein may be a trihydrate. In yet another embodiment, the pharmaceutically acceptable salts of (E)-2-[[3-(3-methoxy-4-propargyloxy)phenyl)-1-oxo-2-propenyl]amino]benzoic acid or solid or crystalline forms thereof provided herein may be a tetrahydrate. In still another embodiment, the pharmaceutically acceptable salts of (E)-2-[[3-(3-methoxy-4-propargyloxy)phenyl)-1-oxo-2-propenyl]amino]benzoic acid or solid or crystalline forms thereof provided herein may be a pentahydrate.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein are isolated pharmaceutically acceptable salts of (E)-2-[[3-(3-methoxy-4-propargyloxy) phenyl)-1-oxo-2-propenyl]amino]benzoic acid or solid or crystalline forms thereof.

In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein have a chemical purity of at least 90%, at least 95%, at least 98%, or at least 99%. In some embodiments, the pharmaceutically acceptable salts of (E)-2-[[3-(3-methoxy-4-propargyloxy)phenyl)-1-oxo-2-propenyl]amino]benzoic acid or solid or crystalline forms thereof provided herein, wherein the salt is selected from meglumine salt, ethanolamine salt, tris(hydroxymethyl)aminomethane (Tris) salt, or tert-butylamine (TBA) salt, have a chemical purity of at least 90%, at least 95%, at least 98%, or at least 99%.

In embodiments, the pharmaceutically acceptable salts of (E)-2-[[3-(3-methoxy-4-propargyloxy)phenyl)-1-oxo-2-propenyl]amino]benzoic acid provided herein are crystalline.

Ethanolamine Salt of (E)-2-[[3-(3-methoxy-4-propargyloxy)phenyl)-1-oxo-2-propenyl]amino]benzoic acid, and Solid or Crystalline Forms Thereof In embodiments, provided herein is the ethanolamine salt of (E)-2-[[3-(3-methoxy-4-propargyloxy)phenyl)-1-oxo-2-propenyl]amino]benzoic acid, including solid and crystalline forms thereof.

In embodiments, provided herein is a solid form of the ethanolamine salt of (E)-2-[[3-(3-methoxy-4-propargyloxy)phenyl)-1-oxo-2-propenyl]amino]benzoic acid.

In some embodiments, the ethanolamine salt of (E)-2-[[3-(3-methoxy-4-propargyloxy)phenyl)-1-oxo-2-propenyl]amino]benzoic acid is unsolvated.

In some embodiments, provided herein is a crystalline form of the ethanolamine salt of (E)-2-[[3-(3-methoxy-4-propargyloxy)phenyl)-1-oxo-2-propenyl]amino]benzoic acid. In an embodiment, the crystalline form is of an unsolvated ethanolamine salt of (E)-2-[[3-(3-methoxy-4-propargyloxy)phenyl)-1-oxo-2-propenyl]amino]benzoic acid.

In some embodiments, the crystalline form of the ethanolamine salt of (E)-2-acid [[3-(3-methoxy-4-propargyloxy)phenyl)-1-oxo-2-propenyl]amino]benzoic provided herein is crystalline Form I.

In some embodiments, crystalline Form I of the ethanolamine salt of (E)-2-[[3-(3-methoxy-4-propargyloxy)phenyl)-1-oxo-2-propenyl]amino]benzoic acid has an X-ray powder diffraction (XRPD) pattern. FIG. 1 depicts an example of an XRPD pattern for crystalline Form I. In some embodiments, the XRPD pattern of the crystalline Form I of the ethanolamine salt of (E)-2-[[3-(3-methoxy-4-propargyloxy)phenyl)-1-oxo-2-propenyl]amino]benzoic acid includes at least one diffraction peak selected from 6.6, 11.7, 15.9, 17.7, 23.7, and 26.6 degrees 2θ (±0.2 degrees 2θ). In some embodiments, crystalline Form I of the ethanolamine salt of (E)-2-[[3-(3-methoxy-4-propargyloxy)phenyl)-1-oxo-2-propenyl]amino]benzoic acid has an XRPD pattern comprising at least two peaks selected from 6.6, 11.7, 15.9, 17.7, 23.7, and 26.6 degrees 2θ (±0.2 degrees 2θ). In some embodiments, crystalline Form I of the ethanolamine salt of (E)-2-[[3-(3-methoxy-4-propargyloxy)phenyl)-1-oxo-2-propenyl]amino]benzoic acid has an XRPD pattern comprising at least three peaks selected from 6.6, 11.7, 15.9, 17.7, 23.7, and 26.6 degrees 2θ (±0.2 degrees 2θ). In some embodiments, crystalline Form I of the ethanolamine salt of (E)-2-[[3-(3-methoxy-4-propargyloxy)phenyl)-1-oxo-2-propenyl]amino]benzoic acid has an XRPD pattern comprising the peaks at 6.6, 11.7, 15.9, 17.7, 23.7, and 26.6 degrees 2θ (±0.2 degrees 2θ). In some embodiments, crystalline Form I of the ethanolamine salt of (E)-2-[[3-(3-methoxy-4-propargyloxy)phenyl)-1-oxo-2-propenyl]amino]benzoic acid has an XRPD pattern comprising at least one peak selected from 6.6, 11.7, 15.0, 15.9, 17.7, 18.7 and 19.2 degrees 2θ (±0.2 degrees 2θ). In some embodiments, crystalline Form I of the ethanolamine salt of (E)-2-[[3-(3-methoxy-4-propargyloxy)phenyl)-1-oxo-2-propenyl]amino]benzoic acid has an XRPD pattern comprising at least two peaks selected from 6.6, 11.7, 15.0, 15.9, 17.7, 18.7 and 19.2 degrees 2θ (±0.2 degrees 2θ). In some embodiments, crystalline Form I of the ethanolamine salt of (E)-2-[[3-(3-methoxy-4-propargyloxy)phenyl)-1-oxo-2-propenyl]amino]benzoic acid has an XRPD pattern comprising at least three peaks selected from 6.6, 11.7, 15.0, 15.9, 17.7, 18.7 and 19.2 degrees 2θ (±0.2 degrees 2θ). In some embodiments, crystalline Form I of the ethanolamine salt of (E)-2-[[3-(3-methoxy-4-propargyloxy)phenyl)-1-oxo-2-propenyl]amino]benzoic acid has an XRPD pattern comprising the peaks at 6.6, 11.7, 15.0, 15.9, 17.7, 18.7 and 19.2 degrees 2θ (±0.2 degrees 2θ). In some embodiments, crystalline Form I of the ethanolamine salt of (E)-2-[[3-(3-methoxy-4-propargyloxy)phenyl)-1-oxo-2-propenyl]amino]benzoic acid has an X-ray diffraction pattern substantially as shown in FIG. 1.

As will be understood by persons of skill in the art, because of the experimental variability when X-ray diffraction patterns are measured on different instruments, the peak positions are assumed to be equal if the two theta (2θ) values agree to within a certain degree of variability. For example, the United States Pharmacopeia states that if the angular setting of the 10 strongest diffraction peaks agree to within ±0.2 degrees with that of a reference material, and the relative intensities of the peaks do not vary by more than 20%, the identity is confirmed. Accordingly, in some embodiments, peak positions recited herein include variability within ±0.2 degrees 2θ.

In certain embodiments, the crystalline form of the ethanolamine salt of (E)-2-[[3-(3-methoxy-4-propargyloxy)phenyl)-1-oxo-2-propenyl]amino]benzoic acid comprises at least 80%, at least 85%, at least 88%, at least 90%, at least 91%, at least 92%, at least 93%, at least 94%, at least 95%, at least 96%, at least 97%, at least 98%, at least 99%, at least 99.5%, or at least 99.9% of crystalline Form I of the ethanolamine salt of (E)-2-[[3-(3-methoxy-4-propargyloxy)phenyl)-1-oxo-2-propenyl]amino]benzoic acid provided herein.

In certain embodiments, in a pharmaceutical composition comprising the ethanolamine salt of (E)-2-[[3-(3-methoxy-4-propargyloxy)phenyl)-1-oxo-2-propenyl]amino]benzoic acid, at least 80%, at least 85%, at least 88%, at least 90%, at least 91%, at least 92%, at least 93%, at least 94%, at least 95%, at least 96%, at least 97%, at least 98%, at least 99%, at least 99.5%, or at least 99.9% of the ethanolamine salt of (E)-2-[[3-(3-methoxy-4-propargyloxy)phenyl)-1-oxo-2-propenyl]amino]benzoic acid is crystalline Form I of the ethanolamine salt of (E)-2-[[3-(3-methoxy-4-propargyloxy)phenyl)-1-oxo-2-propenyl]amino]benzoic acid provided herein.

Figure 2:
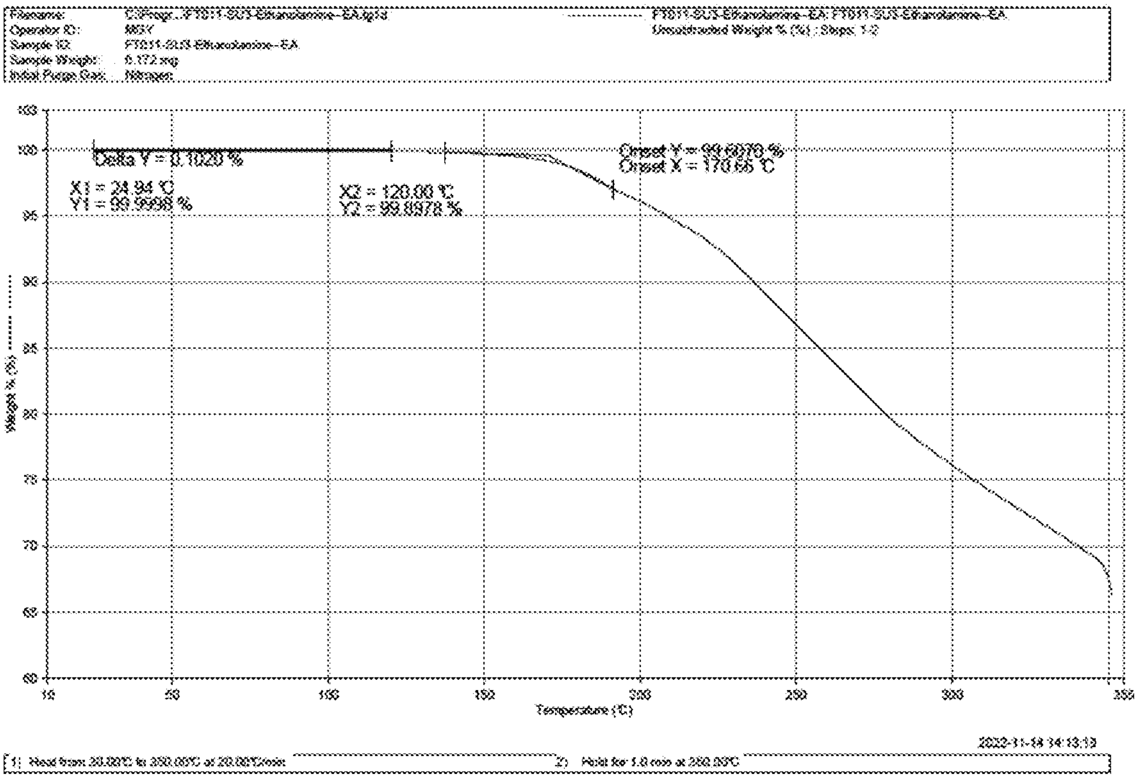
FIG. 2 shows an exemplary thermogravimetric analysis (TGA) thermogram of a sample of the ethanolamine salt of (E)-2-[[3-(3-methoxy-4-propargyloxy)phenyl)-1-oxo-2-propenyl]amino]benzoic acid.

In some embodiments, the solid form (e.g., crystalline form) of the ethanolamine salt of (E)-2-[[3-(3-methoxy-4-propargyloxy)phenyl)-1-oxo-2-propenyl]amino]benzoic acid provided herein has a thermogravimetric analysis (TGA) plot. In some embodiments, the solid form (e.g., crystalline form) of the ethanolamine salt of (E)-2-[[3-(3-methoxy-4-propargyloxy)phenyl)-1-oxo-2-propenyl]amino]benzoic acid exhibits a weight loss of less than 3%, less than 2.5%, less than 2%, less than 1.9%, less than 1.8%, less than 1.7%, less than 1.6%, less than 1.5%, less than 1.4%, less than 1.3%, less than 1.2%, less than 1.1%, less than 1.0%, less than 0.9%, less than 0.8%, less than 0.7%, less than 0.6%, less than 0.5%, less than 0.4%, less than 0.3%, less than 0.2%, or less than 0.15% when heated from about 25° C. to about 120° C. In some embodiments, the solid form (e.g., crystalline form) of the ethanolamine salt of (E)-2-[[3-(3-methoxy-4-propargyloxy)phenyl)-1-oxo-2-propenyl]amino]benzoic acid provided herein has a thermogravimetric analysis (TGA) plot. In some embodiments, the solid form (e.g., crystalline form) of the ethanolamine salt of (E)-2-[[3-(3-methoxy-4-propargyloxy)phenyl)-1-oxo-2-propenyl]amino]benzoic acid exhibits a weight loss of from 0.15% to 3% when heated from about 25° C. to about 120° C. In some embodiments, the solid form (e.g., crystalline form) of the ethanolamine salt of (E)-2-[[3-(3-methoxy-4-propargyloxy)phenyl)-1-oxo-2-propenyl]amino]benzoic acid exhibits a weight loss of 0.10% when heated from about 25° C. to about 120° C. In certain embodiments, the solid form (e.g., crystalline form) of the ethanolamine salt of (E)-2-[[3-(3-methoxy-4-propargyloxy)phenyl)-1-oxo-2-propenyl]amino]benzoic acid has a TGA plot substantially as shown in FIG. 2. The solid form (e.g., crystalline form) of the ethanolamine salt of (E)-2-[[3-(3-methoxy-4-propargyloxy)phenyl)-1-oxo-2-propenyl]amino]benzoic acid provided herein may therefore be characterized as being thermally stable.

Figure 4:
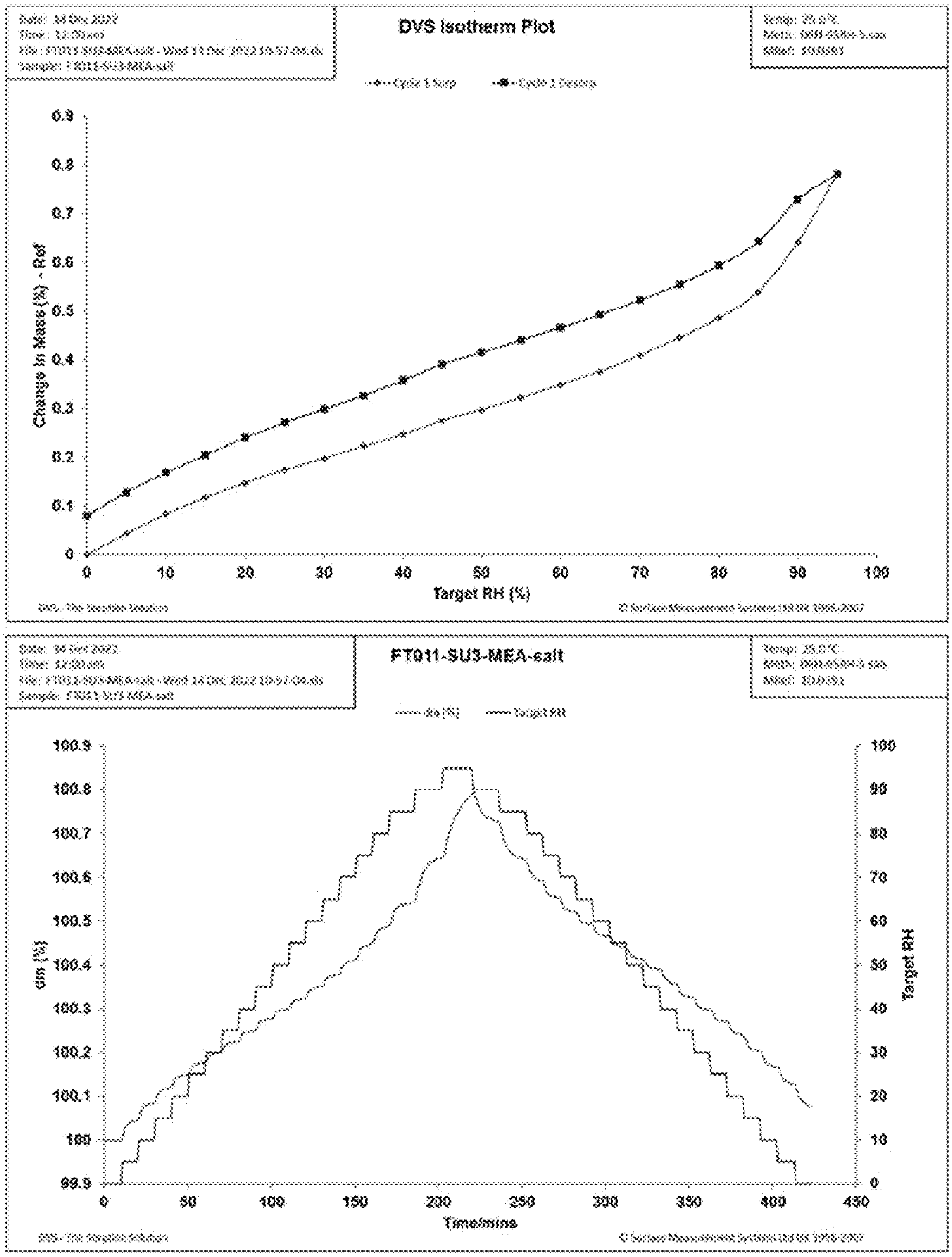
FIG. 4 shows an exemplary Dynamic Vapor Sorption (DVS) of a sample of the ethanolamine salt of (E)-2-[[3-(3-methoxy-4-propargyloxy)phenyl)-1-oxo-2-propenyl]amino]benzoic acid. DVS isotherm plot (top) and DVS change in mass plot (bottom) are shown.

In some embodiments, the solid form (e.g., crystalline form) of the ethanolamine salt of (E)-2-[[3-(3-methoxy-4-propargyloxy)phenyl)-1-oxo-2-propenyl]amino]benzoic acid provided herein has a dynamic vapor sorption (DVS) plot. In some embodiments, the solid form (e.g., crystalline form) of the ethanolamine salt of (E)-2-[[3-(3-methoxy-4-propargyloxy)phenyl)-1-oxo-2-propenyl]amino]benzoic acid exhibits a mass increase (e.g., water sorption) of less than 10%, less than 9%, less than 8%, less than 7%, less than 6%, less than 5%, less than 4%, less than 3%, less than 2%, less than 1.9%, less than 1.8%, less than 1.7%, less than 1.6%, less than 1.5%, less than 1.4%, less than 1.3%, less than 1.2%, less than 1.1%, less than 1%, less than 0.90%, less than 0.80%, less than 0.70%, less than 0.60%, or less than 0.55% when subjected to an increase in relative humidity from about 0% to about 80% relative humidity at 25° C. In some embodiments, the solid form (e.g., crystalline form) of the ethanolamine salt of (E)-2-[[3-(3-methoxy-4-propargyloxy)phenyl)-1-oxo-2-propenyl]amino]benzoic acid provided herein has a dynamic vapor sorption (DVS) plot. In some embodiments, the solid form (e.g., crystalline form) of the ethanolamine salt of (E)-2-[[3-(3-methoxy-4-propargyloxy)phenyl)-1-oxo-2-propenyl]amino]benzoic acid exhibits a mass increase (e.g., water sorption) of from 0.55% to 10% when subjected to an increase in relative humidity from about 0% to about 80% relative humidity at 25° C. In some embodiments, the solid form (e.g., crystalline form) of the ethanolamine salt of (E)-2-[[3-(3-methoxy-4-propargyloxy)phenyl)-1-oxo-2-propenyl]amino]benzoic acid exhibits a mass increase (e.g., water sorption) of about 0.49% when subjected to an increase in relative humidity from about 0% to about 80% relative humidity at 25° C. In certain embodiments, the solid form (e.g., crystalline form) of the ethanolamine salt of (E)-2-[[3-(3-methoxy-4-propargyloxy)phenyl)-1-oxo-2-propenyl]amino]benzoic acid exhibits a DVS plot substantially as shown in FIG. 4. The solid form (e.g., crystalline form) of the ethanolamine salt of (E)-2-[[3-(3-methoxy-4-propargyloxy)phenyl)-1-oxo-2-propenyl]amino]benzoic acid provided herein may therefore be characterized as having very low hygroscopicity and being stable over a wide range of humidity.

Figure 6:
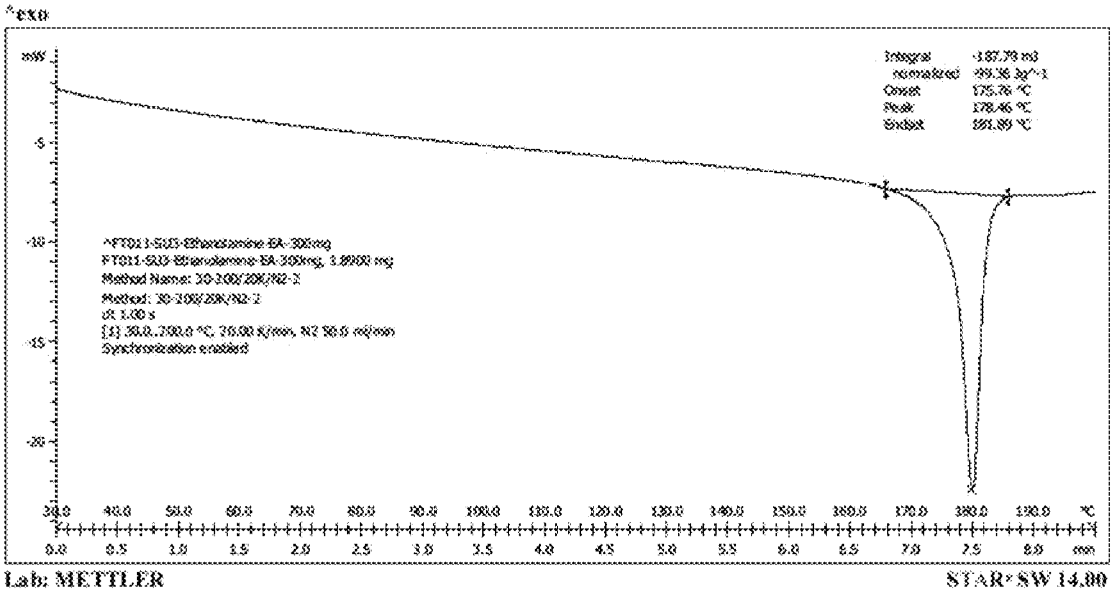
FIG. 6 shows an exemplary Differential Scanning calorimetry (DSC) diffractogram of a sample of the ethanolamine salt of (E)-2-[[3-(3-methoxy-4-propargyloxy)phenyl)-1-oxo-2-propenyl]amino]benzoic acid.

In some embodiments, the solid form (e.g., crystalline form) of the ethanolamine salt of (E)-2-[[3-(3-methoxy-4-propargyloxy)phenyl)-1-oxo-2-propenyl]amino]benzoic acid provided herein has a differential scanning calorimetric (DSC) thermogram. In some embodiments, the solid form (e.g., crystalline form) of the ethanolamine salt of (E)-2-[[3-(3-methoxy-4-propargyloxy)phenyl)-1-oxo-2-propenyl]amino]benzoic acid provided herein has a DSC thermogram comprising an endothermic event with onset temperature of about 176° C. and a peak at about 178° C. (melting point). In certain embodiments, the solid form (e.g., crystalline form) of the ethanolamine salt of (E)-2-[[3-(3-methoxy-4-propargyloxy)phenyl)-1-oxo-2-propenyl]amino]benzoic acid exhibits a DSC thermogram substantially as shown in FIG. 6. The solid form (e.g., crystalline form) of the ethanolamine salt of (E)-2-[[3-(3-methoxy-4-propargyloxy)phenyl)-1-oxo-2-propenyl]amino]benzoic acid provided herein may therefore be characterized as being thermally stable with a relatively high melting point.

In some embodiments, the ethanolamine salt of (E)-2-[[3-(3-methoxy-4-propargyloxy)phenyl)-1-oxo-2-propenyl]amino]benzoic acid or solid or crystalline forms thereof provided herein have a solubility of greater than 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml at 24 hours in FaSSIF media (pH 7.5). In some embodiments, the ethanolamine salt of (E)-2-[[3-(3-methoxy-4-propargyloxy)phenyl)-1-oxo-2-propenyl]amino]benzoic acid or solid or crystalline forms thereof provided herein have a solubility of greater than 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, or 10 mg/ml at 24 hours in FaSSIF media (pH 7.5). In some embodiments, the ethanolamine salt of (E)-2-[[3-(3-methoxy-4-propargyloxy)phenyl)-1-oxo-2-propenyl]amino]benzoic acid or solid or crystalline forms thereof provided herein have a solubility of greater than 7.99 mg/ml at 24 hours in FaSSIF media (pH 7.5).

In some embodiments, the ethanolamine salt of (E)-2-[[3-(3-methoxy-4-propargyloxy)phenyl)-1-oxo-2-propenyl]amino]benzoic acid or solid or crystalline forms thereof provided herein have a solubility of at least 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml at 24 hours in FeSSIF media (pH 7.8). In some embodiments, the ethanolamine salt of (E)-2-[[3-(3-methoxy-4-propargyloxy)phenyl)-1-oxo-2-propenyl]amino]benzoic acid or solid or crystalline forms thereof provided herein have a solubility of at least 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, or 10 mg/ml at 24 hours in FeSSIF media (pH 7.8). In some embodiments, the ethanolamine salt of (E)-2-[[3-(3-methoxy-4-propargyloxy)phenyl)-1-oxo-2-propenyl]amino]benzoic acid or solid or crystalline forms thereof provided herein have a solubility of greater than 8.02 mg/ml at 24 hours in FeSSIF media (pH 7.8).

In some embodiments, the ethanolamine salt of (E)-2-[[3-(3-methoxy-4-propargyloxy)phenyl)-1-oxo-2-propenyl]amino]benzoic acid or solid or crystalline forms thereof provided herein have a solubility of greater than 7.99 mg/ml at 24 hours in FaSSIF media (pH 7.5), and a solubility of greater than 8.02 mg/ml at 24 hours in FeSSIF media (pH 7.8).

In some embodiments, the ethanolamine salt of (E)-2-[[3-(3-methoxy-4-propargyloxy)phenyl)-1-oxo-2-propenyl]amino]benzoic acid or solid or crystalline forms thereof provided herein have a solubility of at least 0.04 mg/ml, 0.05 mg/ml, 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1 mg/ml at 24 hours in media at pH 6.8. In certain embodiments, the ethanolamine salt of (E)-2-[[3-(3-methoxy-4-propargyloxy) phenyl)-1-oxo-2-propenyl]amino]benzoic acid or solid or crystalline forms thereof provided herein have a solubility of at least 0.06 mg/ml at 24 hours in media at pH 6.8. In some embodiments, the ethanolamine salt of (E)-2-[[3-(3-methoxy-4-propargyloxy)phenyl)-1-oxo-2-propenyl]amino] benzoic acid or solid or crystalline forms thereof provided herein have a solubility of 0.088 mg/ml at 24 hours in media at pH 6.8.

In certain embodiments, the solid form (e.g., crystalline form) of the ethanolamine salt of (E)-2-[[3-(3-methoxy-4-propargyloxy)phenyl)-1-oxo-2-propenyl]amino]benzoic acid may be characterized by particle analysis. In yet another embodiment, a sample of the solid form (e.g., crystalline form) of the ethanolamine salt of (E)-2-[[3-(3-methoxy-4-propargyloxy)phenyl)-1-oxo-2-propenyl]amino]benzoic acid comprises particles of about 100, about 90, about 80, about 70, about 60, about 50, about 40, about 30, about 20, about 10, about 5 μM in length. In some embodiments, a sample of the solid form (e.g., crystalline form) of the ethanolamine salt of (E)-2-[[3-(3-methoxy-4-propargyloxy) phenyl)-1-oxo-2-propenyl]amino]benzoic acid comprises particles of about 100, about 70, about 60, about 40, about 20, about 10 UM in length.

In certain embodiments, the solid form (e.g., crystalline form) of the ethanolamine salt of (E)-2-[[3-(3-methoxy-4-propargyloxy)phenyl)-1-oxo-2-propenyl]amino]benzoic acid may contain no less than about 95%, no less than about 97%, no less than about 98%, no less than about 99%, or no less than about 99.5% by weight of the ethanolamine salt of (E)-2-[[3-(3-methoxy-4-propargyloxy)phenyl)-1-oxo-2-propenyl]amino]benzoic acid.

In certain embodiments, the ethanolamine salt of (E)-2-[[3-(3-methoxy-4-propargyloxy)phenyl)-1-oxo-2-propenyl] amino]benzoic acid or solid or crystalline forms thereof provided herein may contain no greater than about 0.1%, no greater than about 0.11%, no greater than about 0.12%, no greater than about 0.13%, no greater than about 0.14%, no greater than about 0.15%, no greater than about 0.16%, no greater than about 0.17%, no greater than about 0.18%, no greater than about 0.19%, no greater than about 0.2%, no greater than about 0.21%, no greater than about 0.22%, no greater than about 0.23%, no greater than about 0.24%, no greater than about 0.25%, no greater than about 0.26%, no greater than about 0.27%, no greater than about 0.28%, no greater than about 0.29%, no greater than about 0.3%, no greater than about 0.31%, no greater than about 0.32%, no greater than about 0.33%, no greater than about 0.34%, no greater than about 0.35%, no greater than about 0.36%, no greater than about 0.37%, no greater than about 0.38%, no greater than about 0.39%, no greater than about 0.4%, no greater than about 0.5%, no greater than about 0.6%, no greater than about 0.7%, no greater than about 0.8%, no greater than about 0.9%, no greater than about 1%, no greater than about 2%, no greater than about 3%, no greater than about 4%, no greater than about 5%, no greater than about 6%, no greater than about 7%, no greater than about 8%, no greater than about 9%, no greater than about 10%, no greater than about 11%, no greater than about 12%, no greater than about 13%, no greater than about 14%, no greater than about 15%, no greater than about 16%, no greater than about 17%, no greater than about 18%, no greater than about 19%, or no greater than about 20% water by weight.

In embodiments, the ethanolamine salt of (E)-2-[[3-(3-methoxy-4-propargyloxy)phenyl)-1-oxo-2-propenyl]amino] benzoic acid or solid or crystalline forms thereof provided herein exhibit superior pharmacokinetic properties compared to the free form of (E)-2-[[3-(3-methoxy-4-propargyloxy)phenyl)-1-oxo-2-propenyl]amino]benzoic acid, or compared to other pharmaceutically acceptable salts of (E)-2-[[3-(3-methoxy-4-propargyloxy)phenyl)-1-oxo-2-propenyl]amino]benzoic acid.

In some embodiments, the ethanolamine salt of (E)-2-[[3-(3-methoxy-4-propargyloxy)phenyl)-1-oxo-2-propenyl] amino]benzoic acid or solid or crystalline forms thereof provided herein have a bioavailability of at least 50 F %, 55 F %, 60 F %, 65 F %, 70 F %, 75 F %, 80 F %, 85 F %, 90 F %, 95 F %, or 99 F %. In some embodiments, the ethanolamine salt of (E)-2-[[3-(3-methoxy-4-propargyloxy) phenyl)-1-oxo-2-propenyl]amino]benzoic acid or solid or crystalline forms thereof provided herein have a bioavailability of about 70 F %, about 72 F %, about 74 F %, about 76 F %, about 78 F %, about 80 F %, about 81 F %, about 82 F %, about 83 F %, about 84 F %, about 85 F %, about 86 F %, about 87 F %, about 88 F %, about 89 F %, about 90 F %, about 92 F %, about 94 F %, about 96 F %, or about 98 F %. In some embodiments, the bioavailability is oral bioavailability.

In some embodiments, the ethanolamine salt of (E)-2-[[3-(3-methoxy-4-propargyloxy)phenyl)-1-oxo-2-propenyl] amino]benzoic acid or solid or crystalline forms thereof provided herein exhibit improved bioavailability compared to the free form of (E)-2-[[3-(3-methoxy-4-propargyloxy) phenyl)-1-oxo-2-propenyl]amino]benzoic acid. Unexpectedly, the present inventors found that bioavailability of the ethanolamine salt of (E)-2-[[3-(3-methoxy-4-propargyloxy) phenyl)-1-oxo-2-propenyl]amino]benzoic acid or solid or crystalline forms thereof provided herein is advantageously improved by at least about 1.1×, about 1.2×, about 1.3×, about 1.4×, about 1.5×, about 1.6×, about 1.7×, about 1.8×, about 1.9×, about 2.0×, about 2.1×, about 2.2×, about 2.3×, about 2.4×, about 2.5×, about 2.6×, about 2.7×, about 2.8×, about 2.9×, or about 3.0× compared to bioavailability of the free form of (E)-2-[[3-(3-methoxy-4-propargyloxy)phenyl)-1-oxo-2-propenyl]amino]benzoic acid. In certain embodiments, bioavailability of the ethanolamine salt of (E)-2-[[3-(3-methoxy-4-propargyloxy)phenyl)-1-oxo-2-propenyl] amino]benzoic acid or solid or crystalline forms thereof provided herein is improved by about 2.3× compared to bioavailability of the free form of (E)-2-[[3-(3-methoxy-4-propargyloxy)phenyl)-1-oxo-2-propenyl]amino]benzoic acid. In some embodiments, the bioavailability is oral bioavailability.

In some embodiments, the ethanolamine salt of (E)-2-[[3-(3-methoxy-4-propargyloxy)phenyl)-1-oxo-2-propenyl] amino]benzoic acid or solid or crystalline forms thereof provided herein provide improved bioavailability compared to other pharmaceutically acceptable salts of (E)-2-[[3-(3-methoxy-4-propargyloxy)phenyl)-1-oxo-2-propenyl]amino] benzoic acid. Surprisingly, the present inventors found that the ethanolamine salt of (E)-2-[[3-(3-methoxy-4-propargyloxy)phenyl)-1-oxo-2-propenyl]amino]benzoic acid or solid or crystalline forms thereof provided herein advantageously exhibited superior bioavailability compared to other salts of (E)-2-[[3-(3-methoxy-4-propargyloxy)phenyl)-1-oxo-2-propenyl]amino]benzoic acid including the potassium (I) salt, meglumine salt, tris(hydroxymethyl)aminomethane ('Tris') salt, tert-butylamine salt, ammonium salt, and lysine salt of (E)-2-[[3-(3-methoxy-4-propargyloxy)phenyl)-1-oxo-2-propenyl]amino]benzoic acid.

The superior bioavailability of the ethanolamine salt of (E)-2-[[3-(3-methoxy-4-propargyloxy)phenyl)-1-oxo-2-propenyl]amino]benzoic acid or solid or crystalline forms thereof provided herein relative to the free form of (E)-2-[[3-(3-methoxy-4-propargyloxy)phenyl)-1-oxo-2-propenyl] amino]benzoic acid as well as to the other tested salts, in particular other amino salts of (E)-2-[[3-(3-methoxy-4-propargyloxy)phenyl)-1-oxo-2-propenyl]amino]benzoic acid, could not have been predicted, and may provide distinct advantages such as enhanced therapeutic effect, reduction in dose, reduction in dosage frequency, reduction in undesirable side effects, and improved patient compliance.

tert-Butylamine Salt of (E)-2-[[3-(3-methoxy-4-propargyloxy)phenyl)-1-oxo-2-propenyl]amino]benzoic acid, and Solid or Crystalline Forms Thereof In embodiments, provided herein is the tert-butylamine salt of (E)-2-[[3-(3-methoxy-4-propargyloxy)phenyl)-1-oxo-2-propenyl]amino]benzoic acid, including solid and crystalline forms thereof.

In embodiments, provided herein is a solid form of the tert-butylamine salt of (E)-2-[[3-(3-methoxy-4-propargyloxy)phenyl)-1-oxo-2-propenyl]amino]benzoic acid.

In some embodiments, provided herein is a crystalline form of the tert-butylamine salt of (E)-2-[[3-(3-methoxy-4-propargyloxy)phenyl)-1-oxo-2-propenyl]amino]benzoic acid.

In some embodiments, the crystalline form of the tert-butylamine salt of (E)-2-[[3-(3-methoxy-4-propargyloxy) phenyl)-1-oxo-2-propenyl]amino]benzoic acid provided herein is crystalline Form II.

Figure 8:
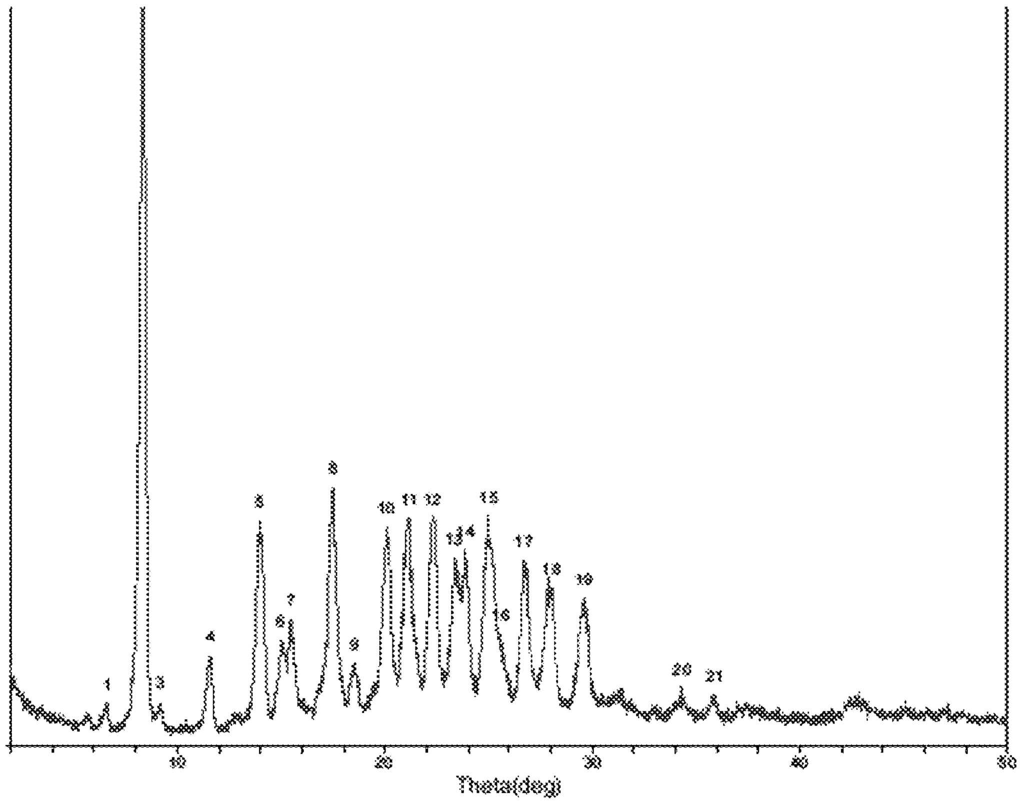
FIG. 8 shows an exemplary X-Ray Powder Diffraction (XRPD) pattern of a sample of the tert-butylamine salt of (E)-2-[[3-(3-methoxy-4-propargyloxy)phenyl)-1-oxo-2-propenyl]amino]benzoic acid in crystalline Form II.

In some embodiments, crystalline Form II of the tert-butylamine salt of (E)-2-[[3-(3-methoxy-4-propargyloxy) phenyl)-1-oxo-2-propenyl]amino]benzoic acid has an X-ray powder diffraction (XRPD) pattern. FIG. 8 depicts an example of an XRPD pattern for crystalline Form II. In some embodiments, XRPD pattern of the crystalline Form II of the tert-butylamine salt of (E)-2-[[3-(3-methoxy-4-propargyloxy)phenyl)-1-oxo-2-propenyl]amino]benzoic acid includes at least one diffraction peak selected from 8.36, 13.96, and 17.50 degrees 2θ (±0.2 degrees 2θ). In some embodiments, crystalline Form II of the tert-butylamine salt of (E)-2-[[3-(3-methoxy-4-propargyloxy)phenyl)-1-oxo-2-propenyl]amino]benzoic acid has an XRPD pattern comprising at least two peaks selected from 8.36, 13.96, and 17.50 degrees 2θ (±0.2 degrees 2θ). In some embodiments, crystalline Form II of the tert-butylamine salt of (E)-2-[[3-(3-methoxy-4-propargyloxy)phenyl)-1-oxo-2-propenyl] amino]benzoic acid has an XRPD pattern comprising the peaks at 8.36, 13.96, and 17.50 degrees 2θ (±0.2 degrees 2θ). In some embodiments, crystalline Form II of the tert-butylamine salt of (E)-2-[[3-(3-methoxy-4-propargyloxy)phenyl)-1-oxo-2-propenyl]amino]benzoic acid has an X-ray diffraction pattern substantially as shown in FIG. 8.

In certain embodiments, the crystalline form of the tert-butylamine salt of (E)-2-[[3-(3-methoxy-4-propargyloxy) phenyl)-1-oxo-2-propenyl]amino]benzoic acid comprises at least 80%, at least 85%, at least 88%, at least 90%, at least 91%, at least 92%, at least 93%, at least 94%, at least 95%, at least 96%, at least 97%, at least 98%, at least 99%, at least 99.5%, or at least 99.9% of crystalline Form II of the tert-butylamine salt of (E)-2-[[3-(3-methoxy-4-propargyloxy)phenyl)-1-oxo-2-propenyl]amino]benzoic acid provided herein.

In certain embodiments, in a composition comprising the tert-butylamine salt of (E)-2-[[3-(3-methoxy-4-propargyloxy)phenyl)-1-oxo-2-propenyl]amino]benzoic acid, at least 80%, at least 85%, at least 88%, at least 90%, at least 91%, at least 92%, at least 93%, at least 94%, at least 95%, at least 96%, at least 97%, at least 98%, at least 99%, at least 99.5%, or at least 99.9% of the tert-butylamine salt of (E)-2-[[3-(3-methoxy-4-propargyloxy)phenyl)-1-oxo-2-propenyl]amino] benzoic acid is crystalline Form II of the tert-butylamine salt of (E)-2-[[3-(3-methoxy-4-propargyloxy)phenyl)-1-oxo-2-propenyl]amino]benzoic acid provided herein.

Figure 3:
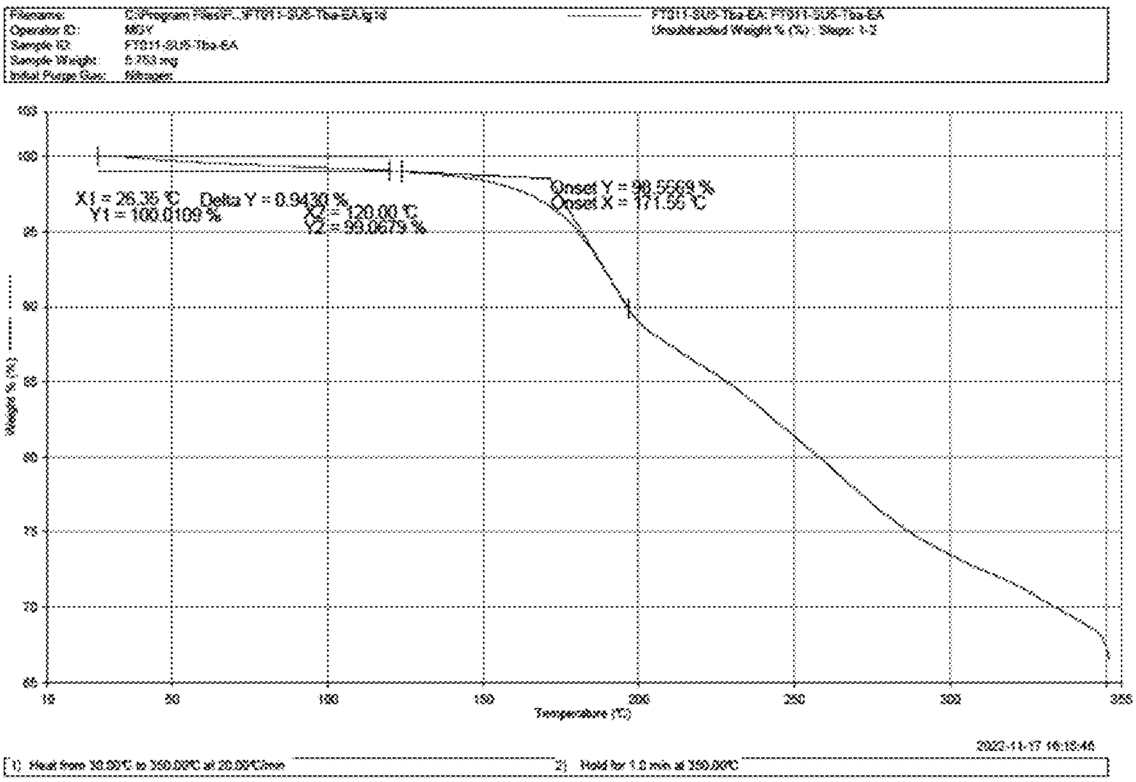
FIG. 3 shows an exemplary thermogravimetric analysis (TGA) thermogram of a sample of the tert-butylamine salt of (E)-2-[[3-(3-methoxy-4-propargyloxy)phenyl)-1-oxo-2-propenyl]amino]benzoic acid.

In some embodiments, the solid form (e.g., crystalline form) of the tert-butylamine salt of (E)-2-[[3-(3-methoxy-4-propargyloxy)phenyl)-1-oxo-2-propenyl]amino]benzoic acid provided herein has a thermogravimetric analysis (TGA) plot. In some embodiments, the solid form (e.g., crystalline form) of the tert-butylamine salt of (E)-2-[[3-(3-methoxy-4-propargyloxy)phenyl)-1-oxo-2-propenyl]amino] benzoic acid exhibits a weight loss of less than 3%, less than 2.5%, less than 2%, less than 1.9%, less than 1.8%, less than 1.7%, less than 1.6%, less than 1.5%, less than 1.4%, less than 1.3%, less than 1.2%, less than 1.1%, less than 1.0%, less than 0.9%, less than 0.8%, less than 0.7%, less than 0.6%, less than 0.5%, less than 0.4%, less than 0.3%, less than 0.2%, or less than 0.15% as determined by thermogravimetric analysis when heated from about 25° C. to about 120° C. In some embodiments, the solid form (e.g., crystalline form) of the tert-butylamine salt of (E)-2-[[3-(3-methoxy-4-propargyloxy)phenyl)-1-oxo-2-propenyl]amino] benzoic acid exhibits a weight loss of from 0.15% to 3% as measured by TGA when heated from about 25° C. to about 120° C. In some embodiments, the solid form (e.g., crystalline form) of the tert-butylamine salt of (E)-2-[[3-(3-methoxy-4-propargyloxy)phenyl)-1-oxo-2-propenyl]amino] benzoic acid exhibits a weight loss of 0.94% as determined by thermogravimetric analysis when heated from about 25° C. to about 120° C. In certain embodiments, the solid form (e.g., crystalline form) of the tert-butylamine salt of (E)-2-[[3-(3-methoxy-4-propargyloxy)phenyl)-1-oxo-2-propenyl] amino]benzoic acid has a TGA plot substantially as shown in FIG. 3. The solid form (e.g., crystalline form) of the tert-butylamine salt of (E)-2-[[3-(3-methoxy-4-propargyloxy)phenyl)-1-oxo-2-propenyl]amino]benzoic acid provided herein may therefore be characterized as being thermally stable.

Figure 5:
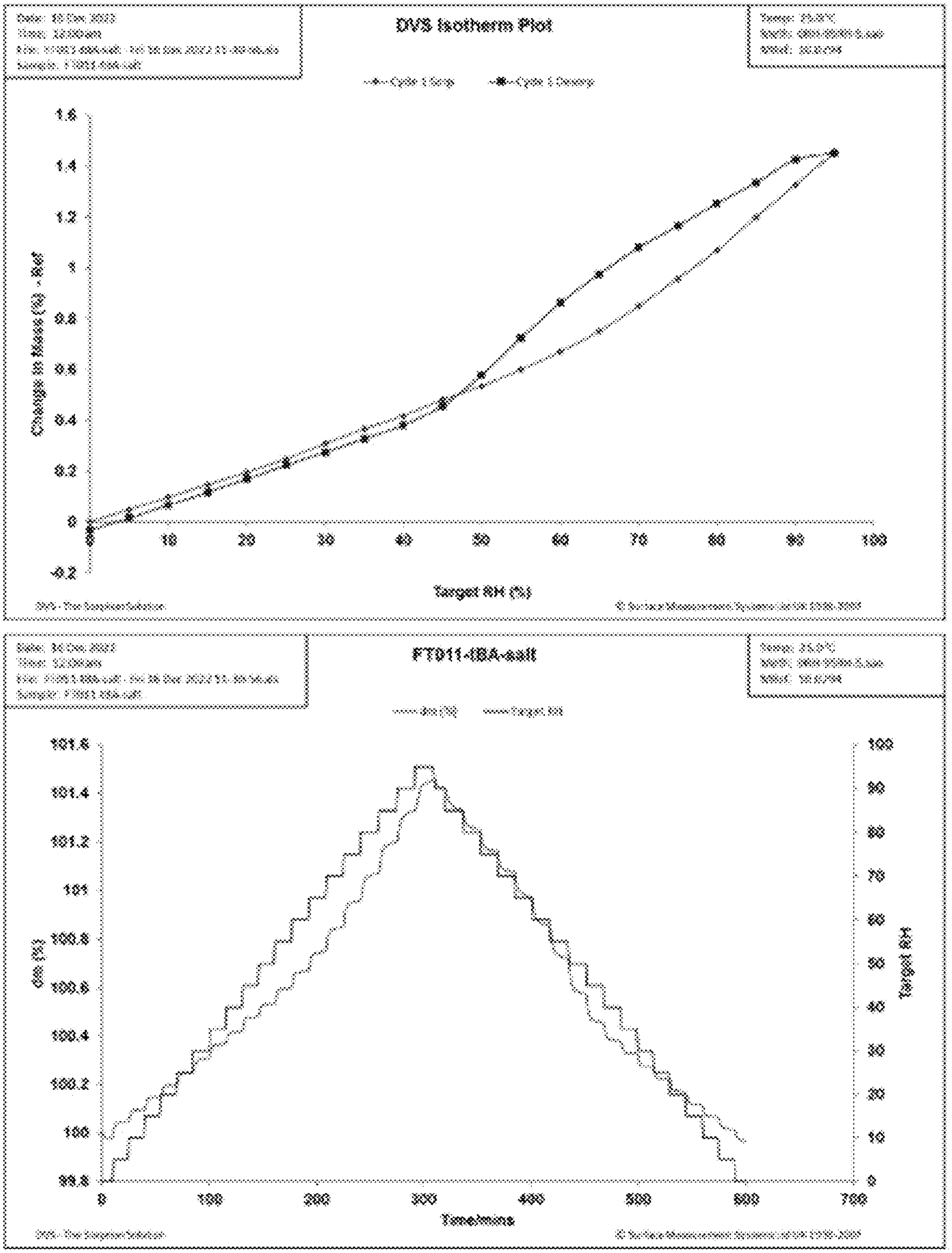
FIG. 5 shows an exemplary Dynamic Vapor Sorption (DVS) of a sample of the tert-butylamine salt of (E)-2-[[3-(3-methoxy-4-propargyloxy)phenyl)-1-oxo-2-propenyl]amino]benzoic acid. DVS isotherm plot (top) and DVS change in mass plot (bottom) are shown.

In some embodiments, the solid form (e.g., crystalline form) of the tert-butylamine salt of (E)-2-[[3-(3-methoxy-4-propargyloxy)phenyl)-1-oxo-2-propenyl]amino]benzoic acid provided herein has a dynamic vapor sorption (DVS) plot. In some embodiments, the solid form (e.g., crystalline form) of the tert-butylamine salt of (E)-2-[[3-(3-methoxy-4-propargyloxy)phenyl)-1-oxo-2-propenyl]amino]benzoic acid exhibits a mass increase (e.g., water sorption) of less than 10%, less than 9%, less than 8%, less than 7%, less than 6%, less than 5%, less than 4%, less than 3%, less than 2%, less than 1.9%, less than 1.8%, less than 1.7%, less than 1.6%, less than 1.5%, less than 1.4%, less than 1.3%, or less than 1.2% when subjected to an increase in relative humidity from about 0% to about 80% relative humidity at 25° C. In some embodiments, the solid form (e.g., crystalline form) of the tert-butylamine salt of (E)-2-[[3-(3-methoxy-4-propargyloxy)phenyl)-1-oxo-2-propenyl]amino]benzoic acid exhibits a mass increase (e.g., water sorption) of from 1.2% to 10% when subjected to an increase in relative humidity from about 0% to about 80% relative humidity at 25° C. In some embodiments, the solid form (e.g., crystalline form) of the tert-butylamine salt of (E)-2-[[3-(3-methoxy-4-propargyloxy)phenyl)-1-oxo-2-propenyl]amino]benzoic acid exhibits a mass increase (e.g., water sorption) of about 1.07% when subjected to an increase in relative humidity from about 0% to about 80% relative humidity at 25° C. In certain embodiments, the solid form (e.g., crystalline form) of the tert-butylamine salt of (E)-2-[[3-(3-methoxy-4-propargyloxy)phenyl)-1-oxo-2-propenyl]amino]benzoic acid exhibits a DVS plot substantially as shown in FIG. 5. The solid form (e.g., crystalline form) of the tert-butylamine salt of (E)-2-[[3-(3-methoxy-4-propargyloxy)phenyl)-1-oxo-2-propenyl]amino]benzoic acid provided herein may therefore be characterized as having very low hygroscopicity and being stable over a wide range of humidity.

Figure 7:
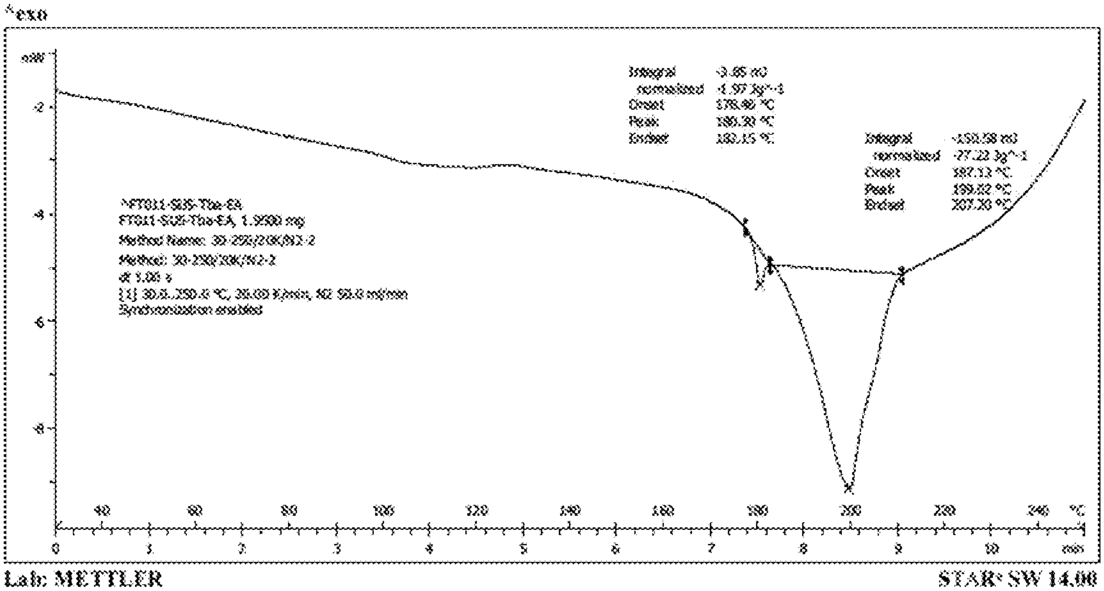
FIG. 7 shows an exemplary Differential Scanning calorimetry (DSC) diffractogram of a sample of the tert-butylamine salt of (E)-2-[[3-(3-methoxy-4-propargyloxy)phenyl)-1-oxo-2-propenyl]amino]benzoic acid.

In some embodiments, the solid form (e.g., crystalline form) of the tert-butylamine salt of (E)-2-[[3-(3-methoxy-4-propargyloxy)phenyl)-1-oxo-2-propenyl]amino]benzoic acid provided herein has a differential scanning calorimetric (DSC) thermogram. In some embodiments, the solid form (e.g., crystalline form) of the tert-butylamine salt of (E)-2-[[3-(3-methoxy-4-propargyloxy)phenyl)-1-oxo-2-propenyl]amino]benzoic acid provided herein has a DSC thermogram comprising an endothermic event with an onset temperature of about 175° C. and a peak at about 180° C.; and another endothermic event with an onset temperature of about 187° C. and a peak at about 199° C. In certain embodiments, the solid form (e.g., crystalline form) of the tert-butylamine salt of (E)-2-[[3-(3-methoxy-4-propargyloxy)phenyl)-1-oxo-2-propenyl]amino]benzoic acid exhibits a DSC thermogram substantially as shown in FIG. 7. The solid form (e.g., crystalline form) of the tert-butylamine salt of (E)-2-[[3-(3-methoxy-4-propargyloxy)phenyl)-1-oxo-2-propenyl]amino]benzoic acid provided herein may therefore be characterized as having good thermal stability.

In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of greater than 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml at 24 hours in FaSSIF media (pH 7.5). In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of greater than 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, or 10 mg/ml at 24 hours in FaSSIF media (pH 7.5). In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of greater than 2.52 mg/ml at 24 hours in FaSSIF media (pH 7.5).

In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of at least 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, or 20 mg/ml at 24 hours in FeSSIF media (pH 7.8). In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of at least 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, or 10 mg/ml at 24 hours in FeSSIF media (pH 7.8). In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of greater than 3.42 mg/ml at 24 hours in FeSSIF media (pH 7.8).

In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of greater than 2.52 mg/ml at 24 hours in FaSSIF media (pH 7.5), and a solubility of greater than 3.42 mg/ml at 24 hours in FeSSIF media (pH 7.8).

In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of at least 0.04 mg/ml, 0.05 mg/ml, 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1 mg/ml at 24 hours in media at pH 6.8. In certain embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of at least 0.07 mg/ml at 24 hours in media at pH 6.8. In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a solubility of 0.071 mg/ml at 24 hours in media at pH 6.8.

In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a bioavailability of at least 50 F %, 55 F %, 60 F %, 65 F %, 70 F %, 75 F %, 80 F %, 85 F %, 90 F %, 95 F %, or 99 F %. In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a bioavailability of about 60 F %. In some embodiments, the tert-butylamine salt of (E)-2-[[3-(3-methoxy-4-propargyloxy)phenyl)-1-oxo-2-propenyl]amino]benzoic acid or solid or crystalline forms thereof provided herein have a bioavailability of 59 F %. In some embodiments, the bioavailability is oral bioavailability.

Meglumine Salt of (E)-2-[[3-(3-methoxy-4-propargyloxy)phenyl)-1-oxo-2-propenyl]amino]benzoic acid, and Solid or Crystalline Forms Thereof In embodiments, provided herein is the meglumine salt of (E)-2-[[3-(3-methoxy-4-propargyloxy)phenyl)-1-oxo-2-propenyl]amino]benzoic acid, including solid and crystalline forms thereof.

In embodiments, provided herein is a solid form of the meglumine salt of (E)-2-[[3-(3-methoxy-4-propargyloxy)phenyl)-1-oxo-2-propenyl]amino]benzoic acid.

In some embodiments, provided herein is a crystalline form of the meglumine salt of (E)-2-[[3-(3-methoxy-4-propargyloxy)phenyl)-1-oxo-2-propenyl]amino]benzoic acid.

In some embodiments, the crystalline form of the meglumine salt of (E)-2-[[3-(3-methoxy-4-propargyloxy)phenyl)-1-oxo-2-propenyl]amino]benzoic acid provided herein is crystalline Form III.

Figure 9:
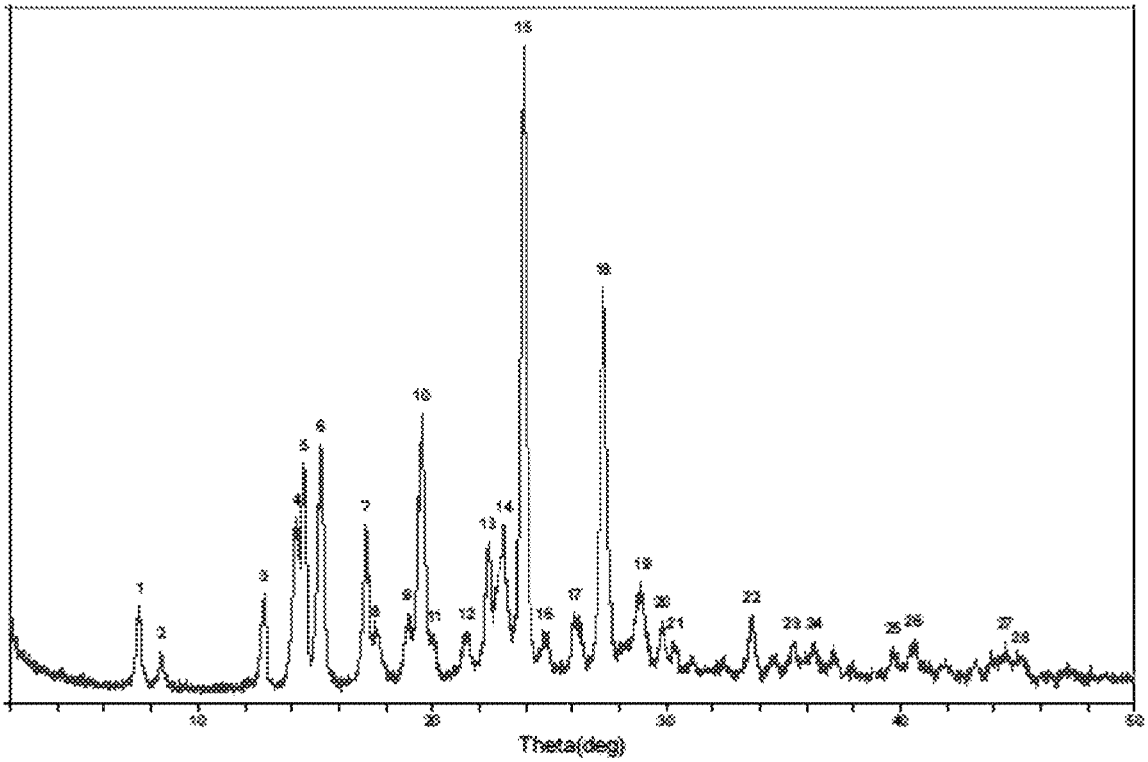
FIG. 9 shows an exemplary X-Ray Powder Diffraction (XRPD) pattern of a sample of the meglumine salt of (E)-2-[[3-(3-methoxy-4-propargyloxy)phenyl)-1-oxo-2-propenyl]amino]benzoic acid in crystalline Form III.

In some embodiments, crystalline Form III of the meglumine salt of (E)-2-[[3-(3-methoxy-4-propargyloxy)phenyl)-1-oxo-2-propenyl]amino]benzoic acid has an X-ray powder diffraction (XRPD) pattern. FIG. 9 depicts an example of an XRPD pattern for crystalline Form III. In some embodiments, XRPD pattern of the crystalline Form III of the meglumine salt of (E)-2-[[3-(3-methoxy-4-propargyloxy) phenyl)-1-oxo-2-propenyl]amino]benzoic acid includes at least one diffraction peak selected from 6.6, 11.7, 15.9, 17.7, 23.7, and 26.6 degrees 2θ (±0.2 degrees 2θ). In some embodiments, crystalline Form III of the meglumine salt of (E)-2-[[3-(3-methoxy-4-propargyloxy)phenyl)-1-oxo-2-propenyl]amino]benzoic acid has an XRPD pattern comprising at least two peaks selected from 6.6, 11.7, 15.9, 17.7, 23.7, and 26.6 degrees 2θ (±0.2 degrees 2θ). In some embodiments, crystalline Form III of the meglumine salt of (E)-2-[[3-(3-methoxy-4-propargyloxy)phenyl)-1-oxo-2-propenyl]amino]benzoic acid has an XRPD pattern comprising at least three peaks selected from 6.6, 11.7, 15.9, 17.7, 23.7, and 26.6 degrees 2θ (±0.2 degrees 2θ). In some embodiments, crystalline Form III of the meglumine salt of (E)-2-[[3-(3-methoxy-4-propargyloxy)phenyl)-1-oxo-2-propenyl]amino]benzoic acid has an XRPD pattern comprising the peaks at 6.6, 11.7, 15.9, and 17.7 degrees 2θ (±0.2 degrees 2θ). In some embodiments, crystalline Form III of the meglumine salt of (E)-2-[[3-(3-methoxy-4-propargyloxy)phenyl)-1-oxo-2-propenyl]amino]benzoic acid has an X-ray diffraction pattern substantially as shown in FIG. 9.

Tris(hydroxymethyl)aminomethane (Tris) Salt of (E)-2-[[3-(3-methoxy-4-propargyloxy)phenyl)-1-oxo-2-propenyl]amino]benzoic acid, and Solid or Crystalline Forms Thereof In embodiments, provided herein is the tris(hydroxymethyl)aminomethane salt of (E)-2-[[3-(3-methoxy-4-propargyloxy)phenyl)-1-oxo-2-propenyl]amino]benzoic acid, including solid and crystalline forms thereof.

In embodiments, provided herein is a solid form of the tris(hydroxymethyl)aminomethane salt of (E)-2-[[3-(3-methoxy-4-propargyloxy)phenyl)-1-oxo-2-propenyl]amino] benzoic acid.

In some embodiments, provided herein is a crystalline form of the tris(hydroxymethyl)aminomethane salt of (E)-2-[[3-(3-methoxy-4-propargyloxy)phenyl)-1-oxo-2-propenyl]amino]benzoic acid.

In some embodiments, the crystalline form of the tris (hydroxymethyl)aminomethane salt of (E)-2-[[3-(3-methoxy-4-propargyloxy)phenyl)-1-oxo-2-propenyl]amino] benzoic acid provided herein is crystalline Form IV.

Figure 10:
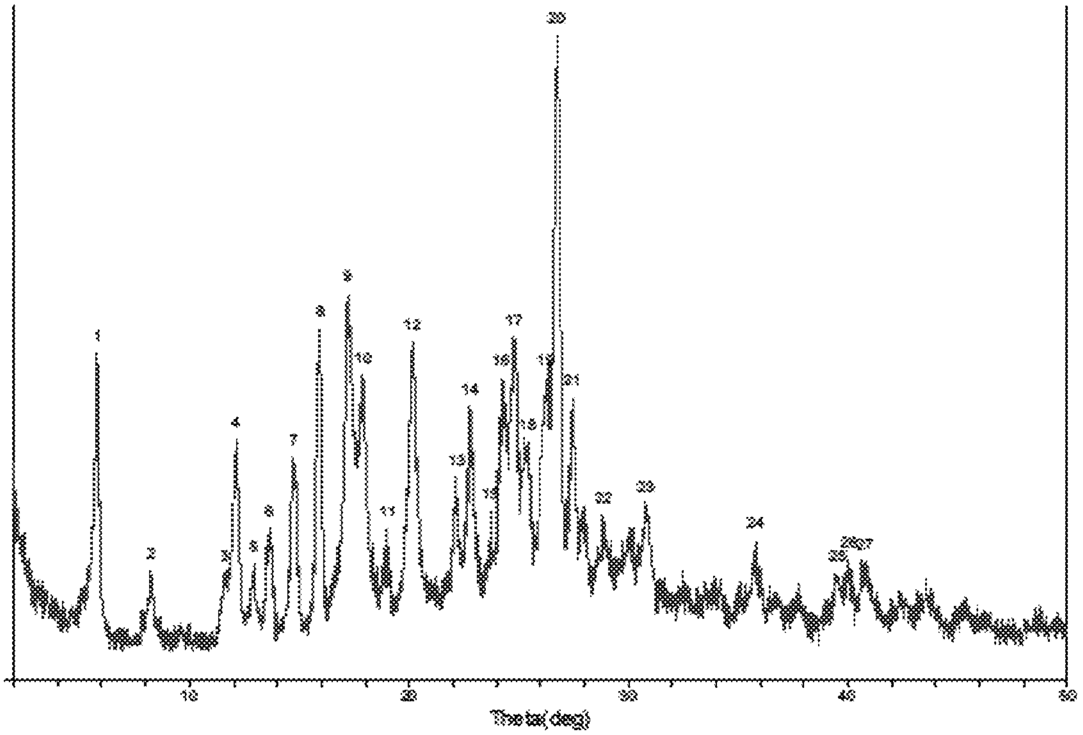
FIG. 10 shows an exemplary X-Ray Powder Diffraction (XRPD) pattern of a sample of the tris(hydroxymethyl)aminomethane (Tris) salt of (E)-2-[[3-(3-methoxy-4-propargyloxy)phenyl)-1-oxo-2-propenyl]amino]benzoic acid in crystalline Form IV.

In some embodiments, crystalline Form IV of the tris (hydroxymethyl)aminomethane salt of (E)-2-[[3-(3-methoxy-4-propargyloxy)phenyl)-1-oxo-2-propenyl]amino] benzoic acid has an X-ray powder diffraction (XRPD) pattern. FIG. 10 depicts an example of an XRPD pattern for crystalline Form IV. In some embodiments, XRPD pattern of the crystalline Form IV of the tris(hydroxymethyl)aminomethane salt of (E)-2-[[3-(3-methoxy-4-propargyloxy) phenyl)-1-oxo-2-propenyl]amino]benzoic acid includes at least one diffraction peak selected from 5.78, 12.18, 15.94, and 17.24 degrees 2θ (±0.2 degrees 2θ). In some embodiments, crystalline Form IV of the tris(hydroxymethyl)aminomethane salt of (E)-2-[[3-(3-methoxy-4-propargyloxy) phenyl)-1-oxo-2-propenyl]amino]benzoic acid has an XRPD pattern comprising at least two peaks selected from 5.78, 12.18, 15.94, and 17.24 degrees 2θ (±0.2 degrees 2θ). In some embodiments, crystalline Form IV of the tris (hydroxymethyl)aminomethane salt of (E)-2-[[3-(3-methoxy-4-propargyloxy)phenyl)-1-oxo-2-propenyl]amino] benzoic acid has an XRPD pattern comprising at least three peaks selected from 5.78, 12.18, 15.94, and 17.24 degrees 2θ (±0.2 degrees 2θ). In some embodiments, crystalline Form IV of the tris(hydroxymethyl)aminomethane salt of (E)-2-[[3-(3-methoxy-4-propargyloxy)phenyl)-1-oxo-2-propenyl]amino]benzoic acid has an XRPD pattern comprising the peaks at 5.78, 12.18, 15.94, and 17.24 degrees 2θ (±0.2 degrees 2θ). In some embodiments, crystalline Form IV of the tris(hydroxymethyl)aminomethane salt of (E)-2-[[3-(3-methoxy-4-propargyloxy)phenyl)-1-oxo-2-propenyl] amino]benzoic acid has an X-ray diffraction pattern substantially as shown in FIG. 10.

Potassium Salt of (E)-2-[[3-(3-methoxy-4-propargyloxy)phenyl)-1-oxo-2-propenyl]amino]benzoic acid, and Solid or Crystalline Forms Thereof In embodiments, provided herein is the potassium salt of (E)-2-[[3-(3-methoxy-4-propargyloxy)phenyl)-1-oxo-2-propenyl]amino]benzoic acid, including solid and crystalline forms thereof.

In embodiments, provided herein is a solid form of the potassium salt of (E)-2-[[3-(3-methoxy-4-propargyloxy) phenyl)-1-oxo-2-propenyl]amino]benzoic acid.

In some embodiments, provided herein is a crystalline form of the potassium salt of (E)-2-[[3-(3-methoxy-4-propargyloxy)phenyl)-1-oxo-2-propenyl]amino]benzoic acid.

In some embodiments, the crystalline form of the potassium salt of (E)-2-[[3-(3-methoxy-4-propargyloxy)phenyl)-1-oxo-2-propenyl]amino]benzoic acid provided herein is crystalline Form V.

Figure 11:
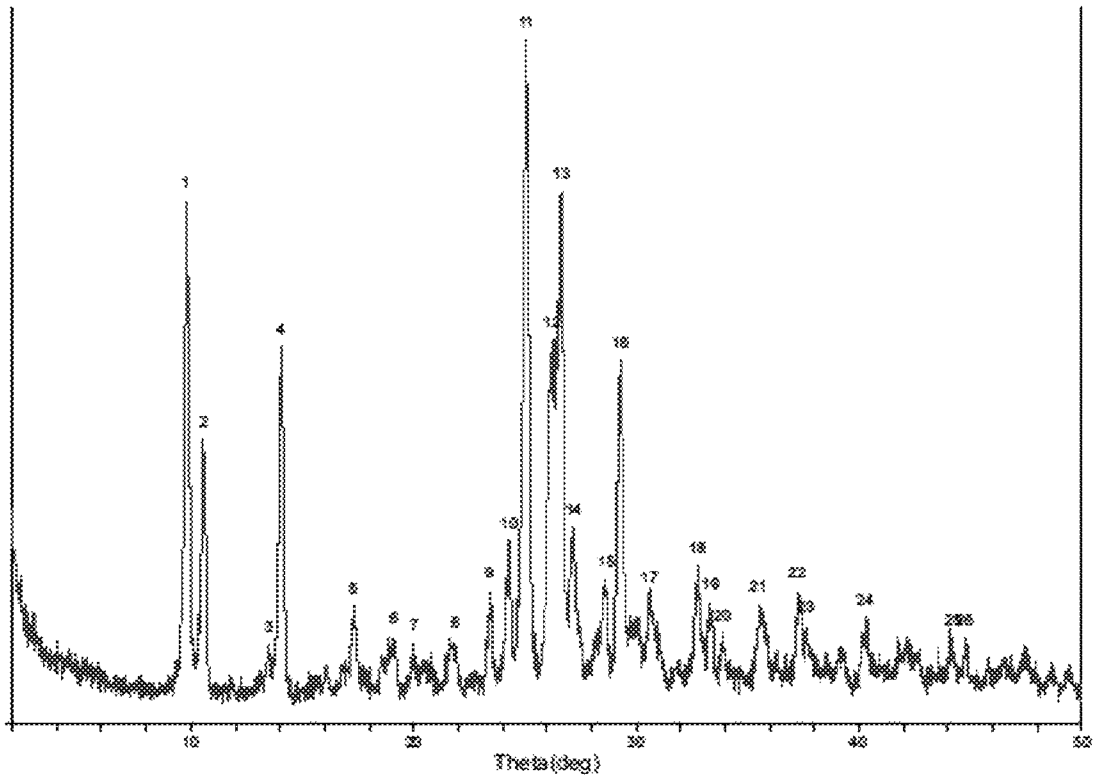
FIG. 11 shows an exemplary X-Ray Powder Diffraction (XRPD) pattern of a sample of the potassium salt of (E)-2-[[3-(3-methoxy-4-propargyloxy)phenyl)-1-oxo-2-propenyl]amino]benzoic acid in crystalline Form V.

In some embodiments, crystalline Form V of the potassium salt of (E)-2-[[3-(3-methoxy-4-propargyloxy)phenyl)-1-oxo-2-propenyl]amino]benzoic acid has an X-ray powder diffraction (XRPD) pattern. FIG. 11 depicts an example of an XRPD pattern for crystalline Form V. In some embodiments, XRPD pattern of the crystalline Form V of the potassium salt of (E)-2-[[3-(3-methoxy-4-propargyloxy) phenyl)-1-oxo-2-propenyl]amino]benzoic acid includes at least one diffraction peak selected from 9.84, 10.56, 14.10, and 25.06 degrees 2θ (±0.2 degrees 2θ). In some embodiments, crystalline Form V of the potassium salt of (E)-2-[[3-(3-methoxy-4-propargyloxy)phenyl)-1-oxo-2-propenyl] amino]benzoic acid has an XRPD pattern comprising at least two peaks selected from 9.84, 10.56, 14.10, and 25.06 degrees 2θ (±0.2 degrees 2θ). In some embodiments, crystalline Form V of the potassium salt of (E)-2-[[3-(3-methoxy-4-propargyloxy)phenyl)-1-oxo-2-propenyl]amino] benzoic acid has an XRPD pattern comprising at least three peaks selected from 9.84, 10.56, 14.10, and 25.06 degrees 2θ (±0.2 degrees 2θ). In some embodiments, crystalline Form V of the potassium salt of (E)-2-[[3-(3-methoxy-4-propargyloxy)phenyl)-1-oxo-2-propenyl]amino]benzoic acid has an XRPD pattern comprising the peaks at 9.84, 10.56, 14.10, and 25.06 degrees 2θ (±0.2 degrees 2θ). In some embodiments, crystalline Form V of the potassium salt of (E)-2-[[3-(3-methoxy-4-propargyloxy)phenyl)-1-oxo-2-propenyl]amino]benzoic acid has an X-ray diffraction pattern substantially as shown in FIG. 11.

Ammonium Salt of (E)-2-[[3-(3-methoxy-4-propargyloxy)phenyl)-1-oxo-2-propenyl]amino]benzoic acid, and Solid or Crystalline Forms Thereof In embodiments, provided herein is the ammonium salt of (E)-2-[[3-(3-methoxy-4-propargyloxy)phenyl)-1-oxo-2-propenyl]amino]benzoic acid, including solid and crystalline forms thereof.

In embodiments, provided herein is a solid form of the ammonium salt of (E)-2-[[3-(3-methoxy-4-propargyloxy) phenyl)-1-oxo-2-propenyl]amino]benzoic acid.

In some embodiments, provided herein is a crystalline form of the ammonium salt of (E)-2-[[3-(3-methoxy-4-propargyloxy)phenyl)-1-oxo-2-propenyl]amino]benzoic acid.

In some embodiments, the crystalline form of the ammonium salt of (E)-2-[[3-(3-methoxy-4-propargyloxy)phenyl)-1-oxo-2-propenyl]amino]benzoic acid provided herein is crystalline Form VI.

Figure 12:
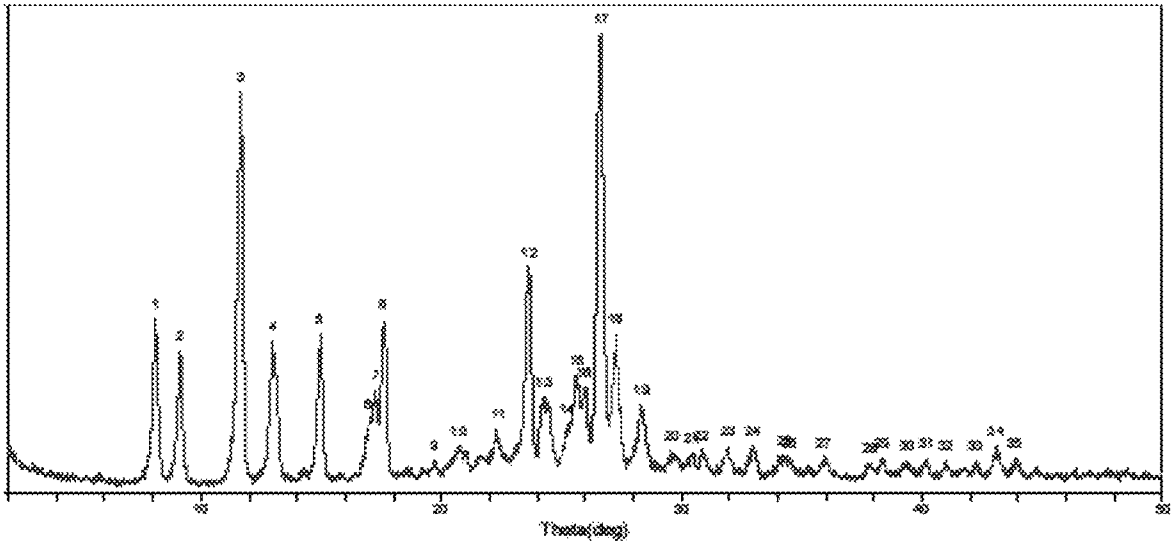
FIG. 12 shows an exemplary X-Ray Powder Diffraction (XRPD) pattern of a sample of the ammonium salt of (E)-2-[[3-(3-methoxy-4-propargyloxy)phenyl)-1-oxo-2-propenyl]amino]benzoic acid in crystalline Form VI.

In some embodiments, crystalline Form VI of the ammonium salt of (E)-2-[[3-(3-methoxy-4-propargyloxy)phenyl)-1-oxo-2-propenyl]amino]benzoic acid has an X-ray powder diffraction (XRPD) pattern. FIG. 12 depicts an example of an XRPD pattern for crystalline Form VI. In some embodiments, XRPD pattern of the crystalline Form VI of the ammonium salt of (E)-2-[[3-(3-methoxy-4-propargyloxy) phenyl)-1-oxo-2-propenyl]amino]benzoic acid includes at least one diffraction peak selected from 8.10, 11.66, 17.62, and 26.64 degrees 2θ (±0.2 degrees 2θ). In some embodiments, crystalline Form VI of the ammonium salt of (E)-2-[[3-(3-methoxy-4-propargyloxy)phenyl)-1-oxo-2-propenyl] amino]benzoic acid has an XRPD pattern comprising at least two peaks selected from 8.10, 11.66, 17.62, and 26.64 degrees 2θ (±0.2 degrees 2θ). In some embodiments, crystalline Form VI of the ammonium salt of (E)-2-[[3-(3-methoxy-4-propargyloxy)phenyl)-1-oxo-2-propenyl]amino] benzoic acid has an XRPD pattern comprising at least three peaks selected from 8.10, 11.66, 17.62, and 26.64 degrees 2θ (±0.2 degrees 2θ). In some embodiments, crystalline Form VI of the ammonium salt of (E)-2-[[3-(3-methoxy-4-propargyloxy)phenyl)-1-oxo-2-propenyl]amino]benzoic acid has an XRPD pattern comprising the peaks at 8.10, 11.66, 17.62, and 26.64 degrees 2θ (±0.2 degrees 2θ). In some embodiments, XRPD pattern of the crystalline Form VI of the ammonium salt of (E)-2-[[3-(3-methoxy-4-propargyloxy) phenyl)-1-oxo-2-propenyl]amino]benzoic acid includes at least one diffraction peak selected from 8.10, 11.66, and 17.62 degrees 2θ (±0.2 degrees 2θ). In some embodiments, crystalline Form VI of the ammonium salt of (E)-2-[[3-(3-methoxy-4-propargyloxy)phenyl)-1-oxo-2-propenyl]amino] benzoic acid has an XRPD pattern comprising at least two peaks selected from 8.10, 11.66, and 17.62 degrees 2θ (±0.2 degrees 2θ). In some embodiments, crystalline Form VI of the ammonium salt of (E)-2-[[3-(3-methoxy-4-propargyloxy)phenyl)-1-oxo-2-propenyl]amino]benzoic acid has an XRPD pattern comprising the peaks at 8.10, 11.66, and 17.62 degrees 2θ (±0.2 degrees 2θ). In some embodiments, crystalline Form VI of the ammonium salt of (E)-2-[[3-(3-methoxy-4-propargyloxy)phenyl)-1-oxo-2-propenyl]amino] benzoic acid has an X-ray diffraction pattern substantially as shown in FIG. 12.

Lysine Salt of (E)-2-[[3-(3-methoxy-4-propargyloxy)phenyl)-1-oxo-2-propenyl]amino]benzoic acid, and Solid or Crystalline Forms Thereof In embodiments, provided herein is the lysine salt of (E)-2-[[3-(3-methoxy-4-propargyloxy)phenyl)-1-oxo-2-propenyl]amino]benzoic acid, including solid and crystalline forms thereof.

In embodiments, provided herein is a solid form of the lysine salt of (E)-2-[[3-(3-methoxy-4-propargyloxy)phenyl)-1-oxo-2-propenyl]amino]benzoic acid.

In some embodiments, provided herein is a crystalline form of the lysine salt of (E)-2-[[3-(3-methoxy-4-propargyloxy)phenyl)-1-oxo-2-propenyl]amino]benzoic acid.

In some embodiments, the crystalline form of the lysine salt of (E)-2-[[3-(3-methoxy-4-propargyloxy)phenyl)-1-oxo-2-propenyl]amino]benzoic acid provided herein is crystalline Form VII.

Figure 13:
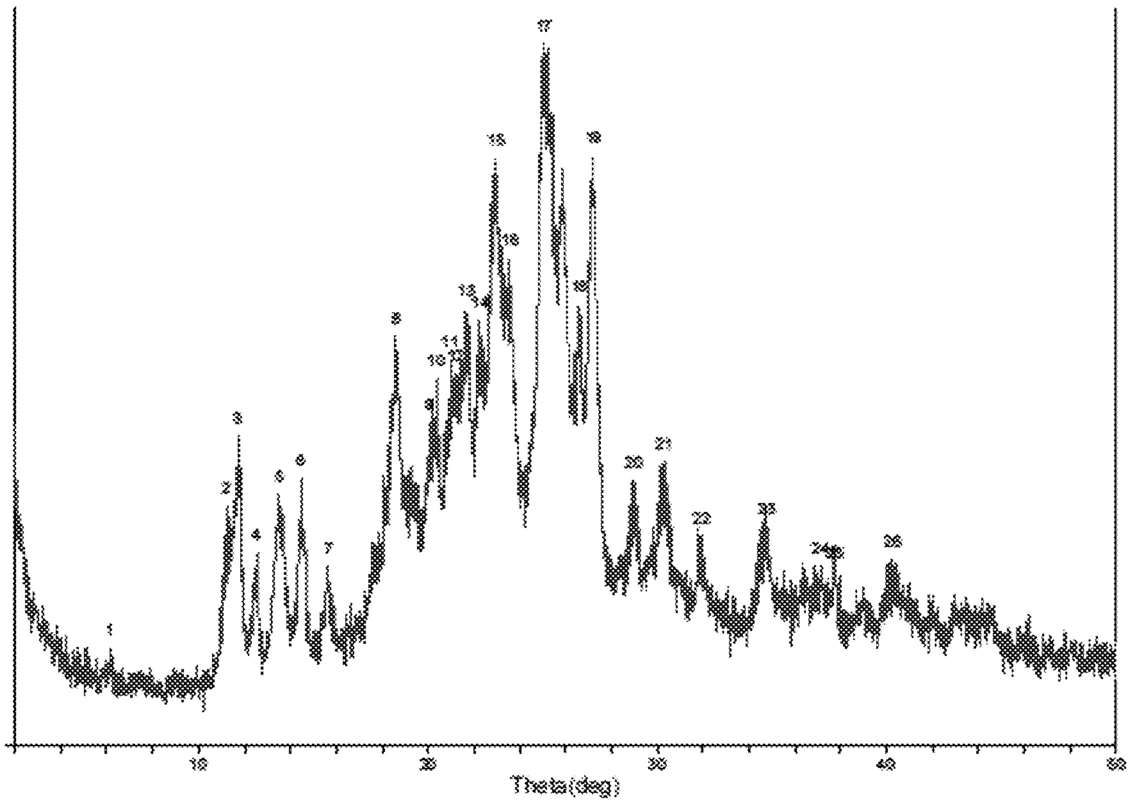
FIG. 13 shows an exemplary X-Ray Powder Diffraction (XRPD) pattern of a sample of the lysine salt of (E)-2-[[3-(3-methoxy-4-propargyloxy)phenyl)-1-oxo-2-propenyl]amino]benzoic acid in crystalline Form VII.

In some embodiments, crystalline Form VII of the lysine salt of (E)-2-[[3-(3-methoxy-4-propargyloxy)phenyl)-1-oxo-2-propenyl]amino]benzoic acid has an X-ray powder diffraction (XRPD) pattern. FIG. 13 depicts an example of an XRPD pattern for crystalline Form VII. In some embodiments, XRPD pattern of the crystalline Form VII of the lysine salt of (E)-2-[[3-(3-methoxy-4-propargyloxy)phenyl)-1-oxo-2-propenyl]amino]benzoic acid includes at least one diffraction peak selected from 11.76, 14.48, 18.60, and 27.22 degrees 2θ (±0.2 degrees 2θ). In some embodiments, crystalline Form VII of the lysine salt of (E)-2-[[3-(3-methoxy-4-propargyloxy)phenyl)-1-oxo-2-propenyl]amino] benzoic acid has an XRPD pattern comprising at least two peaks selected from 11.76, 14.48, 18.60, and 27.22 degrees 2θ (±0.2 degrees 2θ). In some embodiments, crystalline Form VII of the lysine salt of (E)-2-[[3-(3-methoxy-4-propargyloxy)phenyl)-1-oxo-2-propenyl]amino]benzoic acid has an XRPD pattern comprising at least three peaks selected from 11.76, 14.48, 18.60, and 27.22 degrees 2θ (±0.2 degrees 2θ). In some embodiments, crystalline Form VII of the lysine salt of (E)-2-[[3-(3-methoxy-4-propargyloxy)phenyl)-1-oxo-2-propenyl]amino]benzoic acid has an XRPD pattern comprising the peaks at 11.76, 14.48, 18.60, and 27.22 degrees 2θ (±0.2 degrees 2θ). In some embodiments, crystalline Form VII of the lysine salt of (E)-2-[[3-(3-methoxy-4-propargyloxy)phenyl)-1-oxo-2-propenyl] amino]benzoic acid has an XRPD pattern comprising at least one peak selected from 11.76, 14.48, and 18.60 degrees 2θ (±0.2 degrees 2θ). In some embodiments, crystalline Form VII of the lysine salt of (E)-2-[[3-(3-methoxy-4-propargyloxy)phenyl)-1-oxo-2-propenyl]amino]benzoic acid has an XRPD pattern comprising at least two peaks selected from 11.76, 14.48, and 18.60 degrees 2θ (±0.2 degrees 2θ). In some embodiments, crystalline Form VII of the lysine salt of (E)-2-[[3-(3-methoxy-4-propargyloxy)phenyl)-1-oxo-2-propenyl]amino]benzoic acid has an XRPD pattern comprising the peaks at 11.76, 14.48, and 18.60 degrees 2θ (±0.2 degrees 2θ). In some embodiments, crystalline Form VII of the lysine salt of (E)-2-[[3-(3-methoxy-4-propargyloxy)phenyl)-1-oxo-2-propenyl]amino]benzoic acid has an X-ray diffraction pattern substantially as shown in FIG. 13.

Process of Preparation

Also provided herein are processes for preparing solid forms, pharmaceutically acceptable salts, and crystalline forms thereof described herein.

Pharmaceutically acceptable salts of (E)-2-[[3-(3-methoxy-4-propargyloxy)phenyl)-1-oxo-2-propenyl]amino] benzoic acid (e.g., the ethanolamine salt of (E)-2-[[3-(3-methoxy-4-propargyloxy)phenyl)-1-oxo-2-propenyl]amino] benzoic acid) and crystalline forms thereof provided herein may be prepared by a process comprising the step of contacting (E)-2-[[3-(3-methoxy-4-propargyloxy)phenyl)-1-oxo-2-propenyl]amino]benzoic acid, or a salt or solvate thereof, with an appropriate source of counter-ions (e.g., ethanolamine), or a salt or solvate thereof, in a solvent at a first predetermined temperature.

In certain embodiments, the molar ratio of the source of counter-ions, or a salt or solvate thereof, versus (E)-2-[[3-(3-methoxy-4-propargyloxy)phenyl)-1-oxo-2-propenyl] amino]benzoic acid, or a salt or solvate thereof, in the contacting step to form the pharmaceutically acceptable salt of (E)-2-[[3-(3-methoxy-4-propargyloxy)phenyl)-1-oxo-2-propenyl]amino]benzoic acid provided herein is about 1. In certain embodiments, the contacting step to form the pharmaceutically acceptable salt of (E)-2-[[3-(3-methoxy-4-propargyloxy)phenyl)-1-oxo-2-propenyl]amino]benzoic acid provided herein is performed in the presence of an excess amount of the source of counter-ions, or a salt or solvate thereof, to (E)-2-[[3-(3-methoxy-4-propargyloxy)phenyl)-1-oxo-2-propenyl]amino]benzoic acid, or a salt or solvate thereof, to maximize the yield of the process. In certain embodiments, the molar ratio of the source of counter-ions, or a salt or solvate thereof, versus (E)-2-[[3-(3-methoxy-4-propargyloxy)phenyl)-1-oxo-2-propenyl]amino]benzoic acid, or a salt or solvate thereof, is no less than about 1.01, no less than about 1.05, no less than about 1.1, or no less than about 1.2. In certain embodiments, the molar ratio of the source of counter-ions, or a salt or solvate thereof, versus (E)-2-[[3-(3-methoxy-4-propargyloxy)phenyl)-1-oxo-2-propenyl]amino]benzoic acid, or a salt or solvate thereof, is ranging from about 1.00 to about 10, from about 1.05 to about 8, from about 1.05 to about 5, from about 1.1 to about 5, from about 1.1 to about 3, from about 1.1 to about 8, or from about 1.2 to about 2.5.

Suitable solvents for use in the contacting step to form the pharmaceutically acceptable salt of (E)-2-[[3-(3-methoxy-4-propargyloxy)phenyl)-1-oxo-2-propenyl]amino]benzoic acid provided herein include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

In certain embodiments, the solvent for the contacting step to form the pharmaceutically acceptable salt of (E)-2-[[3-(3-methoxy-4-propargyloxy)phenyl)-1-oxo-2-propenyl]amino]benzoic acid provided herein is acetonitrile, acetone, methyl ethyl ketone, methyl isobutyl ketone, N,N-dimethylformamide, dimethylsulfoxide, a low alkanol (e.g., methanol, ethanol, n-propanol, isopropanol, sec-butanol, or 2-methoxyethanol), methyl acetate, ethyl acetate, ethyl formate, isopropyl acetate, isobutyl acetate, chloroform, dichloromethane, methyl tert-butyl ether, tetrahydrofuran, 1,4-dioxane, petroleum ether, hexanes, heptane, toluene, water, or a mixture thereof. In another embodiment, the solvent for the contacting step to form the pharmaceutically acceptable salt of (E)-2-[[3-(3-methoxy-4-propargyloxy)phenyl)-1-oxo-2-propenyl]amino]benzoic acid provided herein comprises a $C_{1-5}$ alkanol. In yet another embodiment, the solvent for the contacting step to form the pharmaceutically acceptable salt of (E)-2-[[3-(3-methoxy-4-propargyloxy)phenyl)-1-oxo-2-propenyl]amino]benzoic acid provided herein comprises methanol, ethanol, propanol, isopropanol, sec-butanol, 2-methoxyethanol, or a mixture thereof.

In certain embodiments, the solvent for the contacting step to form the pharmaceutically acceptable salt of (E)-2-[[3-(3-methoxy-4-propargyloxy)phenyl)-1-oxo-2-propenyl]amino]benzoic acid provided herein is selected from methanol, ethanol, isopropanol, acetonitrile, acetone, methyl ethyl ketone, methyl isobutyl ketone, ethyl acetate, isopropyl acetate, methyl tert-butyl ether, tetrahydrofuran, toluene, n-heptane, 1,4-dioxane, water, dichloromethane, acetic acid, or a mixture thereof.

In some embodiments, the contacting step to form the pharmaceutically acceptable salt of (E)-2-[[3-(3-methoxy-4-propargyloxy)phenyl)-1-oxo-2-propenyl]amino]benzoic acid provided herein is carried out at a temperature ranging from about −10 to about 150° C., from about 10 to about 110° C., or from about 20 to about 100° C.; for example, about 20° C., about 30° C., about 40° C., about 50° C., about 60° C., about 70° C., about 80° C., about 90° C., or about 100° C.

In some embodiments, the processes provided herein each further comprise the step of preparing a solid form of the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) provided herein at a second predetermined temperature. Solid forms of the pharmaceutically acceptable salt of (E)-2-[[3-(3-methoxy-4-propargyloxy)phenyl)-1-oxo-2-propenyl]amino]benzoic acid provided herein can be prepared from a solution or slurry of the pharmaceutically acceptable salt of (E)-2-[[3-(3-methoxy-4-propargyloxy)phenyl)-1-oxo-2-propenyl]amino]benzoic acid in a solvent using conventional methods, including, but not limited to cooling, chilling, solvent evaporation, or addition of an anti-solvent. Other forming methods may also be applicable, including spray drying, roller drying, lyophilization, and melt crystallization.

In some embodiments, the processes provided herein each further comprise the step of crystallising the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) provided herein at a second predetermined temperature.

Processes for preparing the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) in an amorphous form or crystalline form comprise the step of contacting the pharmaceutically acceptable salt of (E)-2-[[3-(3-methoxy-4-propargyloxy)phenyl)-1-oxo-2-propenyl]amino]benzoic acid with a solvent, in which the particulates of the pharmaceutically acceptable salt of (E)-2-[[3-(3-methoxy-4-propargyloxy)phenyl)-1-oxo-2-propenyl]amino]benzoic acid in an amorphous form, or a solid or a crystalline form of the pharmaceutically acceptable salt of (E)-2-[[3-(3-methoxy-4-propargyloxy)phenyl)-1-oxo-2-propenyl]amino] benzoic acid or a solvate thereof, may be formed from a solution or converted from one solid form to another. The process may further comprise an isolation step, in which the compounds may be isolated by a conventional method, such as filtration and centrifugation, followed by washing with a solvent and then drying (e.g., vacuum oven drying, air drying, or desiccator drying).

Suitable solvents for use in preparing the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) provided herein in an amorphous form or crystalline form include but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane (DCM), 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

In various embodiments, the solvent for preparing a crystalline form of the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) provided herein is acetonitrile, acetone, methyl ethyl ketone, methyl isobutyl ketone, N,N-dimethylformamide, dimethylsulfoxide, a low alkanol (e.g., methanol, ethanol, n-propanol, isopropanol, sec-butanol, or 2-methoxyethanol), methyl acetate, ethyl acetate, ethyl formate, isopropyl acetate, isobutyl acetate, chloroform, dichloromethane, methyl tert-butyl ether, tetrahydrofuran, 1,4-dioxane, petroleum ether, hexanes, heptane, toluene, water, or a mixture thereof. In an embodiment, the solvent for crystallization comprises a C1-5 alkanol. In another embodiment, the solvent for crystallization comprises methanol, ethanol, propanol, isopropanol, sec-butanol, 2-methoxyethanol, or a mixture thereof.

In certain embodiments, the crystallization is carried out using conventional methods, including, but not limited to, cooling, chilling, solvent evaporation, addition of an anti-solvent, or reverse addition to an anti-solvent. In certain embodiment, the crystallization is carried out at a temperature ranging from about −50 to about 100° C., from about −30 to about 50° C., or from about −10 to about 30° C. In certain embodiments, the process further comprises the step of seeding to accelerate crystallization. In certain embodiments, the process further comprises an isolation step, in which the solid formed is isolated by a conventional method, such as filtration and centrifugation, followed by washing with a solvent and then drying.

In certain embodiments, the crystallization is carried out by cooling a solution containing the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid provided herein) provided herein to or below room temperature, or by solvent evaporation. In certain embodiments, the crystallization is carried out by adding an anti-solvent to a solution containing the pharmaceutically acceptable salt of (E)-2-[[3-(3-methoxy-4-propargyloxy)phenyl)-1-oxo-2-propenyl]amino]benzoic acid, or by adding a solution containing the pharmaceutically acceptable salt of (E)-2-[[3-(3-methoxy-4-propargyloxy)phenyl)-1-oxo-2-propenyl]amino]benzoic acid to an anti-solvent.

Suitable anti-solvents include, but are not limited to, hydrocarbons, including petroleum ether, pentane, hexane(s), heptane, octane, isooctane, cyclopentane, cyclohexane, methylcyclohexane, benzene, toluene, xylene, tetralin, and cumene; chlorinated hydrocarbons, including dichloromethane, 1,2-dichloroethane, 1,1-dichloroethene, 1,2-dichloroethene, chloroform, trichloroethane, trichloroethene, carbon tetrachloride, chlorobenzene, and trifluoromethylbenzene; alcohols, including isopropanol, 1-propanol, 1-butanol, 2-butanol, t-butanol, 3-methyl-1-butanol, 1-pentanol, 2-ethoxyethanol, and ethyleneglycol; ethers, including diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, and methyl isobutyl ketone (MIBK); esters, including methyl acetate, ethyl formate, ethyl acetate, propyl acetate, isopropyl acetate, isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN); sulfoxides, such as dimethyl sulfoxide (DMSO); sulfones, such sulfolane; nitro compounds, such as nitromethane and nitrobenzene; heterocycles, such as N-methyl pyrrolindone, 2-methyl tetrahydrofuran, tetrahydrofuran (THF), dioxane, and pyridine; carboxylic acids, such as acetic acid, trichloroacetic acid, and trifluoroacetic acid; phosphoramides, such as hexamethylphosphoramide; carbon sulfide; water; and mixtures thereof.

When two solvents are used as a solvent/anti-solvent pair, the pharmaceutically acceptable salt of (E)-2-[[3-(3-methoxy-4-propargyloxy)phenyl)-1-oxo-2-propenyl]amino] benzoic acid (e.g., the ethanolamine salt of (E)-2-[[3-(3-methoxy-4-propargyloxy)phenyl)-1-oxo-2-propenyl]amino] benzoic acid) has a higher solubility in the solvent than in the anti-solvent. Optionally, the solvent and the anti-solvent in a solvent/anti-solvent pair are at least partially miscible.

In some embodiments, the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein exhibits ease of manufacture or processability, and/or improved solidification and/or crystallisation properties. As a result, in some embodiments, the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein is obtained in higher yields or via fewer manufacturing or purification steps compared to the free form of (E)-2-[[3-(3-methoxy-4-propargyloxy)phenyl)-1-oxo-2-propenyl]amino]benzoic acid, or compared to other pharmaceutically acceptable salts of (E)-2-[[3-(3-methoxy-4-propargyloxy)phenyl)-1-oxo-2-propenyl]amino]benzoic acid. In some embodiments, the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein is obtained in higher purity (e.g. substantially pure or substantially homogeneous) compared to the free form of (E)-2-[[3-(3-methoxy-4-propargyloxy)phenyl)-1-oxo-2-propenyl]amino]benzoic acid, or compared to other pharmaceutically acceptable salts of (E)-2-[[3-(3-methoxy-4-propargyloxy)phenyl)-1-oxo-2-propenyl]amino]benzoic acid.

Pharmaceutical Compositions

Also provided herein are pharmaceutical compositions comprising the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or solid or crystalline forms thereof provided herein, and one or more pharmaceutically acceptable carriers or excipients.

The choice of excipient, to a large extent, depends on factors such as the particular mode of administration, the effect of the excipient on the solubility and stability of the active ingredient, and the nature of the dosage form.

The pharmaceutical compositions provided herein can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology,* 2nd Edition, Rathbone et al., Eds., Marcel Dekker, Inc.: New York, NY, 2008).

In one embodiment, the pharmaceutical compositions provided herein are formulated in a dosage form for oral administration, which comprise the pharmaceutically acceptable salt of (E)-2-[[3-(3-methoxy-4-propargyloxy)phenyl)-1-oxo-2-propenyl]amino]benzoic acid or solid or crystalline forms thereof provided herein, and one or more pharmaceutically acceptable excipients.

In one embodiment, the oral pharmaceutical composition comprises the pharmaceutically acceptable salt of (E)-2-[[3-(3-methoxy-4-propargyloxy)phenyl)-1-oxo-2-propenyl]amino]benzoic acid or solid or crystalline forms thereof provided herein, and one or more pharmaceutically acceptable excipients, each of which is independently selected from candellila wax, cellulose acetate, crospovidone or povidone, dibutyl sebacate, ethylcellulose, glyceryl behenate, hypromellose, magnesium stearate, microcrystalline cellulose, polyethylene glycol (e.g., PEG 400 or PEG 8000), polyvinyl alcohol, polysorbate (e.g., polysorbate 80), sodium carboxymethyl cellulose, sodium dioxide, sodium lauryl sulfate, synthetic black iron oxides, titanium dioxide, triacetin, hydrochloric acid, potassium bicarbonate, saccharin calcium, xylitol, water, and cherry flavour.

In another embodiment, the oral pharmaceutical composition comprises the pharmaceutically acceptable salt of (E)-2-[[3-(3-methoxy-4-propargyloxy)phenyl)-1-oxo-2-propenyl]amino]benzoic acid or solid or crystalline forms thereof provided herein, and one, two, or more pharmaceutically acceptable excipients, each of which is independently selected from candellila wax, cellulose acetate, corn starch, crospovidone or povidone, dibutyl sebacate, ethylcellulose, glyceryl behenate, hypromellose, magnesium stearate, microcrystalline cellulose, polyethylene glycol, polyvinyl alcohol, polysorbate, sodium carboxymethyl cellulose, sodium dioxide, sodium lauryl sulfate, synthetic black iron oxides, titanium dioxide, and triacetin.

In one embodiment, the oral pharmaceutical composition is a tablet. In another embodiment, the oral pharmaceutical composition is an extended-release tablet. In yet another embodiment, the oral pharmaceutical composition is a coated tablet.

In another embodiment, the pharmaceutical compositions provided herein are formulated in a dosage form for parenteral administration, which comprise the pharmaceutically acceptable salt of (E)-2-[[3-(3-methoxy-4-propargyloxy)phenyl)-1-oxo-2-propenyl]amino]benzoic acid or solid or crystalline forms thereof provided herein, and one or more pharmaceutically acceptable excipients. In one embodiment, the pharmaceutical compositions provided herein are formulated in a dosage form for intravenous administration. In another embodiment, the pharmaceutical compositions provided herein are formulated in a dosage form for intramuscular administration. In yet another embodiment, the pharmaceutical compositions provided herein are formulated in a dosage form for subcutaneous administration.

In yet another embodiment, the pharmaceutical compositions provided herein are formulated in a dosage form for topical administration, which comprise the pharmaceutically acceptable salt of (E)-2-[[3-(3-methoxy-4-propargyloxy)phenyl)-1-oxo-2-propenyl]amino]benzoic acid or solid or crystalline forms thereof provided herein, and one or more pharmaceutically acceptable excipients.

The pharmaceutical compositions provided herein may be provided in unit dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

In certain embodiments, the pharmaceutical compositions provided herein comprise in each unit-dosage form the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount ranging from about 10 to about 10,000 mg. In certain embodiments, the pharmaceutical compositions provided herein comprise in each unit-dosage form the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount of about 10, about 50, about 100, about 200, about 300, about 400, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, and about 1500 mg.

In some embodiments, the pharmaceutical compositions provided herein comprise in each unit-dosage form the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount of about 10, about 50, about 100, about 150, about 200, about 250, about 300, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 mg.

In some embodiments, the pharmaceutical compositions provided herein comprise in each unit-dosage form the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount of about 20, about 30, about 40, about 50, about 100, about 150, about 200, about 250, about 300, about 350, or about 400 mg.

In certain embodiments, the pharmaceutical compositions provided herein comprise in each unit-dosage form the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount ranging from about 1 to about 100, about 1 to about 50, from about 2 to about 20, or from about 2 to about 10 mg. In certain embodiments, the pharmaceutical compositions provided herein comprise in each unit-dosage form the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount of about 1, about 2, about 3, about 4, about 5, about 6, about 7, about 8, about 9, about 10, about 11, about 12, about 13, about 14, about 15, about 16, about 17, about 18, about 19, or about 20 mg.

In some embodiments, the pharmaceutical compositions provided herein comprise the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount effective to provide a dose of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, or about 400 mg/kg of (E)-2-[[3-(3-methoxy-4-propargyloxy)phenyl)-1-oxo-2-propenyl]amino]benzoic acid. In some embodiments, the pharmaceutical compositions provided herein comprise the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount effective to provide a dose of between about 10 and about 400 mg/kg, between about 50 and about 300 mg/kg, between about 100 and about 250 mg/kg of (E)-2-[[3-(3-methoxy-4-propargyloxy)phenyl)-1-oxo-2-propenyl]amino]benzoic acid. In certain embodiments, the pharmaceutical compositions provided herein comprise the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount effective to provide a dose of about 200 mg/kg of (E)-2-[[3-(3-methoxy-4-propargyloxy)phenyl)-1-oxo-2-propenyl]amino]benzoic acid.

In some embodiments, the pharmaceutical compositions provided herein comprise the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount effective to provide a concentration of from 10 μM to 200 μM, or from 10 μM to 100 μM, or from 10 UM to 50 μM of (E)-2-[[3-(3-methoxy-4-propargyloxy)phenyl)-1-oxo-2-propenyl]amino]benzoic acid at a site of its action. In some embodiments, the pharmaceutical compositions provided herein comprise the pharmaceutically acceptable salt of (E)-2-[[3-(3-methoxy-4-propargyloxy)phenyl)-1-oxo-2-propenyl]amino]benzoic acid or solid or crystalline forms thereof provided herein in an amount effective to provide a concentration of about 20 to about 40 μM, about 25 to about 35 μM, or about 30 μM of (E)-2-[[3-(3-methoxy-4-propargyloxy)phenyl)-1-oxo-2-propenyl]amino]benzoic acid at a site of its action.

As used herein, a "site of action" of (E)-2-[[3-(3-methoxy-4-propargyloxy)phenyl)-1-oxo-2-propenyl]amino]benzoic acid may refer to cells or tissues affected by fibrosis, inflammation and/or proliferation, or cells or tissues implicated in the progress of fibrosis, inflammation and/or proliferation.

The pharmaceutical compositions provided herein can be administered once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

The pharmaceutical compositions provided herein are intended to be administered by a suitable route, including orally in the form of capsules, tablets, granules, powders or liquid formulations including syrups; parenterally, such as subcutaneously, intravenously, intramuscularly, with intersternal injection or infusion techniques (as sterile injectable aqueous (aq.) or non-aqueous solutions or suspensions); nasally, such as by inhalation spray; topically, such as in the form of a cream or ointment; rectally, such as in the form of suppositories; liposomally; and locally. The compositions can be in liquid, semi-liquid or solid form and are formulated in a manner suitable for each route of administration. In certain embodiments, administration of the formulation includes parenteral and oral modes of administration. In various embodiments, the pharmaceutical compositions provided herein are administered orally. In one embodiment, the pharmaceutical compositions provided herein are administered directly to the eye via injection.

Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, A VICEL-PH-105 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pregelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Vee gum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 and CAB-O-SIL®; and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, MA), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxy ethylene sorbitan monooleate (TWEEN® 20), polyoxy ethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation.

Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavouring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as noneffervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, above).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable matrixes inner include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, CA), and BIOJECT™ (Bioject Medical Technologies Inc., Tualatin, OR).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

Modified Release

The pharmaceutical compositions provided herein can be formulated as a modified release dosage form. As used herein, the term "modified release" refers to a dosage form in which the rate or place of release of the active ingredient (s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, DE) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

The pharmaceutical compositions provided herein can also be formulated to be targeted to a particular tissue, receptor, or other area of the body of the subject to be treated, including liposome-, resealed erythrocyte-, and antibody-based delivery systems.

Methods of Use

Further provided herein are methods of use of the solid forms, pharmaceutically acceptable salts, or crystalline forms thereof disclosed herein, or the pharmaceutical compositions thereof disclosed herein, for treating, preventing, or ameliorating a fibrotic, inflammatory or proliferative disease or condition in a subject, comprising administering to the subject a therapeutically effective amount of the solid form, pharmaceutically acceptable salt, or crystalline form thereof disclosed herein, or the pharmaceutical composition disclosed herein.

In some embodiments, provided herein is a method of treating, preventing, or ameliorating a fibrotic, inflammatory or proliferative disease or condition in a subject, comprising administering to the subject a therapeutically effective amount of the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein, or a pharmaceutical composition comprising the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein.

In various embodiments, the subject is an animal, including, but not limited to, a primate (e.g., human), cow, pig, sheep, goat, horse, dog, cat, rabbit, rat, or mouse. In some embodiments, the subject is a human.

In some embodiments, the fibrotic, inflammatory or proliferative disease or condition is selected from fibrosis of skin, lung, heart, kidney, pancreas, eye and liver.

In certain embodiments, the fibrotic, inflammatory or proliferative disease or condition is selected from diabetic cardiomyopathy, congestive heart failure, ischemic heart disease, hypertension, peripheral artery disease, cerebrovascular disease, kidney disease, systemic sclerosis, Scleroderma, hypertrophic scars, keloids, pulmonary fibrosis, interstitial lung disease (ILD), non-alcoholic steatohepatitis (NASH), non-alcoholic fatty liver disease (NAFLD), primary biliary cirrhosis (PBC), and primary sclerosis cholangitis (PSC).

In certain embodiments, the fibrotic, inflammatory or proliferative diseases or conditions treatable with the pharmaceutically acceptable salts and/or pharmaceutical compositions thereof provided herein include but are not limited to fibrotic eye diseases, such as diabetic retinopathy, wet age related macular degeneration, and diabetic macular edema. In some embodiments, the fibrotic eye disease is proliferative vitreoretinopathy, corneal edema, anterior and posterior uveitis, pterygium, corneal disease, dry eye, conjunctivitis, allergy- and laser-induced exudation, non-age related macular degeneration, macular edema, age-related macular degeneration, or ocular von Hippel-Lindau disease.

In certain embodiments, the fibrotic, inflammatory or proliferative disease or condition is a kidney disease. In some embodiments, the fibrotic, inflammatory or proliferative disease or condition is selected from chronic kidney disease, progressive kidney disease, diabetic nephropathy, diabetic kidney disease, glomerulonephritis, focal segmental glomerulosclerosis, systemic lupus, lupus nephritis, primary glomerulonephritis, membranous nephropathy, membranoproliferative glomerulonephritis, diffuse proliferative glomerulonephritis, membranous focal segmental glomerulosclerosis, secondary glomerulonephritis, membranous nephropathy, IgA nephropathy, ischemic nephropathy, or Alports Syndrome. In certain embodiments, the fibrotic, inflammatory or proliferative disease or condition is a chronic kidney disease. In some embodiments, the kidney disease may include, but is not limited to, a progressive glomerular kidney disease including without limitation diabetic nephropathy (e.g., as a consequence of Type I or Type II diabetes or systemic lupus), primary glomerulonephritis (e.g., membranous nephropathy, focal segmental glomerulosclerosis, membranoproliferative glomerulonephritis, diffuse proliferative glomerulonephritis, membranous focal segmental glomerulosclerosis) or secondary glomerulonephritis (e.g., diabetic nephropathy, ischemic nephropathy). In some embodiments, the kidney disease may include progressive kidney diseases with origins primarily in the tubulointerstitium. In some embodiments, the kidney disease may include, e.g., chronic interstitial nephritis, autosomal dominant tubulointerstitial fibrosis, or reflux nephropathy.

In certain embodiments, the fibrotic, inflammatory or proliferative disease or condition is diabetic nephropathy.

In certain embodiments, the fibrotic, inflammatory or proliferative disease or condition is focal segmental glomerulosclerosis.

In certain embodiments, the fibrotic, inflammatory or proliferative disease or condition is diabetic cardiomyopathy, congestive heart failure, or ischemic heart disease.

In certain embodiments, the fibrotic, inflammatory or proliferative disease or condition is systemic sclerosis or Scleroderma.

In certain embodiments, the fibrotic, inflammatory or proliferative disease or condition is pulmonary fibrosis. In some embodiments, the pulmonary fibrosis is idiopathic pulmonary fibrosis (IPF).

In certain embodiments, the fibrotic, inflammatory or proliferative disease or condition is chronic obstructive pulmonary disorder (COPD), asthma, or cystic fibrosis.

In some embodiments, the fibrotic, inflammatory or proliferative diseases or conditions include but are not limited to diseases selected from fibrotic skin disorders, such as keloids, hypertrophic scars and scleroderma; lung disease, such as pulmonary fibrosis; heart disease, such as heart failure due to ischaemic heart disease, valvular heart disease and hypertensive heart disease, diabetic cardiomyopathy and hypertension; and liver disease, such as cirrhosis of the liver.

In some embodiments, the fibrotic, inflammatory or proliferative disease or condition is kidney disease, such as chronic kidney disease. In some embodiments, the kidney disease is a progressive kidney disease. In some embodiments, the progressive kidney disease is due to glomerulonephritis or diabetic nephropathy. In some embodiments, the kidney disease is selected from one or more of progressive kidney disease, glomerulonephritis, diabetic kidney disease, diabetic nephropathy, systemic lupus, primary glomerulonephritis, membranous nephropathy, focal segmental glomerulosclerosis, membranoproliferative glomerulonephritis, diffuse proliferative glomerulonephritis, membranous focal segmental glomerulosclerosis, secondary glomerulonephritis, or ischemic nephropathy. In certain embodiments, the application provides a method of treating focal segmental glomerulosclerosis. In certain embodiments, the application provides a method of treating inflammation.

In some embodiments, the fibrotic, inflammatory or proliferative disease or condition is diabetic heart disease or diabetic kidney disease. In some embodiments, the fibrotic, inflammatory or proliferative disease or condition is diabetic cardiomyopathy. In some embodiments, the kidney disease is chronic kidney disease. In some embodiments, the kidney disease is a progressive glomerular kidney disease including without limitation diabetic nephropathy (e.g., as a consequence of Type I or Type II diabetes or systemic lupus), primary glomerulonephritis (e.g., membranous nephropathy, focal segmental glomerulosclerosis, membranoproliferative glomerulonephritis, diffuse proliferative glomerulonephritis, membranous focal segmental glomerulosclerosis), or secondary glomerulonephritis (e.g., diabetic nephropathy, ischemic nephropathy).

In some embodiments, the pharmaceutically acceptable salts and/or pharmaceutical compositions thereof provided herein are useful in the treatment of an inflammatory disease or condition.

Generally, inflammatory diseases or conditions treatable with the solid form, pharmaceutically acceptable salt, or crystalline form thereof provided herein, or the pharmaceutical composition thereof provided herein, relate to any diseases or condition characterized by an abnormal, irregular, excessive, rogue or unwarranted inflammatory response.

In some embodiment, the inflammatory disease or condition is the result of an injury to a tissue. In some embodiments, the inflammatory disease, disorder or condition is the result of an autoimmune condition, while in further embodiment, the inflammatory disease, disorder or condition is the result of a bacterial or viral infection or the presence of a toxin.

The solid form, pharmaceutically acceptable salt, or crystalline form thereof provided herein, or the pharmaceutical composition thereof provided herein, can have anti-inflammatory activity and/or immunomodulatory activity and can be useful in the treatment of diseases or conditions including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. The solid forms, pharmaceutically acceptable salts, or crystalline forms thereof provided herein, or the pharmaceutical compositions thereof provided herein, and methods provided herein may be useful in treating one or more of these diseases, disorders or conditions.

In some embodiments, the inflammatory disease or condition is at least one inflammatory disease or condition selected from the group consisting of inflammatory bowel disease, celiac disease, colitis, irritable bowel syndrome, intestinal hyperplasia, metabolic syndrome, obesity, diabetes, rheumatoid arthritis, liver disease, hepatic steatosis, fatty liver disease, non-alcoholic fatty liver disease (NAFLD), and nonalcoholic steatohepatitis (NASH).

In some embodiments, the inflammatory disease or condition is arthritis, osteoarthritis, psoriatic arthritis, rheumatoid arthritis, diabetic retinopathy, retinal inflammation, retinitis, Sjogren's syndrome, macular degeneration, gout, pseudogout, pericarditis, or uveitis.

In some embodiments, the inflammatory disease or condition is focal segmental glomerulosclerosis, lupus nephritis, membranous nephropathy, IgA nephropathy, chronic obstructive pulmonary disorder (COPD), asthma, or cystic fibrosis.

In some embodiments, the inflammatory disease or condition is an autoimmune disease or condition. In some embodiments, the autoimmune disease or condition treatable with the pharmaceutically acceptable salts and/or pharmaceutical compositions thereof provided herein is systemic lupus erythematosus (SLE), inflammatory bowel disease, Crohn's disease, ulcerative colitis, graft versus host disease, multiple sclerosis, or rheumatoid arthritis.

In some embodiments, the solid forms, pharmaceutically acceptable salts, or crystalline forms thereof provided herein, or the pharmaceutical compositions thereof provided herein, are useful in the treatment of a proliferative disease or condition.

Generally, proliferative diseases or conditions treatable with the solid forms, pharmaceutically acceptable salts, or crystalline forms thereof provided herein, or the pharmaceutical compositions thereof provided herein, relate to any disease or condition characterized by aberrant cell proliferation. Cell proliferation may be self-propagating and includes an inappropriate or excessive wound healing response. The cellular proliferation can increase the influx of inflammatory cytokines and inflammatory cells, and thus be associated with inflammation and/or degeneration.

Proliferative diseases or conditions treatable with the solid forms, pharmaceutically acceptable salts, or crystalline forms thereof provided herein, or the pharmaceutical compositions thereof provided herein, include, but are not limited to, various retinopathies.

In some embodiments, the proliferative diseases or conditions suitable for treatment by the methods provided herein include, but are not limited to, diabetic retinopathy, diabetic macular edema, macular degeneration, retinopathy of prematurity (ROP), and proliferative vitreoretinopathy (PVR).

Proliferative diseases or conditions treatable with the solid forms, pharmaceutically acceptable salts, or crystalline forms thereof provided herein, or the pharmaceutical compositions thereof provided herein, further include, but are not limited to, various tumours and cancers, benign or malignant, metastatic or non-metastatic.

Cancers treatable with the solid forms, pharmaceutically acceptable salts, or crystalline forms thereof provided herein, or the pharmaceutical compositions thereof provided herein, include a variety of cancers, including, among others, breast cancer, skin cancer, ovarian cancer, renal cancer, gastrointestinal cancer, kidney cancer, bladder cancer, pancreatic cancer, lung squamous carcinoma, and adenocarcinoma.

In some embodiments, the cancer is a cancer that is characterized by the presence of one or more tumours in the subject. Examples of cancers suitable for treatment by the solid forms, pharmaceutically acceptable salts, or crystalline forms thereof provided herein, or the pharmaceutical compositions thereof provided herein, include, but are not limited to, metastatic melanoma, metastatic prostate cancer, metastatic breast cancer, triple negative breast cancer, bladder cancer, brain cancer, esophageal cancer, liver cancer, head and neck cancer, squamous cell lung cancer, non-small lung cell cancer, Merkel cell carcinoma, sarcoma, hepatocellular cancer, multiple myeloma, pancreatic cancer, colorectal carcinoma, cervical cancer, gastric carcinoma, kidney cancer, metastatic renal cell carcinoma, leukemia, ovarian cancer, and malignant glioma. In certain embodiments, the cancer is metastatic melanoma, metastatic prostate cancer, or metastatic breast cancer. In some embodiments, the subject has received an allogeneic tissue graft associated with treatment for cancer, e g, after hematopoietic stem cell transplantation used for treatment of a leukemia.

In some embodiments, the cancer suitable for treatment by the solid forms, pharmaceutically acceptable salts, or crystalline forms thereof provided herein, or the pharmaceutical compositions thereof provided herein, is a breast cancer, skin cancer (melanoma), pancreatic cancer, lung cancer, prostate cancer, colon cancer, liver cancer (hepatocellular carcinoma), head and neck cancer, ovarian cancer, or kidney cancer.

In some embodiments, treating a disease or condition described herein with the solid forms, pharmaceutically acceptable salts, or crystalline forms thereof provided herein, or the pharmaceutical compositions thereof provided herein, results in an increase in average survival time of a population of treated subjects in comparison to a population of untreated subjects. Preferably, the average survival time is increased by more than about 30 days; more preferably, by more than about 60 days; more preferably, by more than about 90 days; and even more preferably by more than about 120 days. An increase in survival time of a population may be measured by any reproducible means. In some embodiments, an increase in average survival time of a population may be measured, for example, by calculating for a population the average length of survival following initiation of treatment with the solid form, pharmaceutically acceptable salt, or crystalline form thereof provided herein, or the pharmaceutical composition thereof provided herein. In an another embodiment, an increase in average survival time of a population may also be measured, for example, by calculating for a population the average length of survival following completion of a first round of treatment with the solid form, pharmaceutically acceptable salt, or crystalline form thereof provided herein, or the pharmaceutical composition thereof provided herein.

In some embodiments, treating a disease or condition described herein with the solid form, pharmaceutically acceptable salt, or crystalline form thereof provided herein, or the pharmaceutical composition thereof provided herein, results in a decrease in the mortality rate of a population of treated subjects in comparison to a population of subjects receiving a carrier alone. In another embodiment, treating a disease or condition described herein with the solid form, pharmaceutically acceptable salt, or crystalline form thereof provided herein, or the pharmaceutical composition thereof provided herein, results in a decrease in the mortality rate of ;a population of treated subjects in comparison to an untreated population. In a further embodiment, treating a disease or condition described herein with the solid form, pharmaceutically acceptable salt, or crystalline form thereof provided herein, or the pharmaceutical composition thereof described herein, results in a decrease in the mortality rate of a population of treated subjects in comparison to a population receiving monotherapy with a drug that is not a solid form, pharmaceutically acceptable salt, or crystalline form thereof provided herein, or a pharmaceutical composition thereof provided herein. Preferably, the mortality rate is decreased by more than about 2%; more preferably, by more than about 5%; more preferably, by more than about 10%; and most preferably, by more than about 25%.

In certain embodiments, treating a disease or condition described herein with the solid form, pharmaceutically acceptable salt, or crystalline form thereof provided herein, or the pharmaceutical composition thereof provided herein, results in a reduction in the rate of cellular proliferation. Preferably, after treatment with the solid form, pharmaceutically acceptable salt, or crystalline form thereof provided herein, or the pharmaceutical composition thereof provided herein, the rate of cellular proliferation is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The rate of cellular proliferation may be measured by any reproducible means of measurement. In some embodiments, the rate of cellular proliferation is measured, for example, by measuring the number of dividing cells in a tissue sample per unit time.

In another embodiment, treating a disease or condition described herein with the solid form, pharmaceutically acceptable salt, or crystalline form thereof provided herein, or the pharmaceutical composition thereof provided herein, results in a reduction in the proportion of proliferating cells. Preferably, after treatment with the solid form, pharmaceutically acceptable salt, or crystalline form thereof provided herein, or the pharmaceutical composition thereof provided herein, the proportion of proliferating cells is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The proportion of proliferating cells may be measured by any reproducible means of measurement. In some embodiments, the proportion of proliferating cells is measured, for example, by quantifying the number of dividing cells relative to the number of nondividing cells in a tissue sample. In another embodiment, the proportion of proliferating cells is equivalent to the mitotic index.

In another embodiment, treating a disease or condition described herein with the solid form, pharmaceutically acceptable salt, or crystalline form thereof provided herein, or the pharmaceutical composition thereof provided herein, results in a decrease in size of an area or zone of cellular proliferation. Preferably, after treatment with the solid form, pharmaceutically acceptable salt, or crystalline form thereof provided herein, or the pharmaceutical composition thereof provided herein, the size of an area or zone of cellular proliferation is reduced by at least 5% relative to its size prior to treatment; more preferably, reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. Size of an area or zone of cellular proliferation may be measured by any reproducible means of measurement. In some embodiments, size of an area or zone of cellular proliferation may be measured as a diameter or width of an area or zone of cellular proliferation.

Depending on the disease to be treated and the subject's condition, the solid form, pharmaceutically acceptable salt, or crystalline form thereof provided herein, or the pharmaceutical composition thereof provided herein, such as for example the ethanolamine salt of (E)-2-[[3-(3-methoxy-4-propargyloxy)phenyl)-1-oxo-2-propenyl]amino]benzoic acid or a solid or a crystalline form thereof provided herein, or pharmaceutical composition thereof provided herein, may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration and may be formulated, alone or together, in suitable dosage unit with pharmaceutically acceptable carriers, adjuvants and vehicles appropriate for each route of administration. Also provided is administration of the solid form, pharmaceutically acceptable salt, or crystalline form thereof provided herein, or the pharmaceutical composition thereof provided herein, such as for example the ethanolamine salt of (E)-2-[[3-(3-methoxy-4-propargyloxy)phenyl)-1-oxo-2-propenyl]amino]benzoic acid or a solid or a crystalline form thereof provided herein, or the pharmaceutical composition thereof provided herein, in a depot formulation, in which the active ingredient is released over a predefined time period.

In the context of the methods provided herein, a therapeutically or prophylactically effective amount of the solid form, pharmaceutically acceptable salt, or crystalline form thereof provided herein, or the pharmaceutical composition thereof provided herein, such as for example the ethanolamine salt of (E)-2-[[3-(3-methoxy-4-propargyloxy)phenyl)-1-oxo-2-propenyl]amino]benzoic acid or a solid or a crystalline form thereof provided herein, or the pharmaceutical composition thereof provided herein, can be readily determined by one of ordinary skill in the art, by the use of conventional techniques and by observing results obtained under analogous circumstances. In determining the therapeutically effective amount a number of factors are to be considered including but not limited to, the species of subject, its size, age and general health, the specific condition involved, the severity of the condition, the response of the subject to treatment, the mode of administration, the bioavailability of the preparation administered, the dose regime selected, the use of other medications, and other relevant circumstances.

One skilled in the art would be able, by routine experimentation, to determine an effective, non-toxic amount of the solid form, pharmaceutically acceptable salt, or crystalline form thereof provided herein, or the pharmaceutical composition thereof provided herein, such as for example the ethanolamine salt of (E)-2-[[3-(3-methoxy-4-propargyloxy)phenyl)-1-oxo-2-propenyl]amino]benzoic acid or a solid or a crystalline form thereof provided herein, or the pharmaceutical composition thereof provided herein, which would be required for the treatment, prevention, or amelioration of a fibrotic, inflammatory or proliferative disease or condition described herein.

In some embodiments, a therapeutically effective dosage level of the solid form, pharmaceutically acceptable salt, or crystalline form thereof provided herein, or the pharmaceutical composition thereof provided herein, such as for example the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein, is in the range of about 0.01 to about 1000 mg per kilogram of body weight per day, or about 0.1 to about 100 mg per kilogram of body weight per day, or about 1 to about 10 mg per kilogram of body weight per day, or about 5 mg per kilogram of body weight per day. Small doses (0.01-1 mg/kg per day) may be administered initially, followed by increasing doses up to about 1000 mg/kg per day. In the event that the response in a subject is insufficient at such doses, even higher doses (or effective higher doses by a different, more localized delivery route) may be employed to the extent patient tolerance permits. A typical therapeutically or prophylactically effective amount of the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein may be in the range from 1 to 300 mg per kilogram of body weight per day, from 1 to 200 mg per kilogram of body weight per day, or from 1 to 100 mg per kilogram of body weight per day. A suitable dose can be administered in multiple sub-doses per day.

In some embodiments, an appropriate dosage level the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein suitable for the treatment, prevention, or amelioration of a fibrotic, inflammatory or proliferative disease or condition generally ranges from about 10 to about 5000, from about 100 to about 3000, or from about 200 to about 2500 mg per day (mg/day), which may be administered in single or multiple doses. Within this range the dosage may be about 150, about 200, about 250, about 300, about 350, about 400, about 450, about 500, about 600, about 700, about 800, about 900, about 1000, about 1100, about 1200, about 1300, about 1400, about 1500, about 1600, about 1700, about 1800, about 1900, about 2000, about 2100, about 2200, about 2300, about 2400, or about 2500 mg/day.

In certain embodiments, in the treatment, prevention, or amelioration of a fibrotic, inflammatory or proliferative disease or condition, an appropriate dosage level of the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein ranges from about 1 to about 100, about 1 to about 50, from about 2 to about 20, or from about 2 to about 10 mg per kg body weight per day (mg/kg/day), which may be administered in single or multiple doses. Within this range the dosage may be about 1, about 2, about 3, about 4, about 5, about 6, about 7, about 8, about 9, about 10, about 11, about 12, about 13, about 14, about 15, about 16, about 17, about 18, about 19, or about 20 mg/kg/day.

In certain embodiments, the pharmaceutically acceptable salt of (E)-2-[[3-(3-methoxy-4-propargyloxy)phenyl)-1-oxo-2-propenyl]amino]benzoic (e.g., the ethanolamine salt of (E)-2-[[3-(3-methoxy-4-propargyloxy)phenyl)-1-oxo-2-propenyl]amino]benzoic acid) or a solid or a crystalline form thereof provided herein, or the pharmaceutical compositions provided herein, are administered at a dose of between about 10 and about 400 mg/kg/day, or between about 50 and about 300 mg/kg/day, or between 100 and 250 mg/kg/day of (E)-2-[[3-(3-methoxy-4-propargyloxy)phenyl)-1-oxo-2-propenyl]amino]benzoic acid. In some embodiments, the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein, or the pharmaceutical compositions provided herein, are administered at a dose of about 100, about 110, about 120, about 130, about 140, about 150, about 160, about 170, about 180, about 190, about 200, about 210, about 220, about 230, about 240, about 250, about 260, about 270, about 280, about 290, or about 300 mg/kg/day of the compound of (E)-2-[[3-(3-methoxy-4-propargyloxy)phenyl)-1-oxo-2-propenyl]amino]benzoic acid.

For oral administration, the pharmaceutical compositions provided herein can be provided in the form of tablets containing from 10 to 10000 mg of the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein, particularly about 100, about 200, about 300, about 400, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, and about 1500 mg of the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof for the symptomatic adjustment of the dosage to the patient to be treated. The compositions may be administered on a regimen of 1 to 4 times per day, including once, twice, three times, and four times per day.

In certain embodiments, for oral administration, the pharmaceutical compositions provided herein can be provided in the form of tablets containing from 1 to 100 mg of the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein, particularly about 1, about 2, about 3, about 4, about 5, about 6, about 7, about 8, about 9, about 10, about 11, about 12, about 13, about 14, about 15, about 16, about 17, about 18, about 19, or about 20 mg of the active ingredient for the symptomatic adjustment of the dosage to the patient to be treated. The compositions may be administered on a regimen of 1 to 4 times per day, including once, twice, three times, and four times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, and diet of the patient, mode and time of administration, rate of excretion, drug combination, and the severity of the particular condition.

In certain embodiments, provided herein also are kits which, when used by the medical practitioner, can simplify the administration of appropriate amounts of the solid form, pharmaceutically acceptable salt, or crystalline form thereof provided herein, or the pharmaceutical composition thereof provided herein, such as for example the pharmaceutically acceptable salt of (E)-2-[[3-(3-methoxy-4-propargyloxy) phenyl)-1-oxo-2-propenyl]amino]benzoic acid (e.g., the ethanolamine salt of (E)-2-[[3-(3-methoxy-4-propargyloxy) phenyl)-1-oxo-2-propenyl]amino]benzoic acid) or a solid or a crystalline form thereof provided herein, to a subject. In certain embodiments, the kit provided herein includes a container and a dosage form of the solid form, pharmaceutically acceptable salt, or crystalline form thereof provided herein, or the pharmaceutical composition thereof provided herein, such as for example the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein.

Kits provided herein can further include devices that are used to administer the solid form, pharmaceutically acceptable salt, or crystalline form thereof provided herein, or the pharmaceutical composition thereof provided herein, such as for example the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein. Examples of such devices include, but are not limited to, syringes, needle-less injectors drip bags, patches, and inhalers.

Kits provided herein can further include pharmaceutically acceptable vehicles that can be used to administer the solid form, pharmaceutically acceptable salt, or crystalline form thereof provided herein, or the pharmaceutical composition thereof provided herein, such as for example the pharmaceutically acceptable salt of (E)-2-[[3-(3-methoxy-4-propargyloxy)phenyl)-1-oxo-2-propenyl]amino]benzoic acid (e.g., the ethanolamine salt of (E)-2-[[3-(3-methoxy-4-propargyloxy)phenyl)-1-oxo-2-propenyl]amino]benzoic acid) or a solid or a crystalline form thereof provided herein. For example, if the solid form, pharmaceutically acceptable salt, or crystalline form thereof provided herein, or the pharmaceutical composition thereof provided herein, is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

Disclosed herein are the following numbered embodiments:

Embodiment 1: A solid form of (E)-2-[[3-(3-methoxy-4-propargyloxy)phenyl)-1-oxo-2-propenyl]amino]benzoic acid, or a salt thereof, having a water sorption of from 0.49% to 1.61% at 80% relative humidity as determined by dynamic vapor sorption.

Embodiment 2: A solid form of (E)-2-[[3-(3-methoxy-4-propargyloxy)phenyl)-1-oxo-2-propenyl]amino]benzoic acid, or a salt thereof, having an endothermic onset of from 29° C. to 187° C. as measured by differential scanning calorimetry.

Embodiment 3: A solid form of (E)-2-[[3-(3-methoxy-4-propargyloxy)phenyl)-1-oxo-2-propenyl]amino]benzoic acid, or a salt thereof, having a melting point of from 57° C. to 199° C. as measured by differential scanning calorimetry.

Embodiment 4: A solid form of (E)-2-[[3-(3-methoxy-4-propargyloxy)phenyl)-1-oxo-2-propenyl]amino]benzoic acid, or a salt thereof, having an endothermic onset of from 29° C. to 187° C., and a melting point of from 57° C. to 199° C., as measured by differential scanning calorimetry.

Embodiment 5: A solid form of (E)-2-[[3-(3-methoxy-4-propargyloxy)phenyl)-1-oxo-2-propenyl]amino]benzoic acid, or a salt thereof, having a weight loss of from 0.07% to 8.94%, or from 0.07% to 0.94% when heated from 25° C. to 120° C., as determined by thermogravimetric analysis.

Embodiment 6: A solid form of (E)-2-[[3-(3-methoxy-4-propargyloxy)phenyl)-1-oxo-2-propenyl]amino]benzoic acid, or a salt thereof, having a solubility of from 2.4 mg/ml to 5.14 mg/ml at 24 hours in FaSSIF media (pH 7.5).

Embodiment 7: A solid form of (E)-2-[[3-(3-methoxy-4-propargyloxy)phenyl)-1-oxo-2-propenyl]amino]benzoic acid, or a salt thereof, having a solubility of from 2.4 mg/ml to greater than 5.14 mg/ml at 24 hours in FaSSIF media (pH 7.5).

Embodiment 8: A solid form of (E)-2-[[3-(3-methoxy-4-propargyloxy)phenyl)-1-oxo-2-propenyl]amino]benzoic acid, or a salt thereof, having a solubility of from 1.2 mg/ml to 5.14 mg/ml at 24 hours in FeSSIF media (pH 7.8).

Embodiment 9: A solid form of (E)-2-[[3-(3-methoxy-4-propargyloxy)phenyl)-1-oxo-2-propenyl]amino]benzoic acid, or a salt thereof, having a solubility of from 1.2 mg/ml to greater than 5.14 mg/ml at 24 hours in FeSSIF media (pH 7.8).

Embodiment 10: A solid form of (E)-2-[[3-(3-methoxy-4-propargyloxy)phenyl)-1-oxo-2-propenyl]amino]benzoic acid, or a salt thereof, having a solubility of from 2.4 mg/ml to 5.14 mg/ml at 24 hours in FaSSIF media (pH 7.5), and a solubility of from 1.2 mg/ml to 5.14 mg/ml at 24 hours in FeSSIF media (pH 7.8).

Embodiment 11: A solid form of (E)-2-[[3-(3-methoxy-4-propargyloxy)phenyl)-1-oxo-2-propenyl]amino]benzoic acid, or a salt thereof, having a solubility of from 2.4 mg/ml to greater than 5.14 mg/ml at 24 hours in FaSSIF media (pH 7.5), and a solubility of from 1.2 mg/ml to greater than 5.14 mg/ml at 24 hours in FeSSIF media (pH 7.8).

Embodiment 12: A solid form of (E)-2-[[3-(3-methoxy-4-propargyloxy)phenyl)-1-oxo-2-propenyl]amino]benzoic acid, or a salt thereof, having a bioavailability of from 39 F % to 82 F %.

Embodiment 13: The solid form of embodiment 12, having a bioavailability of at least 50 F %, at least 55 F %, at least 60 F %, at least 65 F %, at least 70 F %, at least 75 F %, or at least 80 F %.

Embodiment 14: The solid form of any one of embodiments 1 to 13, wherein the solid form has any two or more of the following properties:

a water sorption of from 0.49% to 1.61% at 80% relative humidity as determined by dynamic vapor sorption;

an endothermic onset of from 29° C. to 187° C. as measured by differential scanning calorimetry;

a melting point of from 57° C. to 199° C. as measured by differential scanning calorimetry;

a weight loss of from 0.07% to 8.94%, or from 0.07% to 0.94%, when heated from 25° C. to 120° C. as determined by thermogravimetric analysis;

a solubility of from 2.4 mg/ml to 5.14 mg/ml at 24 hours in FaSSIF media (pH 7.5);

a solubility of from 2.4 mg/ml to greater than 5.14 mg/ml at 24 hours in FaSSIF media (pH 7.5);

a solubility of from 1.2 mg/ml to 5.14 mg/ml at 24 hours in FeSSIF media (pH 7.8);

a solubility of from 1.2 mg/ml to greater than 5.14 mg/ml at 24 hours in FeSSIF media (pH 7.8);

a bioavailability of from 39 F % to 82 F %.

Embodiment 15: The solid form of any one of embodiments 1 to 14, wherein the solid form is a crystalline form of (E)-2-[[3-(3-methoxy-4-propargyloxy)phenyl)-1-oxo-2-propenyl]amino]benzoic acid.

Embodiment 16: The solid form of any one of embodiments 1 to 15, wherein the solid form is a crystalline form of a salt of (E)-2-[[3-(3-methoxy-4-propargyloxy)phenyl)-1-oxo-2-propenyl]amino]benzoic acid.

Embodiment 17: The solid form of any one of embodiments 1 to 16, wherein the solid form is a crystalline form of a pharmaceutically acceptable salt of (E)-2-[[3-(3-methoxy-4-propargyloxy)phenyl)-1-oxo-2-propenyl]amino]benzoic acid.

Embodiment 18: A solid form of a salt of (E)-2-[[3-(3-methoxy-4-propargyloxy)phenyl)-1-oxo-2-propenyl]amino]benzoic acid having a water sorption of from 0.49% to 8.82% at 80% relative humidity as determined by dynamic vapor sorption.

Embodiment 19: A solid form of a salt of (E)-2-[[3-(3-methoxy-4-propargyloxy)phenyl)-1-oxo-2-propenyl]amino]benzoic acid having an endothermic onset of from 29° C. to 203° C. as measured by differential scanning calorimetry.

Embodiment 20: A solid form of a salt of (E)-2-[[3-(3-methoxy-4-propargyloxy)phenyl)-1-oxo-2-propenyl]amino]benzoic acid having a melting point of from 57° C. to 204° C. as measured by differential scanning calorimetry.

Embodiment 21: A solid form of a salt of (E)-2-[[3-(3-methoxy-4-propargyloxy)phenyl)-1-oxo-2-propenyl]amino]benzoic acid having an endothermic onset of from 29° C. to 203° C., and a melting point of from 57° C. to 204° C., as measured by differential scanning calorimetry.

Embodiment 22: A solid form of a salt of (E)-2-[[3-(3-methoxy-4-propargyloxy)phenyl)-1-oxo-2-propenyl]amino]benzoic acid having a weight loss of from 0.07% to 5.24% when heated from 25° C. to 120° C. as determined by thermogravimetric analysis.

Embodiment 23: A solid form of a salt of (E)-2-[[3-(3-methoxy-4-propargyloxy)phenyl)-1-oxo-2-propenyl]amino]benzoic acid having a solubility of from 2.4 mg/ml to 5.14 mg/ml at 24 hours in FaSSIF media (pH 7.5).

Embodiment 24: A solid form of a salt of (E)-2-[[3-(3-methoxy-4-propargyloxy)phenyl)-1-oxo-2-propenyl]amino]benzoic acid having a solubility of from 2.4 mg/ml to greater than 5.14 mg/ml at 24 hours in FaSSIF media (pH 7.5).

Embodiment 25: A solid form of a salt of (E)-2-[[3-(3-methoxy-4-propargyloxy)phenyl)-1-oxo-2-propenyl]amino]benzoic acid, having a solubility of from 1.2 mg/ml to 5.14 mg/ml at 24 hours in FeSSIF media (pH 7.8).

Embodiment 26: A solid form of a salt of (E)-2-[[3-(3-methoxy-4-propargyloxy)phenyl)-1-oxo-2-propenyl]amino]benzoic acid having a solubility of from 1.2 mg/ml to greater than 5.14 mg/ml at 24 hours in FeSSIF media (pH 7.8).

Embodiment 27: A solid form of a salt of (E)-2-[[3-(3-methoxy-4-propargyloxy)phenyl)-1-oxo-2-propenyl]amino]benzoic acid having a solubility of from 2.4 mg/ml to 5.14 mg/ml at 24 hours in FaSSIF media (pH 7.5), and a solubility of from 1.2 mg/ml to 5.14 mg/ml at 24 hours in FeSSIF media (pH 7.8).

Embodiment 28: A solid form of a salt of (E)-2-[[3-(3-methoxy-4-propargyloxy)phenyl)-1-oxo-2-propenyl]amino]benzoic acid having a solubility of from 2.4 mg/ml to greater than 5.14 mg/ml at 24 hours in FaSSIF media (pH 7.5), and a solubility of from 1.2 mg/ml to greater than 5.14 mg/ml at 24 hours in FeSSIF media (pH 7.8).

Embodiment 29: A solid form of a salt of (E)-2-[[3-(3-methoxy-4-propargyloxy)phenyl)-1-oxo-2-propenyl]amino]benzoic acid having a solubility of from 0.048 mg/ml to 0.090 mg/ml at 24 hours in media at pH 6.8.

Embodiment 30: A solid form of a salt of (E)-2-[[3-(3-methoxy-4-propargyloxy)phenyl)-1-oxo-2-propenyl]amino]benzoic acid having a bioavailability of from 39 F % to 82 F %.

Embodiment 31: The solid form of embodiment 30, having a bioavailability of at least 50 F %, at least 55 F %, at least 60 F %, at least 65 F %, at least 70 F %, at least 75 F %, or at least 80 F %.

Embodiment 32: The solid form of any one of embodiments 18 to 31, wherein the solid form has any two or more of the following properties:

a water sorption of from 0.49% to 8.82% at 80% relative humidity as determined by dynamic vapor sorption;

an endothermic onset of from 29° C. to 203° C. as measured by differential scanning calorimetry;

a melting point of from 57° C. to 204° C. as measured by differential scanning calorimetry;

a weight loss of from 0.07% to 5.24% when heated from 25° C. to 120° C. as determined by thermogravimetric analysis;

a solubility of from 2.4 mg/ml to 5.14 mg/ml at 24 hours in FaSSIF media (pH 7.5);

a solubility of from 2.4 mg/ml to greater than 5.14 mg/ml at 24 hours in FaSSIF media (pH 7.5);

a solubility of from 1.2 mg/ml to 5.14 mg/ml at 24 hours in FeSSIF media (pH 7.8);

a solubility of from 1.2 mg/ml to greater than 5.14 mg/ml at 24 hours in FeSSIF media (pH 7.8);

a solubility of from 0.048 mg/ml to 0.090 mg/ml at 24 hours in media at pH 6.8;

a bioavailability of from 39 F % to 82 F %.

Embodiment 33: The solid form of any one of embodiments 18 to 32, wherein the solid form is a crystalline form of a salt of (E)-2-[[3-(3-methoxy-4-propargyloxy)phenyl)-1-oxo-2-propenyl]amino]benzoic acid.

Embodiment 34: The solid form of any one of embodiments 18 to 33, wherein the solid form is a crystalline form of a pharmaceutically acceptable salt of (E)-2-[[3-(3-methoxy-4-propargyloxy)phenyl)-1-oxo-2-propenyl]amino]benzoic acid.

Embodiment 35: The solid form of any one of embodiments 18 to 34, wherein the solid form is a crystalline form of a pharmaceutically acceptable salt of (E)-2-[[3-(3-methoxy-4-propargyloxy)phenyl)-1-oxo-2-propenyl]amino]benzoic acid selected from the group consisting of: a potassium salt, a meglumine salt, a tris(hydroxymethyl)aminomethane salt, an ethanolamine salt, a tert-butylamine salt, an ammonium salt, and a lysine salt of (E)-2-[[3-(3-methoxy-4-propargyloxy)phenyl)-1-oxo-2-propenyl]amino] benzoic acid.

Embodiment 36: The solid form of any one of embodiments 18 to 35, wherein the solid form is a crystalline form of a pharmaceutically acceptable salt of (E)-2-[[3-(3-methoxy-4-propargyloxy)phenyl)-1-oxo-2-propenyl]amino] benzoic acid selected from the group consisting of: a meglumine salt, a tris(hydroxymethyl)aminomethane salt, an ethanolamine salt, and a tert-butylamine salt of (E)-2-[[3-(3-methoxy-4-propargyloxy)phenyl)-1-oxo-2-propenyl] amino]benzoic acid.

Embodiment 37: The solid form of any one of embodiments 18 to 36, wherein the solid form is a crystalline form of an ethanolamine salt of (E)-2-[[3-(3-methoxy-4-propargyloxy)phenyl)-1-oxo-2-propenyl]amino]benzoic acid.

Embodiment 38: A crystalline form of a pharmaceutically acceptable salt of the compound of Formula (I):

Formula (I)

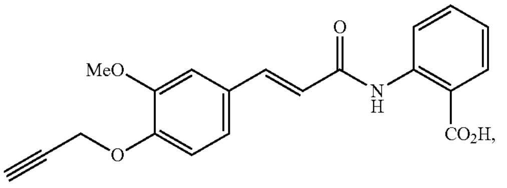

wherein the crystalline form has a water sorption of less than 1.7% at 25° C. and 80% relative humidity as determined by dynamic vapor sorption.

Embodiment 39: The crystalline form according to embodiment 38, wherein the crystalline form has a weight loss of from 0.07% to 8.94%, or from 0.07% to 0.94%, when heated from 25° C. to 120° C. as determined by thermogravimetric analysis.

Embodiment 40: The crystalline form according to embodiment 38, wherein the crystalline form has a solubility of from 2.5 mg/ml to greater than 5.0 mg/ml at 24 hours in FaSSIF media (pH 7.5).

Embodiment 41: The crystalline form according to embodiment 38, wherein the crystalline form has a solubility of from 3.4 mg/ml to greater than 5.0 mg/ml at 24 hours in FeSSIF media (pH 7.8).

Embodiment 42: The crystalline form according to embodiment 38, wherein the crystalline form has a solubility of from 0.07 mg/ml to 0.090 mg/ml at 24 hours in media at pH 6.8.

Embodiment 43: The crystalline form according to embodiment 38, wherein the crystalline form has bioavailability of from 39 F % to 82 F %.

Embodiment 44: The crystalline form according to embodiment 38, wherein the pharmaceutically acceptable salt is selected from the group consisting of: a meglumine salt, an ethanolamine salt, a tris(hydroxymethyl)aminomethane salt, and a tert-butylamine salt.

Embodiment 45: A pharmaceutical composition comprising the crystalline form according to embodiment 38 and at least one pharmaceutically acceptable excipient.

Embodiment 46: A crystalline form of a pharmaceutically acceptable salt of the compound of Formula (I):

Formula (I)

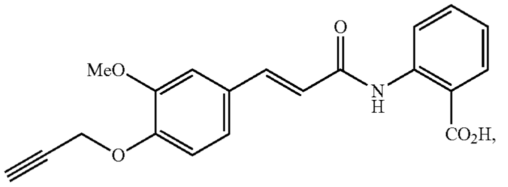

wherein the crystalline form has a bioavailability of from 39 F % to 82 F %.

Embodiment 47: The crystalline form according to embodiment 46, wherein the pharmaceutically acceptable salt is selected from the group consisting of: a potassium salt, a meglumine salt, an ethanolamine salt, a tris(hydroxymethyl)aminomethane salt, a tert-butylamine salt, an ammonium salt, and a lysine salt.

Embodiment 48: The crystalline form according to embodiment 46, wherein the crystalline form has a bioavailability of from 50 F % to 82 F %.

Embodiment 49: The crystalline form according to embodiment 46, wherein the crystalline form has a bioavailability of from 64 F % to 82 F %.

Embodiment 50: A pharmaceutical composition comprising the crystalline form according to embodiment 46 and at least one pharmaceutically acceptable excipient.

Embodiment 51: A crystalline form of an ethanolamine salt of the compound of Formula (I):

Formula (I)

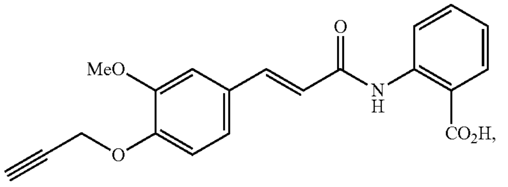

wherein the crystalline form has a bioavailability of at least about 1.5× compared to bioavailability of the free form of the compound of Formula (I).

Embodiment 52: The crystalline form according to embodiment 51, wherein the crystalline form has a bioavailability of at least about 2× compared to bioavailability of the free form of the compound of Formula (I).

Embodiment 53: The crystalline form according to embodiment 51, wherein the crystalline form has a bioavailability of from 82 F %.

Embodiment 54: The crystalline form according to embodiment 51, wherein the crystalline form has a water sorption of 0.49% at 25° C. and 80% relative humidity as determined by dynamic vapor sorption.

Embodiment 55: The crystalline form according to embodiment 51, wherein the crystalline form has an endothermic onset of 176° C. as measured by differential scanning calorimetry.

Embodiment 56: The crystalline form according to embodiment 51, wherein the crystalline form has a melting point of 178° C. as measured by differential scanning calorimetry.

Embodiment 57: The crystalline form according to embodiment 51, wherein the crystalline form has a weight loss of 0.10% when heated from 25° C. to 120° C. as determined by thermogravimetric analysis.

Embodiment 58: The crystalline form according to embodiment 51, wherein the crystalline form has a solubility of greater than 7.99 mg/ml at 24 hours in FaSSIF media (pH 7.5).

Embodiment 59: The crystalline form according to embodiment 51, wherein the crystalline form has a solubility of greater than 8.02 mg/ml at 24 hours in FeSSIF media (pH 7.8).

Embodiment 60: The crystalline form according to embodiment 51, wherein the crystalline form has a solubility of 0.088 mg/ml at 24 hours in media at pH 6.8.

Embodiment 61: A pharmaceutical composition comprising the crystalline form according to embodiment 51 and at least one pharmaceutically acceptable excipient.

Embodiment 62: A crystalline form of an ethanolamine salt of the compound of Formula (I):

Formula (I)

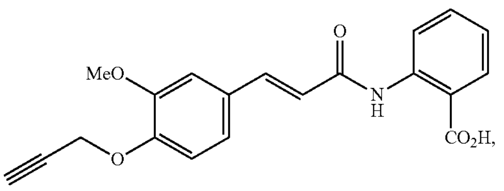

wherein the crystalline form exhibits an X-ray powder diffraction pattern having at least one peak selected from 6.6±0.2, 11.7±0.2, 15.0±0.2, 15.9±0.2, 17.7±0.2, 18.7±0.2, 19.2±0.2, 23.7±0.2, and 26.6±0.2 degrees 2θ.

Embodiment 63: The crystalline form according to embodiment 62, wherein the crystalline form exhibits an X-ray powder diffraction pattern having at least two peaks selected from 6.6±0.2, 11.7±0.2, 15.0±0.2, 15.9±0.2, 17.7±0.2, 18.7±0.2, 19.2±0.2, 23.7±0.2, and 26.6±0.2 degrees 2θ.

Embodiment 64: The crystalline form according to embodiment 62, wherein the crystalline form exhibits an X-ray powder diffraction pattern having at least three peaks selected from 6.6±0.2, 11.7±0.2, 15.0±0.2, 15.9±0.2, 17.7±0.2, 18.7±0.2, 19.2±0.2, 23.7±0.2, and 26.6±0.2 degrees 2θ.

Embodiment 65: The crystalline form according to embodiment 62, wherein the crystalline form exhibits an X-ray powder diffraction pattern having at least four peaks selected from 6.6±0.2, 11.7±0.2, 15.0±0.2, 15.9±0.2, 17.7±0.2, 18.7±0.2, 19.2±0.2, 23.7±0.2, and 26.6±0.2 degrees 2θ.

Embodiment 66: The crystalline form according to embodiment 62, wherein the crystalline form exhibits an X-ray powder diffraction pattern having at least five peaks selected from 6.6±0.2, 11.7±0.2, 15.0±0.2, 15.9±0.2, 17.7±0.2, 18.7±0.2, 19.2±0.2, 23.7±0.2, and 26.6±0.2 degrees 2θ.

Embodiment 67: The crystalline form according to embodiment 62, wherein the crystalline form exhibits an X-ray powder diffraction pattern having at least one peak selected from 6.6±0.2, 11.7±0.2, 15.0±0.2, 15.9±0.2, 17.7±0.2, 18.7±0.2 and 19.2±0.2 degrees 2θ.

Embodiment 68: The crystalline form according to embodiment 62, wherein the crystalline form exhibits an X-ray powder diffraction pattern having at least two peaks selected from 6.6±0.2, 11.7±0.2, 15.0±0.2, 15.9±0.2, 17.7±0.2, 18.7±0.2 and 19.2±0.2 degrees 2θ.

Embodiment 69: The crystalline form according to embodiment 62, wherein the crystalline form exhibits an X-ray powder diffraction pattern having at least three peaks selected from 6.6±0.2, 11.7±0.2, 15.0±0.2, 15.9±0.2, 17.7±0.2, 18.7±0.2 and 19.2±0.2 degrees 2θ.

Embodiment 70: A crystalline form of an ethanolamine salt of the compound of Formula (I):

Formula (I)

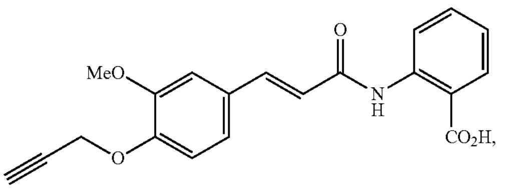

wherein the crystalline form exhibits an X-ray powder diffraction pattern comprising peaks at 6.6±0.2, 11.7±0.2, 15.0±0.2, 15.9±0.2, 17.7±0.2, 18.7±0.2 and 19.2±0.2 degrees 2θ.

Embodiment 71: A crystalline form of an ethanolamine salt of the compound of Formula (I):

Formula (I)

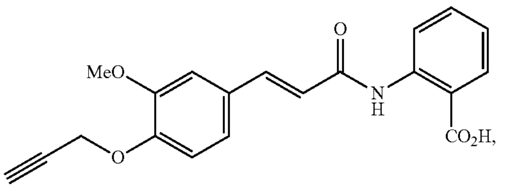

wherein the crystalline form exhibits an X-ray powder diffraction pattern comprising peaks at 6.6±0.2, 11.7±0.2, 15.0±0.2, 15.9±0.2, 17.7±0.2, 18.7±0.2, 19.2±0.2, 23.7±0.2, and 26.6±0.2 degrees 2θ.

Embodiment 72: Form I crystalline ethanolammonium (E)-2-[[3-(3-Methoxy-4-propargyloxy)phenyl)-1-oxo-2-propenyl]amino]benzoate.

Embodiment 73: A pharmaceutical composition comprising the crystalline form according to any one of embodiments 62 to 72, and a pharmaceutically acceptable carrier.

Embodiment 74: A pharmaceutical composition comprising the solid form or crystalline form according to any one of embodiments 1 to 72, and a pharmaceutically acceptable excipient.

Embodiment 75: The pharmaceutical composition according to embodiment 73 or embodiment 74, wherein the pharmaceutical composition is formulated for single dose administration.

Embodiment 76: The pharmaceutical composition according to any one of embodiments 73 to 75, wherein the pharmaceutical composition is formulated as an oral, parenteral, or intravenous dosage form.

Embodiment 77: The pharmaceutical composition according to any one of embodiments 73 to 76, wherein the pharmaceutical composition is formulated as an oral dosage form.

Embodiment 78: The pharmaceutical composition according to embodiment 77, wherein the oral dosage form is a tablet or capsule.

Embodiment 79: The pharmaceutical composition according to any one of embodiments 73 to 78, wherein the pharmaceutical composition comprises from about 1 to about 2000 mg of the solid form or crystalline form according to any one of embodiments 1 to 72.

Embodiment 80: The pharmaceutical composition according to any one of embodiments 73 to 79, wherein the pharmaceutical composition comprises about 50, about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 mg of the solid form or crystalline form according to any one of embodiments 1 to 72.

Embodiment 81: The pharmaceutical composition according to any one of embodiments 73 to 79, wherein the pharmaceutical composition comprises about 20, about 30, about 40, about 50, about 100, about 150, about 200, about 250, about 300, about 350, or about 400 mg of the solid form or crystalline form according to any one of embodiments 1 to 72.

Embodiment 82: The pharmaceutical composition according to any one of embodiments 73 to 79, wherein the pharmaceutical composition comprises about 1, about 2, about 3, about 4, about 5, about 6, about 7, about 8, about 9, about 10, about 11, about 12, about 13, about 14, about 15, about 16, about 17, about 18, about 19, or about 20 mg of the solid form or crystalline form according to any one of embodiments 1 to 72.

Embodiment 83: The pharmaceutical composition according to any one of embodiments 73 to 78, wherein the pharmaceutical composition comprises the solid form or crystalline form according to any one of embodiments 1 to 72 in an amount effective to provide a dose of from about 1 mg/kg to about 500 mg/kg of the compound of Formula (I).

Embodiment 84: The pharmaceutical composition according to embodiment 83, wherein the pharmaceutical composition comprises the solid form or crystalline form according to any one of embodiments 1 to 72 in an amount effective to provide a dose of about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, or about 400 mg/kg of the compound of Formula (I).

Embodiment 85: The pharmaceutical composition according to embodiment 83 or embodiment 84, wherein the pharmaceutical composition comprises the solid form or crystalline form according to any one of embodiments 1 to 72 in an amount effective to provide a dose of between about 10 and about 400 mg/kg, or between about 50 and about 300 mg/kg, or between about 100 and about 250 mg/kg of the compound of Formula (I).

Embodiment 86: The pharmaceutical composition according to any one of embodiments 83 to 85, wherein the pharmaceutical composition comprises the solid form or crystalline form according to any one of embodiments 1 to 72 in an amount effective to provide a dose of about 200 mg/kg of the compound of Formula (I).

Embodiment 87: The pharmaceutical composition according to any one of embodiments 73 to 78, wherein the pharmaceutical composition comprises the solid form or crystalline form according to any one of embodiments 1 to 72 in an amount effective to provide a concentration of from 10 UM to 200 μM, or from 10 μM to 100 μM, or from 10 μM to 50 μM of the compound of Formula (I) at a site of its action.

Embodiment 88: The pharmaceutical composition according to any one of embodiments 73 to 78, wherein the pharmaceutical composition comprises the solid form or crystalline form according to any one of embodiments 1 to 72 in an amount effective to provide a concentration of about 20 to about 40 μM, about 25 to about 35 μM, or about 30 μM of the compound of Formula (I) at a site of its action.

Embodiment 89: A pharmaceutical composition comprising the ethanolamine salt of (E)-2-[[3-(3-methoxy-4-propargyloxy)phenyl)-1-oxo-2-propenyl]amino]benzoic acid and at least one pharmaceutically acceptable carrier, wherein at least about 80% of the ethanolamine salt of (E)-2-[[3-(3-methoxy-4-propargyloxy)phenyl)-1-oxo-2-propenyl]amino]benzoic acid is crystalline Form I of the ethanolamine salt of (E)-2-[[3-(3-methoxy-4-propargyloxy)phenyl)-1-oxo-2-propenyl]amino]benzoic acid.

Embodiment 90: The pharmaceutical composition according to Embodiment 89, wherein at least 85%, at least 88%, at least 90%, at least 91%, at least 92%, at least 93%, at least 94%, or at least 95% of the ethanolamine salt of (E)-2-[[3-(3-methoxy-4-propargyloxy)phenyl)-1-oxo-2-propenyl]amino]benzoic acid is crystalline Form I of the ethanolamine salt of (E)-2-[[3-(3-methoxy-4-propargyloxy)phenyl)-1-oxo-2-propenyl]amino]benzoic acid.

Embodiment 91: The pharmaceutical composition according to Embodiment 90, wherein at least 96%, at least 97%, at least 98%, or at least 99% of the ethanolamine salt of (E)-2-[[3-(3-methoxy-4-propargyloxy)phenyl)-1-oxo-2-propenyl]amino]benzoic acid is crystalline Form I of the ethanolamine salt of (E)-2-[[3-(3-methoxy-4-propargyloxy)phenyl)-1-oxo-2-propenyl]amino]benzoic acid.

Embodiment 92: The pharmaceutical composition according to Embodiment 91, wherein at least 99.5% or at least 99.9% of the ethanolamine salt of (E)-2-[[3-(3-methoxy-4-propargyloxy)phenyl)-1-oxo-2-propenyl]amino]benzoic acid is crystalline Form I of the ethanolamine salt of (E)-2-[[3-(3-methoxy-4-propargyloxy)phenyl)-1-oxo-2-propenyl]amino]benzoic acid.

Embodiment 93: A method of treating, preventing, or ameliorating a fibrotic, inflammatory or proliferative disease or condition in a subject, comprising administering to the subject a therapeutically effective amount of the solid form or crystalline form according to any one of embodiments 1 to 72, or the pharmaceutical composition according to any one of embodiments 73 to 92.

Embodiment 94: The method according to embodiment 93, wherein the fibrotic, inflammatory or proliferative disease or condition is selected from fibrosis of skin, lung, heart, kidney, pancreas, eye and liver.

Embodiment 95: The method according to embodiment 93, wherein the fibrotic, inflammatory or proliferative disease or condition is selected from diabetic cardiomyopathy, congestive heart failure, ischemic heart disease, hypertension, peripheral artery disease, cerebrovascular disease, kidney disease, systemic sclerosis (scleroderma), hypertrophic scars, keloids, pulmonary fibrosis, non-alcoholic steatohepatitis (NASH), non-alcoholic fatty liver disease (NAFLD), primary biliary cirrhosis (PBC), and primary sclerosis cholangitis (PSC).

Embodiment 96: The method according to embodiment 93, wherein the fibrotic, inflammatory or proliferative disease or condition is a kidney disease.

Embodiment 97: The method according to embodiment 93, wherein the fibrotic, inflammatory or proliferative disease or condition is selected from chronic kidney disease, progressive kidney disease, diabetic nephropathy, diabetic kidney disease, glomerulonephritis, focal segmental glomerulosclerosis, systemic lupus, lupus nephritis, primary glomerulonephritis, membranous Is nephropathy, membranoproliferative glomerulonephritis, diffuse proliferative glomerulonephritis, membranous focal segmental glomerulosclerosis, secondary glomerulonephritis, membranous nephropathy, IgA nephropathy, or ischemic nephropathy.

Embodiment 98: The method according to embodiment 93, wherein the fibrotic, inflammatory or proliferative disease or condition is chronic kidney disease.

Embodiment 99: The method according to embodiment 93, wherein the fibrotic, inflammatory or proliferative disease or condition is diabetic nephropathy.

Embodiment 100: The method according to embodiment 93, wherein the fibrotic, inflammatory or proliferative disease or condition is focal segmental glomerulosclerosis.

Embodiment 101: The method according to embodiment 93, wherein the fibrotic, inflammatory or proliferative disease or condition is diabetic cardiomyopathy, congestive heart failure, or ischemic heart disease.

Embodiment 102: The method according to embodiment 93, wherein the fibrotic, inflammatory or proliferative disease or condition is systemic sclerosis or Scleroderma.

Embodiment 103: The method according to embodiment 93, wherein the fibrotic, inflammatory or proliferative disease or condition is pulmonary fibrosis.

Embodiment 104: The method according to embodiment 103, wherein the pulmonary fibrosis is idiopathic pulmonary fibrosis (IPF).

Embodiment 105: The method according to embodiment 93, wherein the fibrotic, inflammatory or proliferative disease or condition is selected from chronic obstructive pulmonary disorder (COPD), asthma, and cystic fibrosis.

Embodiment 106: The method according to embodiment 93, wherein the fibrotic, inflammatory or proliferative disease or condition is a fibrotic eye disease.

Embodiment 107: The method according to embodiment 106, wherein the fibrotic eye disease is selected from diabetic retinopathy, wet age related macular degeneration, and diabetic macular edema.

Embodiment 108: The method according to embodiment 93, wherein the fibrotic, inflammatory or proliferative disease or condition is a cancer.

Embodiment 109: The method according to embodiment 108, wherein the cancer is selected from a breast cancer, skin cancer (melanoma), pancreatic cancer, lung cancer, prostate cancer, colon cancer, liver cancer (hepatocellular carcinoma), head and neck cancer, ovarian cancer and kidney cancer.

Embodiment 110: The method according to embodiment 93, wherein the fibrotic, inflammatory or proliferative disease or condition is selected from diabetic retinopathy, diabetic macular edema, macular degeneration, retinopathy of prematurity (ROP), and proliferative vitreoretinopathy (PVR).

Embodiment 111: The method according to embodiment 93, wherein the fibrotic, inflammatory or proliferative disease or condition is an autoimmune disease or condition.

Embodiment 112: The method according to embodiment 111, wherein the autoimmune disease or condition is selected from systemic lupus erythematosus (SLE), inflammatory bowel disease, Crohn's disease, ulcerative colitis, graft versus host disease, multiple sclerosis, and rheumatoid arthritis.

Embodiment 113: The method according to any one of embodiments 93 to 112, wherein the solid form or crystalline form, or the pharmaceutical composition, is administered orally.

Embodiment 114: The method according to any one of embodiments 93 to 113, wherein the solid form or crystalline form, or the pharmaceutical composition, is administered daily.

Embodiment 115: The method according to any one of embodiments 93 to 114, wherein the solid form or crystalline form, or the pharmaceutical composition, is administered at a dose of between about 10 and about 400 mg/kg/day, or between about 50 and about 300 mg/kg/day, or between 100 and 250 mg/kg/day of the compound of Formula (I).

Embodiment 116: The method according to any one of embodiments 93 to 115, wherein the solid form or crystalline form, or the pharmaceutical composition, is administered at a dose of about 200 mg/kg/day of the compound of Formula (I).

Embodiment 117: The method according to any one of embodiments 93 to 116, wherein the subject is a human.

EXAMPLES

The present disclosure is further described by the following examples, which are not intended to limit the scope of the claims.

Example 1. General Experimental

Regents and Materials

All inorganic reagents, organic solvents and water are at least of the standard of analytical laboratory reagent grade.

Instruments

| Instrument | Manufacturer | Model |
|---|---|---|
| Analytical balance | Sartorius | CP225D |
| XRPD (X-ray Powder Diffractometer) | Shimadzu | XRD-6000 |
| DSC (Differential Scanning Calorimeter) | Mettler Toledo | DSC3 |
| TGA (Thermogravimetric Analysis) | Perkin Elmer | Pyris1 TGA |
| PLM (Polarized Light Microscope) | Shanghai Changfang Optical | XPV-203E |
| DVS (Dynamic vapor absorption) | Surface Measurement Systems (SMS) | DVS Intrinsic |
| Constant temperature magnetic stirrer | Shanghai Sile Instrument Co. | B13-3 |
| Ultrasonic bath | Shanghai Kudos | SK8300BT |
| Centrifuge | Hunan Kecheng | H4-20K |
| HPLC (High Performance Liquid Chromatograph) | Agilent | Agilent 1260 |
| Nuclear Magnetic Resonance (NMR) | Bruker | AVANCE III (400M). |

Instrumental Parameters

X-Ray Powder Diffraction (XRPD)

The X-ray powder diffraction (XRPD) pattern was obtained on a Shimadzu XRD-6000 instrument. The XRPD bulk pattern was measured at room temperature. Samples were run on XRPD using below method:

| Setting | Parameters |
|---|---|
| Tube: | Cu: K- Alpha (λ = 1.54056 Å) |
| Generator: | Voltage: 40 kV; Current: 30 mA |
| Scan Scope: | 2 to 50 deg 2θ. Scanning rate: 5 deg/min |

Differential Scanning calorimetry (DSC)

Approximately 1 mg of sample was tested in a pinhole aluminium pans under nitrogen purge using a ramp rate of 20° C./min over the range 30° C.-300° C. (the test range was adjusted according to the decomposition temperature of sample).

| Setting | Parameters |
|---|---|
| Ramp rate | 20° C./min over the range 30° C. to 300° C. |
| Nitrogen purge | 50 mL/min |
| Samples | About 1 mg |

Thermogravimetric Analysis (TGA)

Samples of compounds (4~6 mg) were weighed into the pan, and heated under nitrogen purge using a ramp rate of 20° C./min over the range of 30° C. to 350° C., and then held at 350° C. for a further 1 min.

| Setting | Parameters |
|---|---|
| Ramp rate | 20° C./min over the range 30° C. to 350° C., hold for 1 min at 350° C. |
| Nitrogen purge | 50 mL/min |
| Samples | About 5 mg |

Dynamic Vapor Sorption (DVS)

Approximately 10 mg of sample was used to test the moisture sorption/desorption profiles at 25° C. during a 0% to 95% to 0% relative humidity (RH) cycle with the following parameters:

| Setting | Parameters |
|---|---|
| Temperature | 25° C. |
| Equilibrium | dm/dt: 0.01%/min |
| RH (%) measurement step scope: | 0% to 95% to 0% RH |
| RH (%) measurement step: | 5% RH |
| Samples | 10 mg |

During DVS analysis, the humidity is held at each value during the 0% to 95% to 0% RH cycle, changing with increments of 5% RH and the change in mass measured at each such value. For example, the sample is subjected to an increase in relative humidity from 25% RH to 30% RH, and any consequent mass change is measured. The humidity is held constant at 30% RH until the mass change of the sample reaches equilibrium, as determined by the rate of change of weight being 0.01%/minute or less. The humidity is then changed to the next step value and the consequent mass change measured, and so on. The moisture-response profile is therefore observed over the range of conditions of the 0% to 95% to 0% RH cycle but a standard comparison may be provided by the moisture content value at a set condition, such as at 80% RH. Table 11 lists hygroscopicity values for relevant samples in the sorption cycle by reciting the water content at mass equilibrium measured at 80% RH during the ramp up from 0 to 95% RH.

Therefore, where hygroscopicity values are reported herein at a particular humidity, they refer to values, taken at the stated humidity level, which were measured during the sorption cycle of increasing humidity from 0% RH to 95% RH, prior to return to 0% RH. The hygroscopicity values recited herein refer to total water gain since the start of the experiment only and so may not necessarily be equivalent to the actual total water content of the sample.

Hygroscopicity of samples was classified as follows:

| Hygroscopicity Classification | Water Sorption Criterion* |
|---|---|
| Deliquescent | Sufficient water is absorbed to form a liquid |
| Very hygroscopic | W % ≥ 15% |
| Hygroscopic | W % ≥ 2% |
| Slightly hygroscopic | W % ≥ 0.2% |
| Non-hygroscopic | W % < 0.2% |

*At 25 ± 1° C. and 80 ± 2% relative humidity (RH) (European Pharmacopoeia 10.0); W: The amount of moisture adsorbed from 0% RH to 80% RH.

Polarized Light Microscopy (PLM)

Samples dispersed in silicone oil were observed using ocular lens (10×) and objective lens (40×) under crossed polarizers, and recorded by camera/computer system with magnification scale.

$^1$H Nuclear Magnetic Resonance (NMR)

Approximately 3 mg of sample was weighed out into the nuclear magnetic tube and 0.5 mL deuterated dimethyl sulfoxide or deuterated methanol was added to dissolve the sample completely.

Solubility Measurement

Approximately 8-12 mg of salts of (E)-2-[[3-(3-methoxy-4-propargyloxy)phenyl)-1-oxo-2-propenyl]amino]benzoic acid (equimolar to 8 mg of (E)-2-[[3-(3-methoxy-4-propargyloxy)phenyl)-1-oxo-2-propenyl]amino]benzoic acid free form) was accurately weighed out into each glass vial, and then 4 ml of the indicated medium was added. The samples were stirred using a magnetic stirrer at 37° C. After being stirred for 1 h or 24 h, 1 ml of each sample was collected and the final pH recorded. The samples were filtered via centrifugation (12,000 rpm, 5 min). The supernatant was diluted (2×) with HPLC grade solvent and analyzed by HPLC.

HPLC conditions were as follows: Column: Agilent Eclipse Plus C18, 150×4.6 mm, 3.5 μm; Column Temperature: 35° C.; Flow Rate: 1.0 mL/min; Detector Wavelength: 230 nm; Run time: 12 min; Injection Volume: 5 μL; Diluent: Acetone; Mobile Phase A (MPA): 0.1% TFA in $H_2O$; Mobile Phase B (MPB): ACN.

HPLC gradient was as follows:

| Time (min) | MPA (%) | MPB (%) |
|---|---|---|
| 0.00 | 50 | 50 |
| 12.00 | 50 | 50 |

Example 2. Preparation of Salts of (E)-2-[[3-(3-methoxy-4-propargyloxy)phenyl)-1-oxo-2-propenyl]amino]benzoic acid Approximately 100 mg of (E)-2-[[3-(3-methoxy-4-propargyloxy)phenyl)-1-oxo-2-propenyl]amino]benzoic acid ('FT011 free form'; also referred to as 'API' below) was accurately weighed into each glass vial, and then the appropriate amount of solvent, selected from ethyl acetate (EA) and 90% isopropanol (90% IPA), was added to the glass vial, and the mixture was heated to 50° C. A counter-ion source, selected from potassium hydroxide, meglumine, ethanolamine (MEA), tris(hydroxymethyl)aminomethane (Tris base), tert-butylamine (TBA), ammonia, lysine, L-arginine, and choline, was added into each vial, respectively, at a suitable molar ratio (e.g., 5% molar excess). In the case of meglumine, and Tris base, they were accurately weighed and mixed with FT011 free form, and then the solvent was added to that mixture. The respective mixtures were stirred at 50° C. for 1 h, then allowed to cool to room temperature (20-25° C.) and kept being stirred for 24-48 h, after which time the solid precipitate was isolated by centrifugation. If there was no precipitation in the system, the clear solution was evaporated at room temperature by compressed air or nitrogen blowing. The obtained samples were dried under vacuum at 40° C. overnight. Dried samples were analysed by 1H NMR. TGA, DSC and PLM. Detailed procedures of the formation of the salts and their physical properties are summarized in Table 1.

TABLE 1

Experimental details of salt formation.

| Counter-ion | | Molar | | Experimental | |
|---|---|---|---|---|---|
| Base | Amount/ concentration | ratio (API:base) | Solvent (mL) | observations and processes | Form |
| Sodium hydroxide | 59.9 μL (5M in water ) | 1:1.05 | EA (2 mL) | 1. The suspension became clear immediately after adding counter ion. 2. Stirred overnight to obtain suspension and centrifuged to separate the wet solids and dry under reduced pressure at 40° C. overnight. | Low Crystallinity Solid |
| Potassium hydroxide | 59.8 μL (5M in water ) | 1:1.05 | EA (1.5 mL) | 1. The suspension became clear immediately after adding counter ion, but then solids precipitated. 2. Stirred overnight to obtain suspension and centrifuged to separate the wet solids and dry under reduced pressure at 40° C. overnight. | Crystalline Solid |
| Meglumine | 59.0 mg (99%) | 1:1.05 | EA (1 mL) | 1. The sample was presented as suspension. 2. Stirred overnight to obtain suspension and centrifuged to separate the wet solid and dry under reduced pressure at 40° C. overnight. | Crystalline Solid |
| Ethanolamine | 18.1 μL (99%) | 1:1.05 | EA (1.8 mL) | 1. The sample was presented as suspension. 2. Stirred overnight to obtain suspension and centrifuged to separate the wet solids and dry under reduced pressure at 40° C. overnight. | Crystalline Solid |
| Tris base | 36.5 mg (99.5%) | 1:1.05 | EA (1.5 mL) | 1. The sample was presented as suspension. 2. Stirred overnight to obtain suspension and centrifuged to separate the wet solids and dry under reduced pressure at 40° C. overnight. | Crystalline Solid |
| tert-Butylamine (TBA) | 32.0 μL (99%) | 1:1.05 | EA (1 mL) | 1. The sample was presented as suspension. 2. Stirred overnight to obtain suspension and centrifuged to separate the wet solids and dry under reduced pressure at 40° C. overnight. | Crystalline Solid |

TABLE 1-continued

| Experimental details of salt formation. | | | | | |
|---|---|---|---|---|---|
| Counter-ion | | Molar | | Experimental | |
| Base | Amount/ concentration | ratio (API:base) | Solvent (mL) | observations and processes | Form |
| Ammonia | 22.4 μL (25% in water) | 1:1.05 | 90% IPA in water (1.5 mL) | 1. The suspension became clear immediately after adding counter ions. Solids precipitated about 5 minutes later. 2. Stirred overnight to obtain suspension and centrifuged to separate the wet solid and dry under reduced pressure at 40° C. overnight. | Crystalline Solid |
| Lysine | 149.5 μL (2M in water) | 1:1.05 | EA (1 mL) | 1. The suspension became oily after adding counter ions, but then a small amount of solids precipitated about 5 minutes later. 2. Stirred overnight, still as oil, but solids existed, evaporated using compressed air. | Crystalline Solid |
| L-Arginine | 299.2 μL (1M in water) | 1:1.05 | EA (1 mL) | 1. The suspension became oily after adding counter ions. 2. Stirred overnight, still as oil, evaporated using compressed air. 3. Dried under reduced pressure at 40° C. overnight, but still oil. | Oil |
| Choline | 76.5 μL (45% in water) | 1:1.05 | EA (1 mL) | 1. The suspension became oily after adding counter ions. 2. Stirred overnight, still as oil, evaporated using compressed air. 3. Dried under reduced pressure at 40° C. overnight, but still oil. | Oil |

Based on the experimental results, potassium hydroxide, meglumine, ethanolamine (MEA), tris(hydroxymethyl)aminomethane (Tris base), tert-butylamine (TBA), ammonia, and lysine formed crystalline solid salt forms with (E)-2-[[3-(3-methoxy-4-propargyloxy)phenyl)-1-oxo-2-propenyl]amino]benzoic acid. Sodium hydroxide formed a solid salt form of low crystallinity, while L-Arginine and choline did not form solid salt forms and formed an oil instead.

The ethanolamine salt of (E)-2-[[3-(3-methoxy-4-propargyloxy)phenyl)-1-oxo-2-propenyl]amino]benzoic acid was obtained as a crystalline solid, and analysed by X-ray Powder Diffraction (XRPD) and single-crystal X-ray diffraction (SXRD). An X-ray powder diffraction pattern of a sample of crystalline Form I of the ethanolamine salt of (E)-2-[[3-(3-methoxy-4-propargyloxy)phenyl)-1-oxo-2-propenyl]amino]benzoic acid prepared as described above is illustrated in FIG. 1, showing prominent XRP diffraction peaks at degrees 2 theta of 6.6, 11.7, 15.9, 17.7, 23.7, and 26.6° (±0.2 degrees 2θ). "Prominent peaks", as used herein, are a subset of the entire observed peak list. Prominent peaks are selected from observed peaks by identifying preferably non-overlapping peaks with strong intensity. The observed XRP diffraction peaks are listed in Table 2a. Table 2b describes the prominent peaks calculated from the SXRD. The SXRD determination of the monohydrate MEA salt was performed at −103° C. (170 K), whereas the XRPD bulk pattern is measured at room temperature. This temperature difference results in contraction of the crystalline form (when cold), and therefore slight changes in the crystal geometry and resulting peak positions are observed compared to that at room temperature. The overall pattern of the SXRD and XRPD are consistent in terms of diffraction peaks and relative peak heights and so are equivalent, other than the noted temperature effect on precise 2theta values. Table 2c sets out the calculated SXRD peaks for the crystalline Form I of the ethanolamine salt of (E)-2-[[3-(3-methoxy-4-propargyloxy)phenyl)-1-oxo-2-propenyl]amino]benzoic acid. ±numerical value variability is recited due to, as would be understood by a person of skill in the art, standard experimental error in measurement of the relevant parameter. For example, in table 2c 'a' (Å) is recited as 4.7710±(8) which means values from 4.7702 to 4.7718 are explicitly included; 'b' (Å) is recited as 29.645±(4) which means values from 29.641 to 29.649 are explicitly included etc. This approach applies to all such SXRD values recited in the same or a similar manner in this specification.

TABLE 2a

Observed XRP diffraction peaks for crystalline Form I of the ethanolamine salt of (E)-2-[[3-(3-methoxy-4-propargyloxy)phenyl)-1-oxo-2-propenyl]amino]benzoic acid.

| Diffraction angle °2θ (deg) | d space (Å) | Intensity (%) |
|---|---|---|
| 6.64 | 13.298 | 9.5 |
| 10.62 | 8.320 | 4.8 |
| 11.70 | 7.559 | 71.2 |
| 12.14 | 7.285 | 33.6 |
| 13.46 | 6.572 | 4.8 |
| 15.02 | 5.894 | 10.9 |
| 15.94 | 5.555 | 25.6 |
| 17.66 | 5.018 | 40.6 |
| 18.70 | 4.741 | 20.2 |
| 19.18 | 4.624 | 31.1 |
| 20.04 | 4.427 | 18.8 |
| 21.86 | 4.062 | 17.2 |
| 22.68 | 3.918 | 13.4 |
| 23.68 | 3.754 | 67.1 |
| 24.52 | 3.627 | 6.5 |
| 25.68 | 3.466 | 17.8 |
| 26.14 | 3.406 | 32.6 |
| 26.64 | 3.343 | 100.0 |
| 27.50 | 3.241 | 12.4 |
| 27.54 | 3.125 | 13.2 |
| 30.40 | 2.938 | 10.1 |
| 30.76 | 2.905 | 10.7 |
| 31.22 | 2.863 | 9.4 |
| 33.72 | 2.656 | 4.3 |
| 35.42 | 2.532 | 13.4 |
| 37.96 | 2.368 | 8.1 |

TABLE 2b

Calculated SXRD peaks for crystalline Form I of the ethanolamine salt of (E)-2-[[3-(3-methoxy-4-propargyloxy)phenyl)-1-oxo-2-propenyl]amino]benzoic acid.

| Diffraction angle °2θ (deg) | Intensity (%) |
|---|---|
| 6.88 | 58.7 |
| 10.90 | 5.3 |
| 11.94 | 54.5 |
| 12.44 | 58.9 |
| 13.80 | 5.7 |
| 15.34 | 12.3 |
| 16.18 | 17.3 |
| 17.94 | 17.2 |
| 19.00 | 11.6 |
| 19.52 | 21.1 |
| 20.52 | 32.2 |
| 24.20 | 39.5 |
| 26.68 | 46.4 |
| 27.20 | 100.0 |

TABLE 2c

Crystal Data and Data Collection Parameters for crystalline Form 1 of the ethanolamine salt of (E)-2-[[3-(3-methoxy-4-propargyloxy)phenyl)-1-oxo-2-propenyl]amino]benzoic acid. ± values indicate reasonable numerical variability in measurement of the stated value and so values within the variability range are considered to be encompassed.

| Parameter | Value |
|---|---|
| Molecular formula | $C_{20}H_{16}NO_5 \bullet C_2H_8NO$ |
| Formula weight | 412.43 |
| space group | $P2_1/c$ (No. 14) |
| a, Å | 4.7710 ± (8) |
| b, Å | 29.645 ± (4) |
| c, Å | 14.223 ± (2) |
| α, deg | 90 |

TABLE 2c-continued

Crystal Data and Data Collection Parameters for crystalline Form 1 of the ethanolamine salt of (E)-2-[[3-(3-methoxy-4-propargyloxy)phenyl)-1-oxo-2-propenyl]amino]benzoic acid. ± values indicate reasonable numerical variability in measurement of the stated value and so values within the variability range are considered to be encompassed.

| Parameter | Value |
|---|---|
| ß, deg | 90.120 ± (11) |
| γ, deg | 90 |
| V, $Å^3$ | 2011.6 (5) |
| Z | 4 |
| temperature, K | 170 |
| radiation (wavelength, Å) | Cu Kα (1.54178) |

The tert-butylamine salt of (E)-2-[[3-(3-methoxy-4-propargyloxy)phenyl)-1-oxo-2-propenyl]amino]benzoic acid was obtained as a crystalline solid, and analysed by X-ray Powder Diffraction (XRPD). An X-ray powder diffraction pattern of a sample of crystalline Form II of the tert-butylamine salt of (E)-2-[[3-(3-methoxy-4-propargyloxy) phenyl)-1-oxo-2-propenyl]amino]benzoic acid prepared as described above is illustrated in FIG. 8, showing prominent XRP diffraction peaks at degrees 2 theta of 8.36, 13.96, and 17.50 (±0.2 degrees 2θ). The observed XRP diffraction peaks are listed in Table 3.

TABLE 3

Observed XRP diffraction peaks for crystalline Form II of the tert-butylamine salt of (E)-2-[[3-(3-methoxy-4-propargyloxy)phenyl)-1-oxo-2-propenyl]amino]benzoic acid.

| Diffraction angle °2θ (deg) | d space (Å) | Intensity (%) |
|---|---|---|
| 6.62 | 13.346 | 3.2 |
| 8.36 | 10.568 | 100.0 |
| 9.24 | 9.561 | 2.9 |
| 11.62 | 7.610 | 10.1 |
| 13.96 | 6.339 | 26.9 |
| 15.00 | 5.901 | 9.8 |
| 15.48 | 5.720 | 12.7 |
| 17.50 | 5.064 | 30.0 |
| 18.56 | 4.777 | 5.6 |
| 20.08 | 4.418 | 22.1 |
| 21.12 | 4.203 | 22.1 |
| 22.34 | 3.976 | 22.4 |
| 23.34 | 3.808 | 16.6 |
| 23.88 | 3.723 | 18.3 |
| 25.00 | 3.559 | 23.3 |
| 25.60 | 3.477 | 6.8 |
| 26.72 | 3.334 | 17.9 |
| 28.04 | 3.180 | 14.4 |
| 29.64 | 3.012 | 14.1 |
| 34.34 | 2.609 | 3.8 |
| 35.90 | 2.500 | 2.8 |

The meglumine salt of (E)-2-[[3-(3-methoxy-4-propargyloxy)phenyl)-1-oxo-2-propenyl]amino]benzoic acid was obtained as a crystalline solid, and analysed by X-ray Powder Diffraction (XRPD). An X-ray powder diffraction pattern of a sample of crystalline Form III of the meglumine salt of (E)-2-[[3-(3-methoxy-4-propargyloxy)phenyl)-1-oxo-2-propenyl]amino]benzoic acid prepared as described above is illustrated in FIG. 9, showing prominent XRP diffraction peaks at degrees 2 theta of 7.50, 12.86, 15.26, and 23.92 (±0.2 degrees 2θ). The observed XRP diffraction peaks are listed in Table 4.

TABLE 4

Observed XRP diffraction peaks for crystalline Form III of the meglumine salt of (E)-2-[[3-(3-methoxy-4-propargyloxy)phenyl)-1-oxo-2-propenyl]amino]benzoic acid.

| Diffraction angle °2θ (deg) | d space (Å) | Intensity (%) |
|---|---|---|
| 7.50 | 11.779 | 13.2 |
| 8.44 | 10.470 | 5.8 |
| 12.86 | 6.879 | 15.5 |
| 14.20 | 6.232 | 28.1 |
| 14.54 | 6.087 | 36.9 |
| 15.26 | 5.801 | 39.8 |
| 17.18 | 5.157 | 25.7 |
| 17.64 | 5.024 | 8.3 |
| 18.96 | 4.676 | 10.8 |
| 19.56 | 4.535 | 43.8 |
| 20.06 | 4.423 | 7.0 |
| 21.48 | 4.133 | 5.9 |
| 23.38 | 3.969 | 20.4 |
| 23.08 | 3.851 | 18.6 |
| 23.92 | 3.717 | 100.0 |
| 24.84 | 3.581 | 5.0 |
| 26.10 | 3.411 | 8.8 |
| 27.32 | 3.262 | 62.1 |
| 28.96 | 3.081 | 13.0 |
| 29.84 | 2.992 | 7.6 |
| 30.38 | 2.940 | 4.4 |
| 33.66 | 2.661 | 9.9 |
| 35.41 | 2.533 | 4.3 |
| 36.36 | 2.469 | 4.1 |
| 39.72 | 2.267 | 3.6 |

The tris(hydroxymethyl)aminomethane (Tris) salt of (E)-2-[[3-(3-methoxy-4-propargyloxy)phenyl)-1-oxo-2-propenyl]amino]benzoic acid was obtained as a crystalline solid, and analysed by X-ray Powder Diffraction (XRPD). An X-ray powder diffraction pattern of a sample of crystalline Form IV of the tris(hydroxymethyl)aminomethane (Tris) salt of (E)-2-[[3-(3-methoxy-4-propargyloxy)phenyl)-1-oxo-2-propenyl]amino]benzoic acid prepared as described above is illustrated in FIG. 10, showing prominent XRP diffraction peaks at degrees 2 theta of 5.78, 12.18, 15.94, and 17.24 (±0.2 degrees 2θ). The observed XRP diffraction peaks are listed in Table 5.

TABLE 5

Observed XRP diffraction peaks for crystalline Form IV of the tris(hydroxymethyl)aminomethane (Tris) salt of (E)-2-[[3-(3-methoxy-4-propargyloxy)phenyl)-1-oxo-2-propenyl]amino]benzoic acid.

| Diffraction angle °2θ (deg) | d space (Å) | Intensity (%) |
|---|---|---|
| 5.78 | 15.274 | 53.8 |
| 8.22 | 10.746 | 13.9 |
| 11.60 | 7.622 | 11.8 |
| 12.18 | 7.262 | 36.1 |
| 12.98 | 6.818 | 10.8 |
| 13.66 | 6.477 | 18.4 |
| 14.74 | 6.004 | 32.9 |
| 15.94 | 5.556 | 56.3 |
| 17.24 | 5.139 | 59.1 |
| 17.88 | 4.956 | 39.9 |
| 18.98 | 4.671 | 13.9 |
| 20.16 | 4.401 | 51.5 |
| 22.16 | 4.009 | 20.2 |
| 22.76 | 3.903 | 35.3 |
| 23.72 | 3.748 | 10.9 |
| 24.24 | 3.668 | 32.0 |
| 24.80 | 3.587 | 42.4 |
| 25.44 | 3.499 | 16.4 |
| 26.24 | 3.393 | 31.0 |
| 26.76 | 3.329 | 100.0 |

TABLE 5-continued

Observed XRP diffraction peaks for crystalline Form IV of the tris(hydroxymethyl)aminomethane (Tris) salt of (E)-2-[[3-(3-methoxy-4-propargyloxy)phenyl)-1-oxo-2-propenyl]amino]benzoic acid.

| Diffraction angle °2θ (deg) | d space (Å) | Intensity (%) |
|---|---|---|
| 27.46 | 3.245 | 26.5 |
| 28.86 | 3.091 | 12.1 |
| 30.80 | 2.900 | 14.7 |
| 35.80 | 2.506 | 14.6 |
| 39.54 | 2.277 | 8.8 |

The potassium salt of (E)-2-[[3-(3-methoxy-4-propargyloxy)phenyl)-1-oxo-2-propenyl]amino]benzoic acid was obtained as a crystalline solid, and analysed by X-ray Powder Diffraction (XRPD). An X-ray powder diffraction pattern of a sample of crystalline Form V of the potassium salt of (E)-2-[[3-(3-methoxy-4-propargyloxy)phenyl)-1-oxo-2-propenyl]amino]benzoic acid prepared as described above is illustrated in FIG. 11, showing prominent XRP diffraction peaks at degrees 2 theta of 9.84, 10.56, 14.10, and 25.06 (±0.2 degrees 2θ). The observed XRP diffraction peaks are listed in Table 6.

TABLE 6

Observed XRP diffraction peaks for crystalline Form V of the potassium salt of (E)-2-[[3-(3-methoxy-4-propargyloxy)phenyl)-1-oxo-2-propenyl]amino]benzoic acid.

| Diffraction angle °2θ (deg) | d space (Å) | Intensity (%) |
|---|---|---|
| 9.84 | 8.982 | 78.5 |
| 10.56 | 8.370 | 41.4 |
| 13.52 | 6.545 | 7.4 |
| 14.10 | 6.277 | 56.0 |
| 17.32 | 5.115 | 12.7 |
| 19.08 | 4.647 | 7.8 |
| 20.02 | 4.432 | 6.4 |
| 21.84 | 4.066 | 7.2 |
| 23.42 | 3.795 | 14.8 |
| 24.30 | 3.660 | 19.2 |
| 25.06 | 3.550 | 100.0 |
| 26.26 | 3.391 | 49.0 |
| 26.66 | 3.341 | 77.5 |
| 27.22 | 3.274 | 23.1 |
| 28.66 | 3.112 | 13.8 |
| 29.30 | 3.046 | 48.4 |
| 30.64 | 2.916 | 10.4 |
| 32.78 | 2.730 | 17.8 |
| 33.34 | 2.685 | 11.5 |
| 33.88 | 2.644 | 6.7 |
| 35.54 | 2.524 | 11.6 |
| 37.26 | 2.411 | 13.6 |
| 37.68 | 2.386 | 7.7 |

The ammonium salt of (E)-2-[[3-(3-methoxy-4-propargyloxy)phenyl)-1-oxo-2-propenyl]amino]benzoic acid was obtained as a crystalline solid, and analysed by X-ray Powder Diffraction (XRPD). An X-ray powder diffraction pattern of a sample of crystalline Form VI of the ammonium salt of (E)-2-[[3-(3-methoxy-4-propargyloxy)phenyl)-1-oxo-2-propenyl]amino]benzoic acid prepared as described above is illustrated in FIG. 12, showing prominent XRP diffraction peaks at degrees 2 theta of 8.10, 11.66, 17.62, and 26.64 (±0.2 degrees 2θ). The observed XRP diffraction peaks are listed in Table 7.

TABLE 7

Observed XRP diffraction peaks for crystalline Form VI of the ammonium salt of (E)-2-[[3-(3-methoxy-4-propargyloxy)phenyl)-1-oxo-2-propenyl]amino]benzoic acid.

| Diffraction angle °2θ (deg) | d space (Å) | Intensity (%) |
|---|---|---|
| 8.10 | 10.904 | 39.1 |
| 9.12 | 9.687 | 31.2 |
| 11.66 | 7.583 | 95.0 |
| 13.00 | 6.804 | 33.9 |
| 14.98 | 5.909 | 35.3 |
| 17.02 | 5.204 | 13.6 |
| 17.26 | 5.134 | 20.7 |
| 17.62 | 5.029 | 37.4 |
| 20.72 | 2.283 | 5.6 |
| 22.36 | 3.973 | 7.8 |
| 23.68 | 3.754 | 45.4 |
| 24.28 | 3.663 | 13.6 |
| 25.62 | 3.474 | 17.9 |
| 25.98 | 3.427 | 13.2 |
| 26.64 | 3.343 | 100.0 |
| 27.28 | 3.266 | 29.0 |
| 28.34 | 3.146 | 14.8 |
| 29.58 | 3.018 | 4.2 |
| 30.44 | 2.934 | 3.6 |

The lysine salt of (E)-2-[[3-(3-methoxy-4-propargyloxy) phenyl)-1-oxo-2-propenyl]amino]benzoic acid was obtained as a crystalline solid, and analysed by X-ray Powder Diffraction (XRPD). An X-ray powder diffraction pattern of a sample of crystalline Form VII of the lysine salt of (E)-2-[[3-(3-methoxy-4-propargyloxy)phenyl)-1-oxo-2-propenyl] amino]benzoic acid prepared as described above is illustrated in FIG. 13, showing prominent XRP diffraction peaks at degrees 2 theta of 11.76, 14.48, 18.60, and 27.22 (±0.2 degrees 2θ). The observed XRP diffraction peaks are listed in Table 8.

TABLE 8

Observed XRP diffraction peaks for crystalline Form VII of the lysine salt of (E)-2-[[3-(3-methoxy-4-propargyloxy)phenyl)-1-oxo-2-propenyl]amino]benzoic acid.

| Diffraction angle °2θ (deg) | d space (Å) | Intensity (%) |
|---|---|---|
| 6.17 | 14.324 | 7.7 |
| 11.24 | 7.867 | 37.4 |
| 11.76 | 7.520 | 52.8 |
| 12.56 | 7.043 | 23.1 |
| 13.52 | 6.545 | 34.0 |
| 14.48 | 6.112 | 36.9 |
| 15.64 | 5.661 | 18.8 |
| 18.60 | 4.766 | 50.4 |
| 20.06 | 4.423 | 22.5 |
| 20.36 | 4.358 | 30.5 |
| 20.98 | 4.232 | 29.4 |
| 21.22 | 4.183 | 23.3 |
| 21.64 | 4.103 | 34.5 |
| 22.26 | 3.991 | 18.6 |
| 22.98 | 3.867 | 71.4 |
| 23.58 | 3.770 | 45.9 |
| 25.10 | 3.545 | 91.5 |
| 26.60 | 3.348 | 24.9 |
| 27.22 | 3.274 | 100.0 |
| 28.96 | 3.080 | 21.2 |
| 30.30 | 2.948 | 29.4 |
| 31.92 | 2.802 | 16.7 |
| 34.78 | 2.577 | 21.8 |
| 37.14 | 2.419 | 11.1 |

Crystallographic analysis and diffraction data for two (2) free acid forms of (E)-2-[[3-(3-methoxy-4-propargyloxy)

phenyl)-1-oxo-2-propenyl]amino]benzoic acid was carried out. The crystalline monohydrate and anhydrous forms were analysed.

In embodiments, the Form VIII crystalline monohydrate form of (E)-2-[[3-(3-methoxy-4-propargyloxy)phenyl)-1-oxo-2-propenyl]amino]benzoic acid exhibits a single X-ray crystallographic analysis with the parameters shown in table 9.

TABLE 9

Crystal Data and Data Collection Parameters for crystalline monohydrate Form VIII of (E)-2-[[3-(3-methoxy-4-propargyloxy)phenyl)-1-oxo-2-propenyl]amino]benzoic acid. ± values indicate reasonable numerical variability in measurement of the stated value and so values within the variability range are considered to be encompassed

| Parameter | Value |
|---|---|
| Molecular formula | $C_{20}H_{17}NO_5 \bullet H_2O$ |
| Formula weight | 369.35 |
| space group | P-1 (No. 2) |
| a, Å | 15.272 ± (2) |
| b, Å | 16.132 ± (2) |
| c, A | 16.604 ± (3) |
| α, deg | 102.832 ± (4) |
| ß, deg | 111.757 ± (4) |
| γ, deg | 100.021 ± (3) |
| V, Å$^3$ | 3552.7 (9) |
| Z | 8 |
| temperature, K | 200 |
| radiation (wavelength, Å) | Cu Kα (1.54178) |

Figure 24:
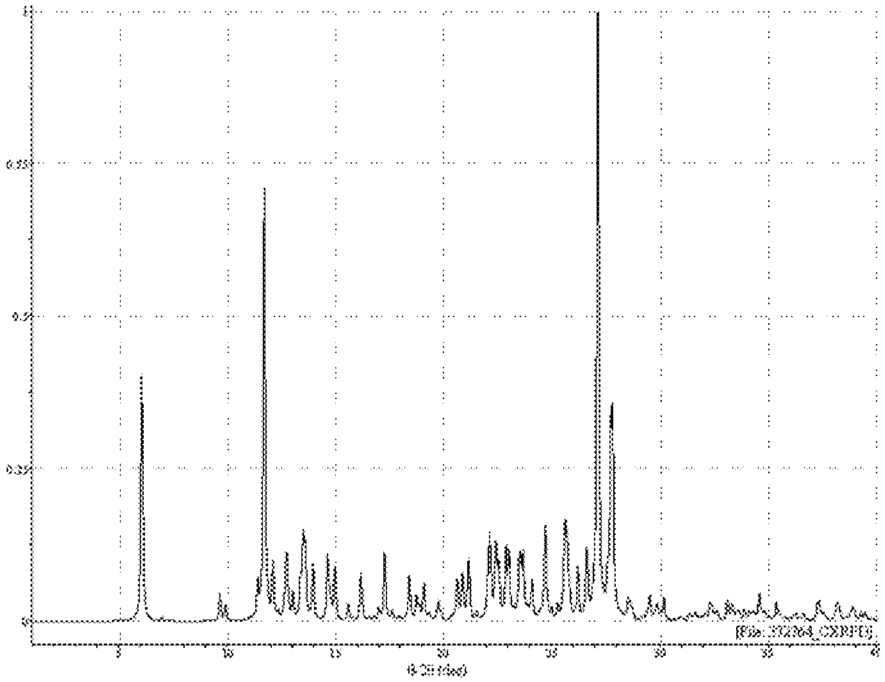
FIG. 24 shows an exemplary X-Ray Powder Diffraction (XRPD) pattern of a sample of crystalline monohydrate Form VIII of (E)-2-[[3-(3-methoxy-4-propargyloxy)phenyl)-1-oxo-2-propenyl]amino]benzoic acid.

Crystalline monohydrate Form VIII of (E)-2-[[3-(3-methoxy-4-propargyloxy)phenyl)-1-oxo-2-propenyl]amino] benzoic acid has an X-ray powder diffraction (XRPD) pattern as depicted in FIG. 24. The XRPD pattern of the crystalline monohydrate Form VIII of (E)-2-[[3-(3-methoxy-4-propargyloxy)phenyl)-1-oxo-2-propenyl]amino] benzoic acid can be seen to include at least one diffraction peak selected from 6.0, 11.7, 12.7, 26.9 and 27.5 degrees 2θ (±0.2 degrees 2θ).

In embodiments, the Form IX crystalline anhydrous form of (E)-2-[[3-(3-methoxy-4-propargyloxy)phenyl)-1-oxo-2-propenyl]amino]benzoic acid exhibits a single X-ray crystallographic analysis with the parameters as set out in table 10.

TABLE 10

Crystal Data and Data Collection Parameters for crystalline anhydrous Form IX of (E)-2-[[3-(3-methoxy-4-propargyloxy)phenyl)-1-oxo-2-propenyl]amino]benzoic acid. ± values indicate reasonable numerical variability in measurement of the stated value and so values within the variability range are considered to be encompassed

| Parameter | Value |
|---|---|
| Molecular formula | $C_{20}H_{17}NO_5$ |
| Formula weight | 351.35 |
| space group | P-1 (No. 2) |
| a, Å | 16.8038 ± (4) |
| b, Å | 16.2407 ± (4) |
| c, A | 12.3443 ± (3) |
| α, deg | 90.0 |
| ß, deg | 92.970 ± (1) |
| γ, deg | 90.0 |

TABLE 10-continued

Crystal Data and Data Collection Parameters for crystalline anhydrous Form IX of (E)-2-[[3-(3-methoxy-4-propargyloxy)phenyl)-1-oxo-2-propenyl]amino]benzoic acid. ± values indicate reasonable numerical variability in measurement of the stated value and so values within the variability range are considered to be encompassed

| Parameter | Value |
|---|---|
| V, Å$^3$ | 3364.30 (14) |
| Z | 8 |
| temperature, K | 100 |
| radiation (wavelength, Å) | Cu Kα (1.54178) |

Figure 25:
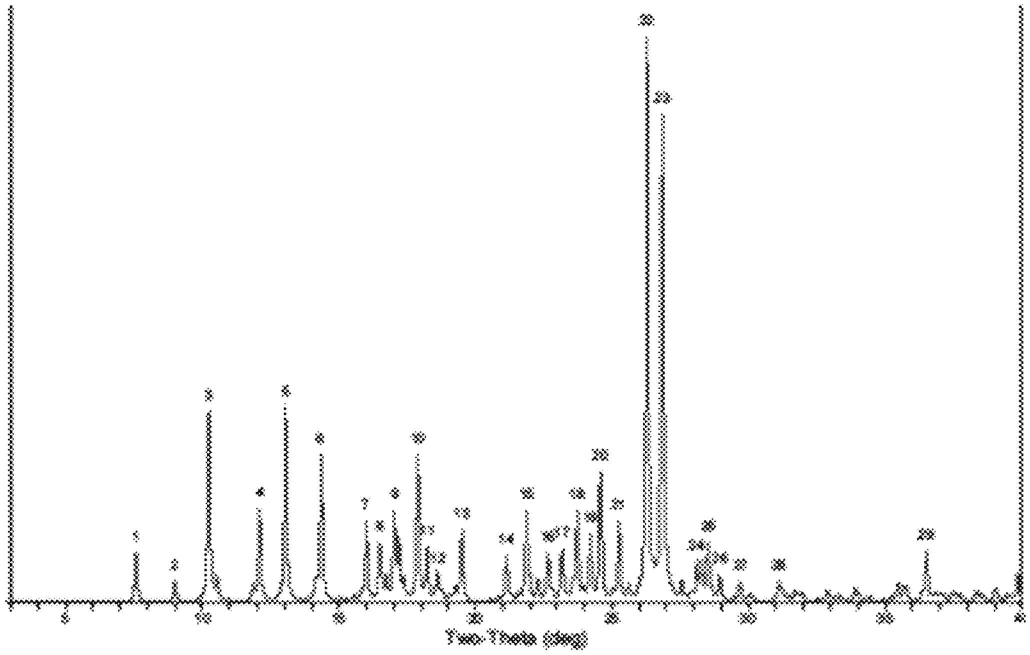
FIG. 25 shows an exemplary X-Ray Powder Diffraction (XRPD) pattern of a sample of crystalline anhydrous Form IX of (E)-2-[[3-(3-methoxy-4-propargyloxy)phenyl)-1-oxo-2-propenyl]amino]benzoic acid.

Crystalline anhydrous Form IX of (E)-2-[[3-(3-methoxy-4-propargyloxy)phenyl)-1-oxo-2-propenyl]amino]benzoic acid has an X-ray powder diffraction (XRPD) pattern as depicted in FIG. 25. The XRPD pattern of the crystalline Form IX of (E)-2-[[3-(3-methoxy-4-propargyloxy)phenyl)-1-oxo-2-propenyl]amino]benzoic acid anhydrous can be seen to include at least one diffraction peak selected from 10.2, 13.0, 14.4, 26.3 and 26.9 degrees 2θ (±0.2 degrees 2θ).

Example 3. Physicochemical Characterisation of Solid Forms of (E)-2-[[3-(3-methoxy-4-propargyloxy)phenyl)-1-oxo-2-propenyl]amino]benzoic acid The chemical and physical properties of the prepared salts of (E)-2-[[3-(3-methoxy-4-propargyloxy)phenyl)-1-oxo-2-propenyl]amino]benzoic acid that were in crystalline solid form were analysed by thermogravimetric analysis (TGA), dynamic vapor sorption (DVS), and differential scanning calorimetry (DSC), and compared to the properties of free form of (E)-2-[[3-(3-methoxy-4-propargyloxy)phenyl)-1-oxo-2-propenyl]amino]benzoic acid. The results are summarised in Table 11.

TABLE 11

Physicochemical properties of solid salts of (E)-2-[[3-(3-methoxy-4-propargyloxy)phenyl)-1-oxo-2-propenyl]amino]benzoic acid (r.t. is room temperature; total weight loss values recited as from r.t. to 350° C. are from that range or to decomposition if lower than 350° C.). DVS values recited at 80% RH as measured during a 0% RH to 95% RH increase.

| Salt | Hygroscopicity by DVS | Weight loss by TGA | DSC (peak) (Enthalpy) |
|---|---|---|---|
| Free form | — | 1.83% from r.t. to 120° C.; 1.83% total weight loss from r.t. to 350° C. | Endo onset 202.80° C., peak 204.35° C. (melting point) (−104.08 J/g) |
| Potassium salt | 6.05% (at 80% RH) | 5.34% from r.t. to 120° C.; 2.02% from 25° C. to 57° C.; 4.40% from 57° C. to 140° C.; 6.42% total weight loss from r.t. to 350° C. | Endo onset 29.71° C., peak 57.18° C. (−64.38 J/g) |
| Meglumine salt | 0.50% (at 80% RH) | 0.07% from r.t. to 120° C.; 0.07% from 0° C. to 120° C.; 0.22% from 120° C. to 170° C.; 0.29% total weight loss from r.t. to 350° C. | Endo onset 116.95° C., peak 119.73° C. (−0.80 J/g) Endo onset 154.19° C., peak 156.54° C. (melting point) (−72.53 J/g) |
| Ethanolamine salt | 0.49% (at 80% RH) | 0.10% from r.t. to 120° C.; 0.10% from 0° C. to 120° C.; 0.10% total weight loss from r.t. to 350° C. | Endo onset 175.76° C., peak 178.46° C. (melting point) (−99.36 J/g) |
| Tris salt | 1.61% (at 80% RH) | 0.65% from r.t. to 120° C.; 0.65% from 0° C. to 120° C.; 0.20% from 120° C. to 150° C.; 0.85% total weight loss from r.t. to 350° C. | Endo onset 153.07° C., peak 155.40° C. (melting point) (−72.26 J/g) |
| tert-Butylamine (TBA) salt | 1.07% (at 80% RH) | 0.94% from r.t. to 120° C.; 0.94% from 25° C. to 120° C.; 6.91% from 120° C. to 190° C.; 7.85% total weight loss from r.t. to 350° C. | Endo onset 174.46° C., peak 180.30° C. (−1.97 J/g) Endo onset 187.13° C., peak 199.02° C. (−77.22 J/g) |

TABLE 11-continued

Physicochemical properties of solid salts of (E)-2-[[3-(3-methoxy-4-propargyloxy)phenyl)-1-oxo-2-propenyl]amino]benzoic acid (r.t. is room temperature; total weight loss values recited as from r.t. to 350° C. are from that range or to decomposition if lower than 350° C.). DVS values recited at 80% RH as measured during a 0% RH to 95% RH increase.

| Salt | Hygroscopicity by DVS | Weight loss by TGA | DSC (peak) (Enthalpy) |
|---|---|---|---|
| Ammonium salt | 6.93% (at 80% RH) | 8.94% from r.t. to 120° C.; 7.07% from 0° C. to 100° C.; 4.48% from 100° C. to 170° C.; 11.55% total weight loss from r.t. to 350° C. | Endo onset 68.05° C., peak 91.15° C. (−82.01 J/g) Endo onset 102.10° C., peak 111.30° C. (−8.65 J/g) Endo onset 124.47° C., peak 139.94° C. (−22.11 J/g) Endo onset 202.73° C., peak 204.37° C. (melting point) (−84.91 J/g) |
| Lysine salt | 8.82% (at 80% RH) | 5.24% from r.t. to 120° C.; 5.24% from 0° C. to 120° C.; 5.24% total weight loss from r.t. to 350° C. | Endo onset 30.00° C., peak 72.68° C. (−24.09 J/g) Endo onset 94.35° C., peak 110.97° C. (−16.28 J/g) Endo onset 135.82° C., peak 148.28° C. (−24.43 J/g) |

The results of Thermogravimetric Analysis (TGA) showed that the meglumine salt, ethanolamine, tris(hydroxymethyl)aminomethane (Tris) and tert-butylamine (TBA) salts of (E)-2-[[3-(3-methoxy-4-propargyloxy)phenyl)-1-oxo-2-propenyl]amino]benzoic acid exhibited the lowest weight loss of 0.07%, 0.10%, 0.65%, and 0.94%, respectively, when heated from about 25° C. to about at 120° C., demonstrating the improved thermal stability of these salts compared to the free form of (E)-2-[[3-(3-methoxy-4-propargyloxy)phenyl)-1-oxo-2-propenyl]amino]benzoic acid and other tested solid salts.

A Thermogravimetric Analysis (TGA) plot of a sample of the ethanolamine salt of (E)-2-[[3-(3-methoxy-4-propargyloxy)phenyl)-1-oxo-2-propenyl]amino]benzoic acid prepared as described above is shown in FIG. 2. The data demonstrates that the salt has thermal stability and showed only about 0.1% weight loss when heated from about 25° C. to about 120° C.

A Thermogravimetric Analysis (TGA) plot of a sample of the tert-butylamine salt of (E)-2-[[3-(3-methoxy-4-propargyloxy)phenyl)-1-oxo-2-propenyl]amino]benzoic acid prepared as described above is shown in FIG. 3. The data demonstrates that the salt is thermally stable and showed only about 0.94% weight loss when heated from about 25° C. to about 120° C.

The results of Dynamic Vapor Sorption (DVS) analysis showed that the meglumine salt, ethanolamine, tris(hydroxymethyl)aminomethane (Tris) and tert-butylamine (TBA) salts of (E)-2-[[3-(3-methoxy-4-propargyloxy)phenyl)-1-oxo-2-propenyl]amino]benzoic acid exhibited the lowest mass increase of 0.50%, 0.49%, 1.61% and 1.07%, respectively, when subjected to an increase in relative humidity from about 0% to about 80% relative humidity, indicating that these salts had low hygroscopicity.

A Dynamic Vapor Sorption (DVS) of a sample of the ethanolamine salt of (E)-2-[[3-(3-methoxy-4-propargyloxy)phenyl)-1-oxo-2-propenyl]amino]benzoic acid prepared as described above is shown in FIG. 4, showing the DVS isotherm plot (top) and DVS change in mass plot (bottom). The data demonstrates that the salt has very low hygroscopicity and showed only about 0.49% mass gain when subjected to an increase in relative humidity from about 0% to about 80% relative humidity.

A Dynamic Vapor Sorption (DVS) of a sample of the tert-butylamine salt of (E)-2-[[3-(3-methoxy-4-propargyloxy)phenyl)-1-oxo-2-propenyl]amino]benzoic acid prepared as described above is shown in FIG. 5, showing the DVS isotherm plot (top) and DVS change in mass plot (bottom). The data demonstrates that the salt has very low hygroscopicity and showed only about 1.07% mass gain when subjected to an increase in relative humidity from about 0% to about 80% relative humidity.

The results of thermal analysis by Differential Scanning calorimetry (DSC) showed that out of the tested crystalline solid salts, the ethanolamine salt and tert-butylamine (TBA) salts of (E)-2-[[3-(3-methoxy-4-propargyloxy)phenyl)-1-oxo-2-propenyl]amino]benzoic acid exhibited a first endothermic event with the highest onset temperature of about 176° C. and about at 175° C., respectively, demonstrating the thermal stability of these salts compared to the other tested salts.

A Differential Scanning calorimetry (DSC) thermogram of a sample of the ethanolamine salt of (E)-2-[[3-(3-methoxy-4-propargyloxy)phenyl)-1-oxo-2-propenyl]amino]benzoic acid prepared as described above is shown in FIG. 6, showing an endothermic event with an onset temperature of about 176° C. and a peak at about 178° C. (melting point). The data demonstrates that the salt has good thermal stability and a relatively high melting point.

A Differential Scanning calorimetry (DSC) thermogram of a sample of the tert-butylamine salt of (E)-2-[[3-(3-methoxy-4-propargyloxy)phenyl)-1-oxo-2-propenyl]amino]benzoic acid prepared as described above is shown in FIG. 7, showing an endothermic event with an onset temperature of about 175° C. and a peak at about 180° C.; and another endothermic event with an onset temperature of about 187° C. and a peak at about 199° C., demonstrating good thermal stability of the salt.

Overall, solid-state characterisation showed that the ethanolamine and Tris salts of (E)-2-[[3-(3-methoxy-4-propargyloxy)phenyl)-1-oxo-2-propenyl]amino]benzoic acid to have most advantageous thermal and moisture-responsive profiles over standard temperature and humidity ranges.

Example 4. Stability of the Ethanolamine Salt of (E)-2-[[3-(3-methoxy-4-propargyloxy)phenyl)-1-oxo-2-propenyl]amino]benzoic acid Long-term, thermal, and moisture stability of the prepared ethanolamine salt of (E)-2-[[3-(3-methoxy-4-propargyloxy) phenyl)-1-oxo-2-propenyl]amino]benzoic acid were determined as follows.

Approximately 10 mg of ethanolamine salt of (E)-2-[[3-(3-methoxy-4-propargyloxy)phenyl)-1-oxo-2-propenyl] amino]benzoic acid was weighed into each vial and stored under the following accelerated storage or long-term storage conditions:

High temperature: 60° C., open vial, 1-2 weeks ('accelerated storage conditions');

High temperature and humidity: 40° C. and 75% relative humidity (RH), open vial, 1-2 weeks ('accelerated storage conditions');

Room temperature: closed vial, 36 days ('long-term storage conditions').

The samples were assayed by HPLC at the start, after 1 week, and after 2 weeks at the indicated accelerated storage conditions, or after 36 days at room temperature storage. For HPLC analysis, the samples were diluted with 10 mL of TFA/DMSO/ACN (0.1/10/90, v/v/v) to ~1 mg/mL and analyzed by HPLC.

Figure 14:
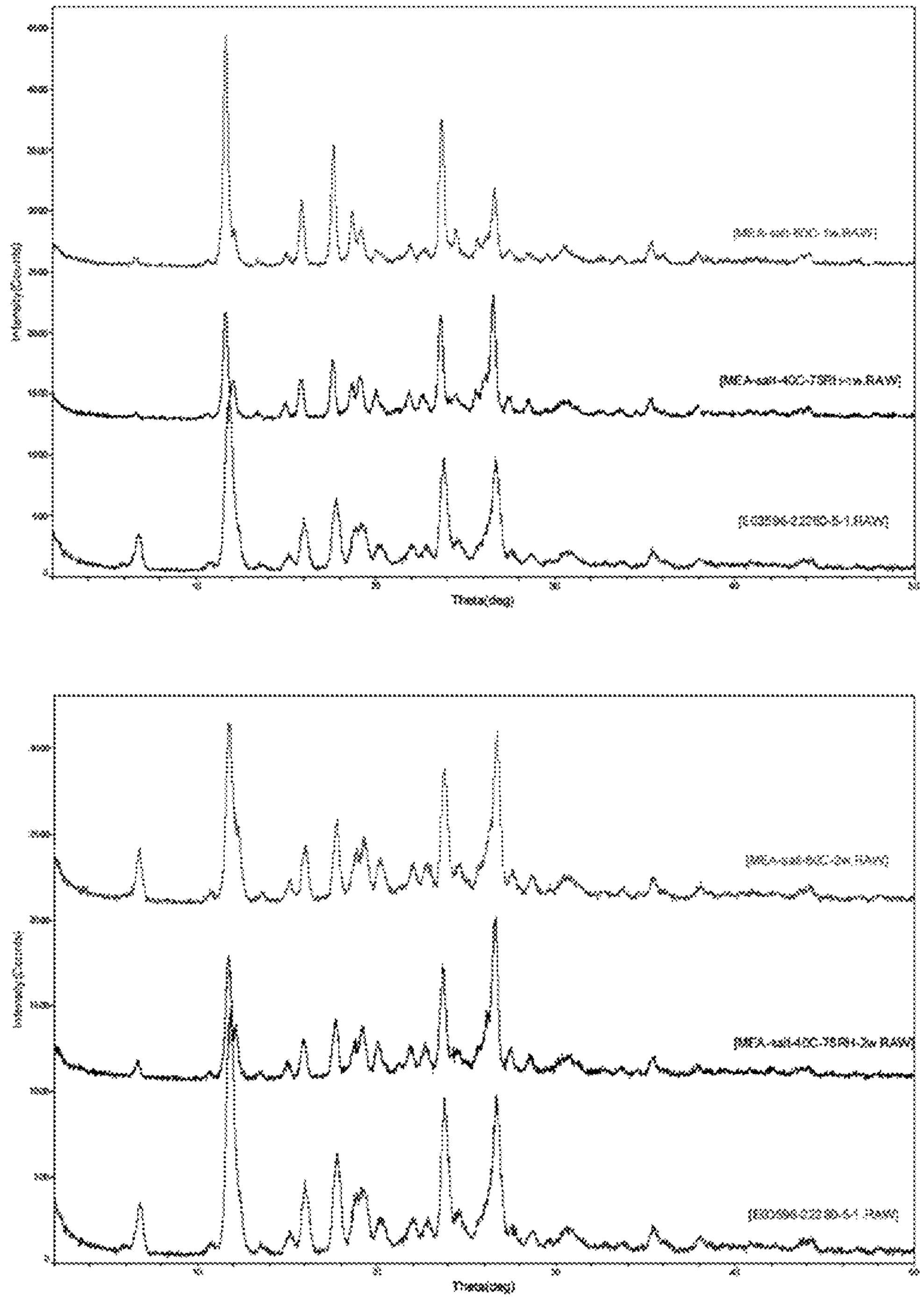
FIG. 14 shows an overlay of XRPD patterns of the ethanolamine salt of (E)-2-[[3-(3-methoxy-4-propargyloxy)phenyl)-1-oxo-2-propenyl]amino]benzoic acid after 1 week (FIG. 14A) or 2 weeks (FIG. 14B) of stability testing under accelerated storage conditions. XRPD patterns of the starting material (bottom pattern), material kept at 40° C. and 75% relative humidity (middle pattern), and material kept at 60° C. (top pattern) are shown.
Figure 15:
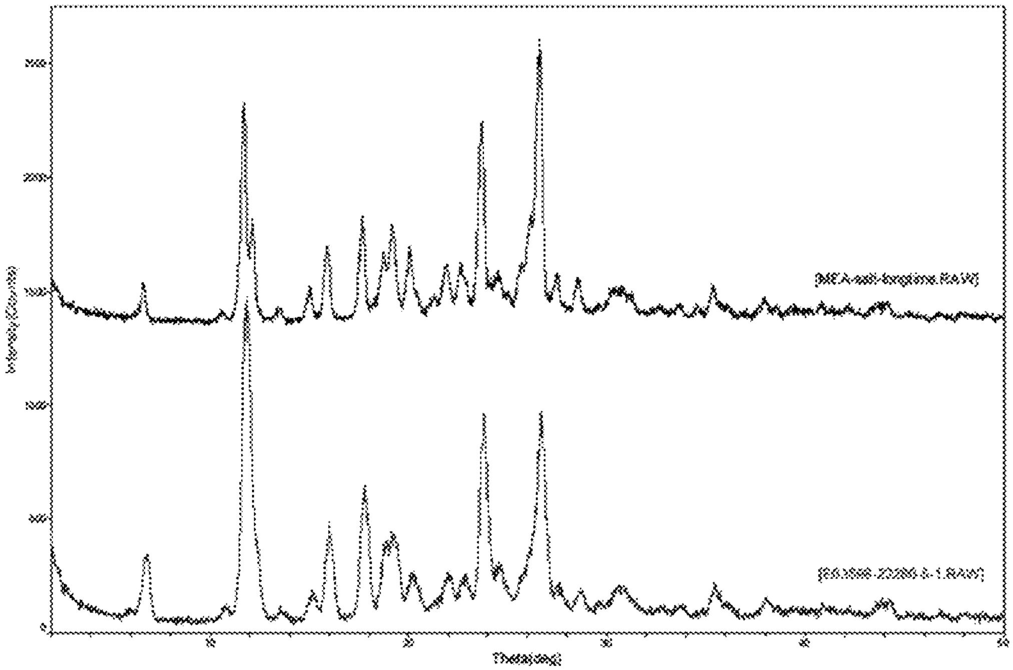
FIG. 15 shows an overlay of XRPD patterns of the ethanolamine salt of (E)-2-[[3-(3-methoxy-4-propargyloxy)phenyl)-1-oxo-2-propenyl]amino]benzoic acid at the start (bottom pattern) and at 36 days of storage at room temperature (top pattern).

The samples were also analyzed by XRPD at initial, 1 week, 2 weeks and 36 day time points. XRPD analysis of the sample of the ethanolamine salt of (E)-2-[[3-(3-methoxy-4-propargyloxy)phenyl)-1-oxo-2-propenyl]amino]benzoic acid at high temperature and/or humidity conditions at initial and 1 week time points is illustrated in FIG. 14A, and the 2 week time point analysis is illustrated in FIG. 14B. FIG. 15 shows the XRPD analysis of the sample of the ethanolamine salt of (E)-2-[[3-(3-methoxy-4-propargyloxy)phenyl)-1-oxo-2-propenyl]amino]benzoic acid at the start or after 36 days of storage at room temperature.

The results are further shown in Table 12.

TABLE 12

Chemical stability of the ethanolamine salt of (E)-2-[[3-(3-methoxy-4-propargyloxy)phenyl)-1-oxo-2-propenyl]amino]benzoic acid

| Storage/Stress condition | | Appearance | Total Impurity % | API (Purity_ % |
|---|---|---|---|---|
| Initial | | White powder | 0.26 | 99.75 |
| 40° C., 75% RH— | 1 week | White powder | 0.27 | 99.73 |
| open vial | 2 weeks | White powder | 0.28 | 99.72 |
| 60° C.— open vial | 1 week | White powder | 0.27 | 99.73 |
| | 2 weeks | White powder | 0.29 | 99.71 |

The results showed no significant changes in impurity content or crystallinity of the ethanolamine salt of (E)-2-[[3-(3-methoxy-4-propargyloxy)phenyl)-1-oxo-2-propenyl] amino]benzoic acid under accelerated storage or long-term storage conditions, demonstrating the chemical and physical stability of the salt.

Example 5. Solubility of Solid Forms of (E)-2-[[3-(3-methoxy-4-propargyloxy)phenyl)-1-oxo-2-propenyl]amino]benzoic acid Solubility of the prepared salts of (E)-2-[[3-(3-methoxy-4-propargyloxy)phenyl)-1-oxo-2-propenyl]amino]benzoic acid that were in crystalline solid form was analysed in pH 1.2, pH 4.5, and pH 6.8 media, as well as in FaSSIF (pH 7.5) and FeSSIF (pH 7.8) media, and compared to the solubility of free form of (E)-2-[[3-(3-methoxy-4-propargyloxy)phenyl)-1-oxo-2-propenyl]amino]benzoic acid. The results are summarised in Table 13. The pH 1.2, pH 4.5, and pH 6.8 media were prepared as standard aqueous buffered solutions following USP <39>.

As used herein, the term "FaSSIF media" means Fasted Stated Simulated Intestinal Fluid media prepared according to the method known in the art. The term "FeSSIF media" means Fed State Simulated Intestinal Fluid prepared according to the method known in the art. The pH of the media was adjusted, if necessary, to the indicated value using, for example, 1N NaOH or 1N HCl.

TABLE 13

Solubility of solid forms of (E)-2-[[3-(3-methoxy-4-propargyloxy)phenyl)-1-oxo-2-propenyl]amino]benzoic acid

| Salt | Medium | 1 h Solubility (mg/ mL) | 24 h Solubility (mg/ mL) | Final pH |
|---|---|---|---|---|
| Free form | pH 1.2 | 0.010 | 0.004 | 1.32 |
| | pH 4.5 | 0.035 | 0.006 | 4.54 |
| | pH 6.8 | 0.394 | 0.051 | 6.86 |
| | FaSSIF | 0.312 | 0.103 | 6.57 |
| | FeSSIF | 0.039 | 0.018 | 5.04 |
| | FaSSIF (pH 7.5) | 1.337 | 1.499 | 6.88 |
| | FeSSIF (pH 7.8) | 0.806 | 0.400 | 6.67 |
| Potassium salt | pH 1.2 | 0.018 | 0.007 | 1.37 |
| | pH 4.5 | 0.030 | 0.006 | 4.71 |
| | pH 6.8 | 0.111 | 0.078 | 7.00 |
| | FaSSIF | 0.218 | 0.211 | 6.93 |
| | FeSSIF | 0.023 | 0.025 | 5.12 |
| | FaSSIF (pH 7.5) | >5.14 | >5.14 | 7.36 |
| | FeSSIF (pH 7.8) | >5.14 | >5.14 | 7.24 |
| Meglumine salt | pH 1.2 | 0.015 | 0.002 | 1.38 |
| | pH 4.5 | 0.016 | 0.002 | 4.72 |
| | pH 6.8 | 0.124 | 0.080 | 7.00 |
| | FaSSIF | 0.217 | 0.257 | 6.91 |
| | FeSSIF | 0.011 | 0.013 | 5.12 |
| | FaSSIF (pH 7.5) | >5.03 | >5.03 | 7.48 |
| | FeSSIF (pH 7.8) | >5.06 | >5.06 | 7.70 |
| Ethanolamine salt | pH 1.2 | 0.008 | 0.003 | 1.72 |
| | pH 4.5 | 0.028 | 0.005 | 4.71 |
| | pH 6.8 | 0.116 | 0.088 | 7.03 |
| | FaSSIF | 0.238 | 0.263 | 6.92 |
| | FeSSIF | 0.012 | 0.025 | 5.11 |
| | FaSSIF (pH 7.5) | >7.99 | >7.99 | 7.39 |
| | FeSSIF (pH 7.8) | >8.02 | >8.02 | 7.25 |
| Tris salt | pH 1.2 | 0.001 | 0.004 | 1.37 |
| | pH 4.5 | <0.001 | 0.002 | 4.72 |
| | pH 6.8 | 0.088 | 0.067 | 6.99 |
| | FaSSIF | 0.267 | 0.257 | 6.91 |
| | FeSSIF | 0.022 | 0.036 | 5.12 |
| | FaSSIF (pH 7.5) | >5.03 | 4.641 | 7.32 |
| | FeSSIF (pH 7.8) | >5.10 | 4.212 | 7.78 |
| tert-Butylamine (TBA) salt | pH 1.2 | <0.001 | 0.004 | 1.36 |
| | pH 4.5 | 0.002 | 0.003 | 4.73 |
| | pH 6.8 | 0.091 | 0.071 | 7.00 |
| | FaSSIF | 0.256 | 0.266 | 6.93 |
| | FeSSIF | 0.018 | 0.047 | 5.12 |

TABLE 13-continued

Solubility of solid forms of (E)-2-[[3-(3-methoxy-4-propargyloxy)phenyl)-1-oxo-2-propenyl]amino]benzoic acid

| Salt | Medium | 1 h Solubility (mg/ mL) | 24 h Solubility (mg/ mL) | Final pH |
|---|---|---|---|---|
| | FaSSIF (pH 7.5) | >2.52 | >2.52 | 7.41 |
| | FeSSIF (pH 7.8) | >3.42 | >3.42 | 7.19 |
| Ammonium salt | pH 1.2 | <0.001 | 0.001 | 1.36 |
| | pH 4.5 | 0.002 | 0.003 | 4.58 |
| | pH 6.8 | 0.077 | 0.048 | 6.94 |
| | FaSSIF | 0.126 | 0.134 | 6.85 |
| | FeSSIF | 0.014 | 0.036 | 5.08 |
| | FaSSIF (pH 7.5) | >2.56 | >2.56 | 7.34 |
| | FeSSIF (pH 7.8) | >2.52 | 1.237 | 7.05 |
| Lysine salt | pH 1.2 | 0.013 | 0.005 | 1.78 |
| | pH 4.5 | 0.002 | 0.016 | 5.09 |
| | pH 6.8 | 0.104 | 0.090 | 7.44 |
| | FaSSIF | 0.151 | 0.172 | 7.27 |
| | FeSSIF | 0.011 | 0.012 | 5.54 |
| | FaSSIF (pH 7.5) | 2.334 | 2.412 | 7.41 |
| | FeSSIF (pH 7.8) | 2.337 | 2.314 | 7.43 |

In a FaSSIF and FeSSIF media, all the prepared crystalline salts demonstrated superior dissolution profiles compared to the solubility of the free form of (E)-2-[[3-(3-methoxy-4-propargyloxy)phenyl)-1-oxo-2-propenyl]amino] benzoic acid.

The results showed that solubility of certain salts (e.g., the ethanolamine, Tris, meglumine, and TBA salt of (E)-2-[[3-(3-methoxy-4-propargyloxy)phenyl)-1-oxo-2-propenyl] amino]benzoic acid) was more than 2.5× higher than solubility of the free form of (E)-2-[[3-(3-methoxy-4-propargyloxy)phenyl)-1-oxo-2-propenyl]amino]benzoic acid.

Example 6. Pharmacokinetic Evaluation of Salts of (E)-2-[[3-(3-methoxy-4-propargyloxy)phenyl)-1-oxo-2-propenyl]amino]benzoic acid in Sprague-Dawley rats The pharmacokinetic properties of the prepared salts of (E)-2-[[3-(3-methoxy-4-propargyloxy)phenyl)-1-oxo-2-propenyl]amino]benzoic acid that were in crystalline solid form were evaluated in Sprague-Dawley rats.

The rats received a single oral dose of 20 mg/kg body weight (b.w.). The doses were prepared as a 2.0 mg/mL suspension in a vehicle of 20 mM $Na_2HPO_4$ buffer containing 5% (v/v) DMSO, 0.4% (v/v) 1M NaOH and 0.4% (v/v) Tween 80 and a dose volume of 10 mL/kg b.w. Blood samples were collected at 0.25, 0.5, 1, 2, 4, 8 and 24 h post dose.

Each compound (free form of (E)-2-[[3-(3-methoxy-4-propargyloxy)phenyl)-1-oxo-2-propenyl]amino]benzoic acid, and potassium (I) salt, meglumine salt, tris(hydroxymethyl)aminomethane ('Tris') salt, tert-butylamine salt, ammonium salt, ethanolamine salt, and lysine salt of (E)-2-[[3-(3-methoxy-4-propargyloxy)phenyl)-1-oxo-2-propenyl] amino]benzoic acid) was tested in a respective group of three rats.

Figure 16:
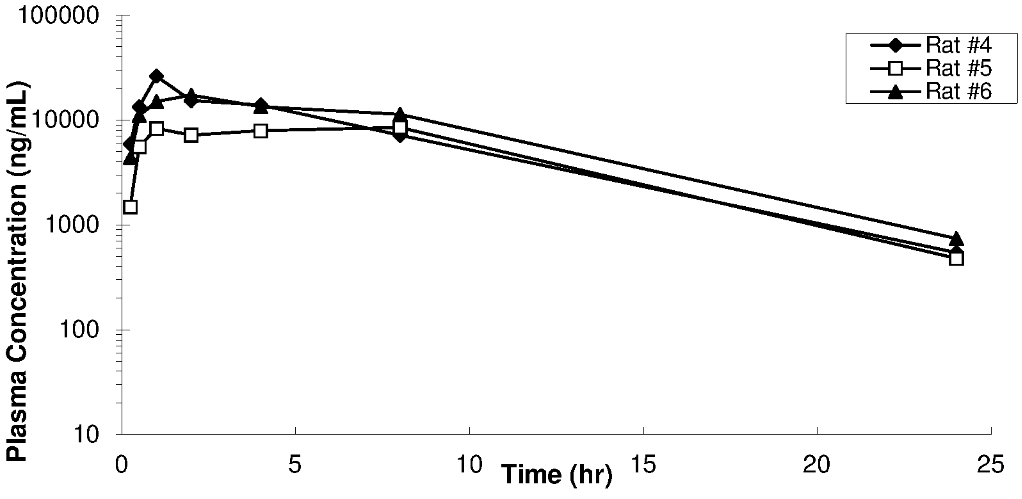
FIG. 16 shows a plot of the plasma concentration over time of the free form of (E)-2-[[3-(3-methoxy-4-propargyloxy)phenyl)-1-oxo-2-propenyl]amino]benzoic acid when orally dosed in Sprague-Dawley rats at 20 mg/kg body weight.
Figure 17:
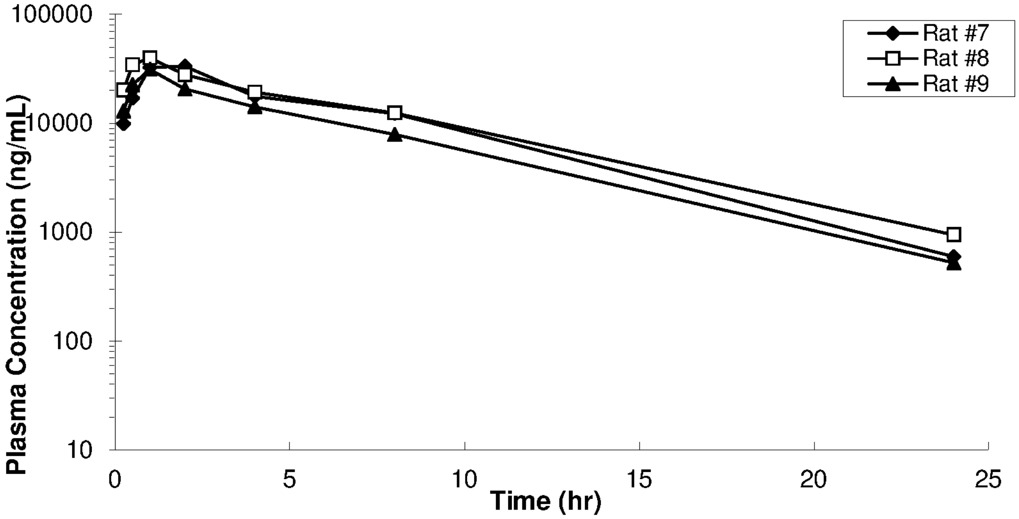
FIG. 17 shows a plot of the plasma concentration over time of the potassium salt of (E)-2-[[3-(3-methoxy-4-propargyloxy)phenyl)-1-oxo-2-propenyl]amino]benzoic acid when orally dosed in Sprague-Dawley rats at 20 mg/kg body weight.
Figure 18:
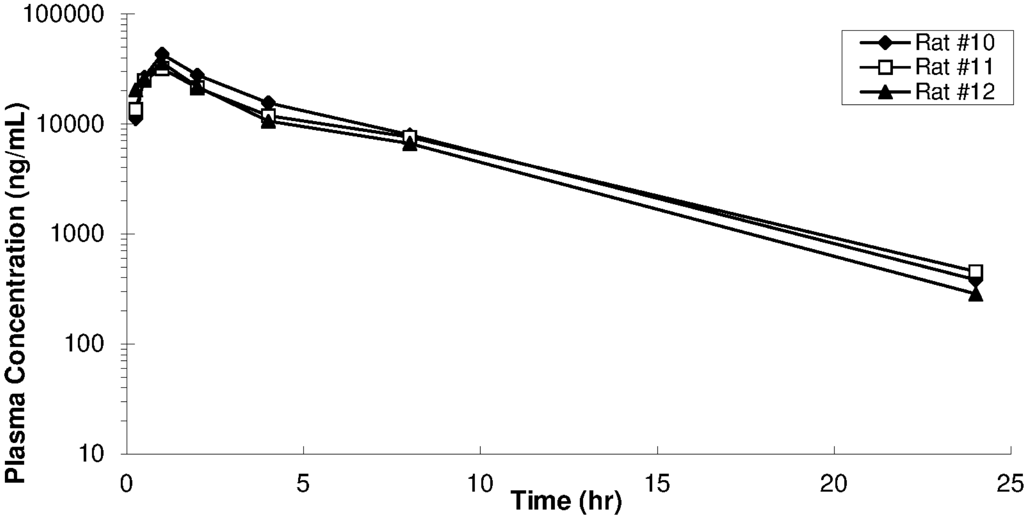
FIG. 18 shows a plot of the plasma concentration over time of the meglumine salt of (E)-2-[[3-(3-methoxy-4-propargyloxy)phenyl)-1-oxo-2-propenyl]amino]benzoic acid when orally dosed in Sprague-Dawley rats at 20 mg/kg body weight.
Figure 19:
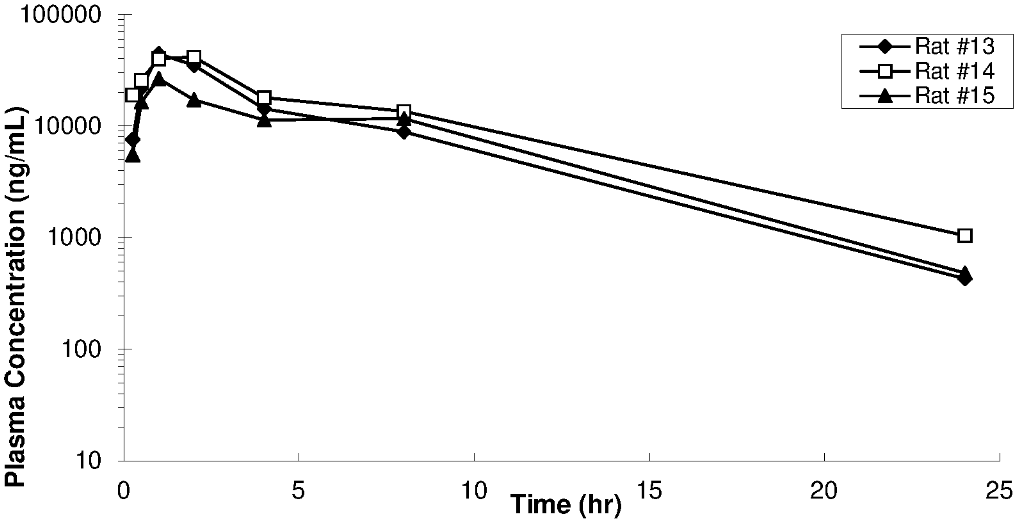
FIG. 19 shows a plot of the plasma concentration over time of the tris(hydroxymethyl)aminomethane (Tris) salt of (E)-2-[[3-(3-methoxy-4-propargyloxy)phenyl)-1-oxo-2-propenyl]amino]benzoic acid when orally dosed in Sprague-Dawley rats at 20 mg/kg body weight.
Figure 20:
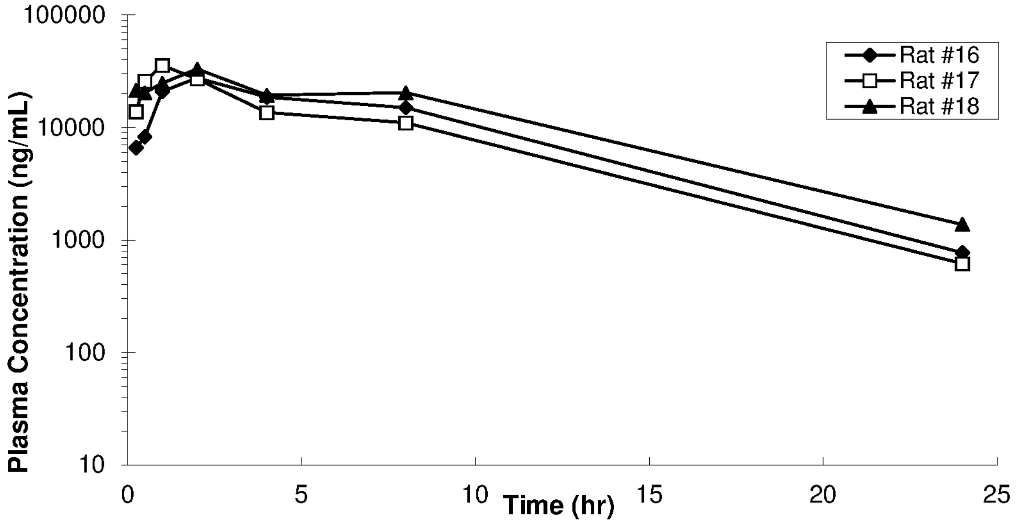
FIG. 20 shows a plot of the plasma concentration over time of the tert-butylamine salt of (E)-2-[[3-(3-methoxy-4-propargyloxy)phenyl)-1-oxo-2-propenyl]amino]benzoic acid when orally dosed in Sprague-Dawley rats at 20 mg/kg body weight.
Figure 21:
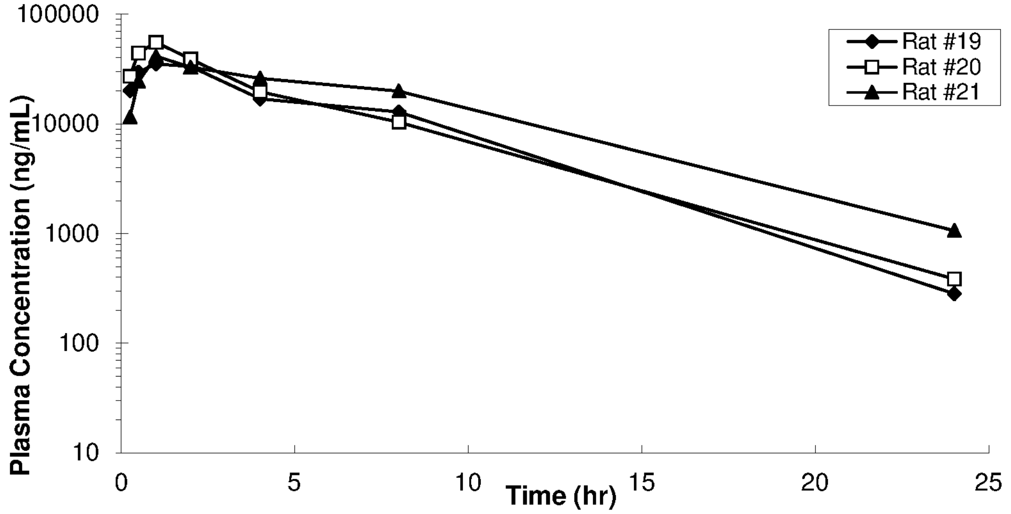
FIG. 21 shows a plot of the plasma concentration over time of the ammonium salt of (E)-2-[[3-(3-methoxy-4-propargyloxy)phenyl)-1-oxo-2-propenyl]amino]benzoic acid when orally dosed in Sprague-Dawley rats at 20 mg/kg body weight.
Figure 22:
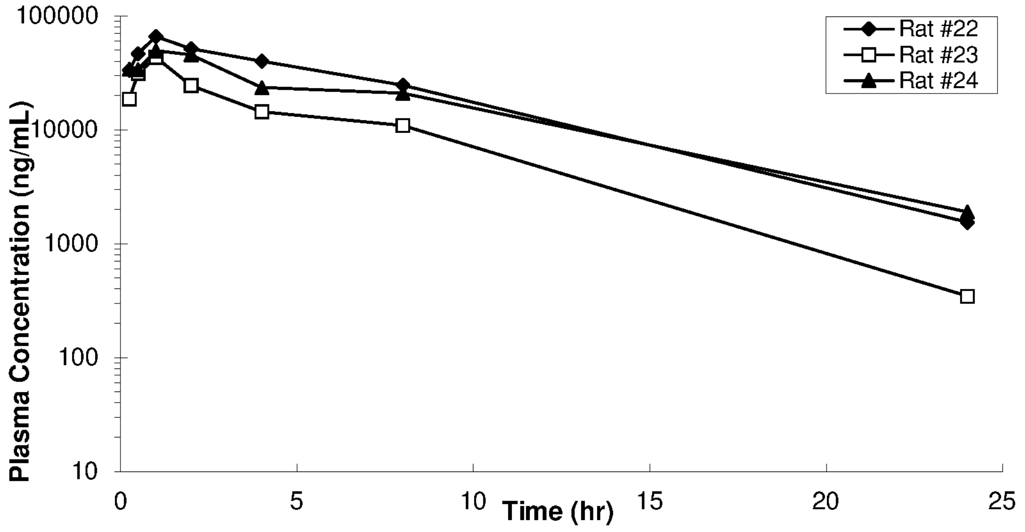
FIG. 22 shows a plot of the plasma concentration over time of the ethanolamine salt of (E)-2-[[3-(3-methoxy-4-propargyloxy)phenyl)-1-oxo-2-propenyl]amino]benzoic acid when orally dosed in Sprague-Dawley rats at 20 mg/kg body weight.
Figure 23:
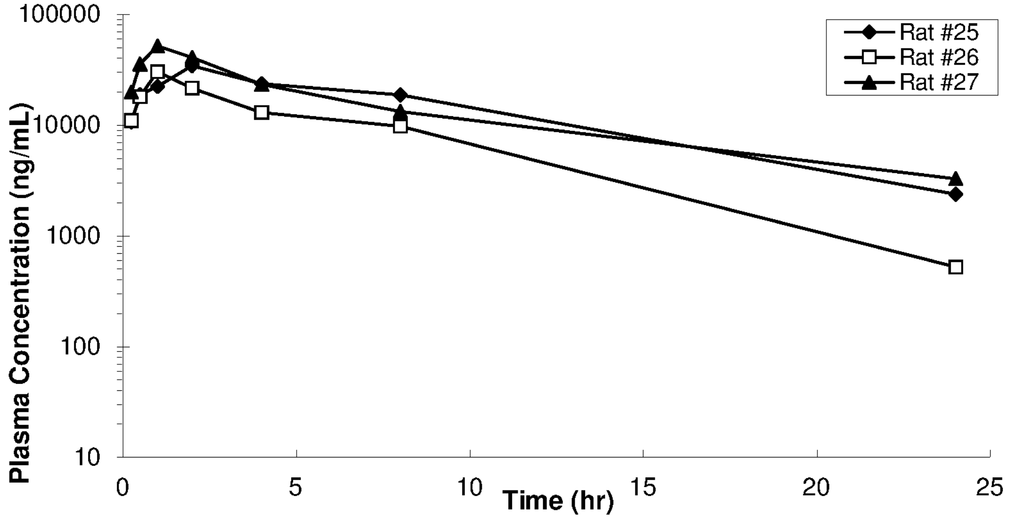
FIG. 23 shows a plot of the plasma concentration over time of the lysine salt of (E)-2-[[3-(3-methoxy-4-propargyloxy)phenyl)-1-oxo-2-propenyl]amino]benzoic acid when orally dosed in Sprague-Dawley rats at 20 mg/kg body weight.

Plots of plasma concentrations of the tested compounds (ng/mL) as a function of time (h) are shown in FIGS. 16 to 23, as follows:

| FIG. | Salt | FW (g/mol) |
|---|---|---|
| FIG. 16 | no salt (free form) | 351.4 |
| FIG. 17 | potassium(I) salt | 389.4 |
| FIG. 18 | meglumine salt | 546.6 |
| FIG. 19 | Tris salt | 472.5 |
| FIG. 20 | tert-butylamine salt | 424.5 |
| FIG. 21 | ammonium salt | 368.4 |
| FIG. 22 | ethanolamine salt | 412.4 |
| FIG. 23 | lysine salt | 497.5 |

Mean plasma concentrations of the tested compounds (ng/ml) as a function of time (h) are shown in Tables 14-21.

TABLE 14

Mean plasma concentration over time of the free form of (E)-2-[[3-(3-methoxy-4-propargyloxy)phenyl)-1-oxo-2-propenyl]amino]benzoic acid.

| Time (h) | Mean concentration (ng/mL) | Standard deviation | Coefficient of variation (CV %) |
|---|---|---|---|
| 0.25 | 3903 | ±2230 | 57.1 |
| 0.5 | 9947 | ±3986 | 40.1 |
| 1 | 16427 | ±9008 | 54.8 |
| 2 | 13217 | ±5339 | 40.4 |
| 4 | 11693 | ±3316 | 28.4 |
| 8 | 8990 | ±2105 | 23.4 |
| 24 | 586 | ±137 | 23.4 |

TABLE 15

Mean plasma concentration over time of the potassium salt of (E)-2-[[3-(3-methoxy-4-propargyloxy)phenyl)-1-oxo-2-propenyl]amino]benzoic acid.

| Time (h) | Mean concentration (ng/ml) | Standard deviation | Coefficient of variation (CV %) |
|---|---|---|---|
| 0.25 | 14327 | ±5306 | 37.0 |
| 0.5 | 24600 | ±8839 | 35.9 |
| 1 | 34467 | ±4579 | 13.3 |
| 2 | 27200 | ±6421 | 23.6 |
| 4 | 17000 | ±2651 | 15.6 |
| 8 | 10850 | ±2599 | 23.9 |
| 24 | 687 | ±225 | 32.8 |

TABLE 16

Mean plasma concentration over time of the meglumine salt of (E)-2-[[3-(3-methoxy-4-propargyloxy)phenyl)-1-oxo-2-propenyl]amino]benzoic acid.

| Time (h) | Mean concentration (ng/ml) | Standard deviation | Coefficient of variation (CV %) |
|---|---|---|---|
| 0.25 | 15000 | ±4732 | 31.5 |
| 0.5 | 25600 | ±900 | 3.52 |
| 1 | 36833 | ±5685 | 15.4 |
| 2 | 23467 | ±3585 | 15.3 |
| 4 | 12633 | ±2554 | 20.2 |
| 8 | 7373 | ±670 | 9.08 |
| 24 | 373 | ±86 | 23.0 |

TABLE 17

Mean plasma concentration over time of the Tris salt of (E)-2-[[3-(3-methoxy-4-propargyloxy)phenyl)-1-oxo-2-propenyl]amino]benzoic acid.

| Time (h) | Mean concentration (ng/mL) | Standard deviation | Coefficient of variation (CV %) |
|---|---|---|---|
| 0.25 | 10663 | ±7206 | 67.6 |
| 0.5 | 21300 | ±4729 | 22.2 |
| 1 | 36833 | ±9311 | 25.3 |

TABLE 17-continued

Mean plasma concentration over time of the Tris salt of (E)-2-[[3-(3-methoxy-4-propargyloxy)phenyl)-1-oxo-2-propenyl]amino]benzoic acid.

| Time (h) | Mean concentration (ng/mL) | Standard deviation | Coefficient of variation (CV %) |
|---|---|---|---|
| 2 | 31067 | ±12551 | 40.4 |
| 4 | 14467 | ±3308 | 22.9 |
| 8 | 11317 | ±2338 | 20.7 |
| 24 | 650 | ±339 | 52.2 |

TABLE 18

Mean plasma concentration over time of the tert-butylamine (TBA) salt of (E)-2-[[3-(3-methoxy-4-propargyloxy)phenyl)-1-oxo-2-propenyl]amino]benzoic acid.

| Time (h) | Mean concentration (ng/mL) | Standard deviation | Coefficient of variation (CV %) |
|---|---|---|---|
| 0.25 | 13907 | ±7341 | 52.8 |
| 0.5 | 18080 | ±8939 | 49.4 |
| 1 | 26967 | ±7630 | 28.3 |
| 2 | 29167 | ±3329 | 11.4 |
| 4 | 17133 | ±3166 | 18.5 |
| 8 | 15433 | ±4665 | 30.2 |
| 24 | 918 | ±399 | 43.5 |

TABLE 19

Mean plasma concentration over time of the ammonium salt of (E)-2-[[3-(3-methoxy-4-propargyloxy)phenyl)-1-oxo-2-propenyl]amino]benzoic acid.

| Time (h) | Mean concentration (ng/ml) | Standard deviation | Coefficient of variation (CV %) |
|---|---|---|---|
| 0.25 | 19567 | ±7859 | 40.2 |
| 0.5 | 32700 | ±10306 | 31.5 |
| 1 | 44033 | ±10403 | 23.6 |
| 2 | 35033 | ±3281 | 9.36 |
| 4 | 20833 | ±4606 | 22.1 |
| 8 | 14400 | ±4924 | 34.2 |
| 24 | 575 | ±423 | 73.5 |

TABLE 20

Mean plasma concentration over time of the ethanolamine salt of (E)-2-[3-(3-methoxy-4-propargyloxy)phenyl)-1-oxo-2-propenyl]amino]benzoic acid.

| Time (h) | Mean concentration (ng/mL) | Standard deviation | Coefficient of variation (CV %) |
|---|---|---|---|
| 0.25 | 28600 | ±8665 | 30.3 |
| 0.5 | 37133 | ±8208 | 22.1 |
| 1 | 52733 | ±11636 | 22.1 |
| 2 | 40300 | ±14082 | 34.9 |
| 4 | 25900 | ±12933 | 49.9 |
| 8 | 18767 | ±7073 | 37.7 |
| 24 | 1262 | ±814 | 64.5 |

TABLE 21

Mean plasma concentration over time of the lysine salt of (E)-2-[[3-(3-methoxy-4-propargyloxy)phenyl)-1-oxo-2-propenyl]amino]benzoic acid.

| Time (h) | Mean concentration (ng/ml) | Standard deviation | Coefficient of variation (CV %) |
|---|---|---|---|
| 0.25 | 13800 | ±5200 | 37.7 |
| 0.5 | 24067 | ±9823 | 40.8 |
| 1 | 34733 | ±15242 | 43.9 |
| 2 | 32167 | ±9809 | 30.5 |
| 4 | 19900 | ±5977 | 30.0 |
| 8 | 13883 | ±4514 | 32.5 |
| 24 | 2054 | ±1401 | 68.2 |

The obtained data demonstrated that the ethanolamine and lysine salts of (E)-2-[[3-(3-methoxy-4-propargyloxy)phenyl)-1-oxo-2-propenyl]amino]benzoic acid had the highest plasma concentrations at 24 h post dose, indicating more extended release pharmacokinetic profiles of the salts compared to the other tested compounds.

Pharmacokinetic analysis was performed on the average plasma concentration for each time point. Mean plasma pharmacokinetic parameters are summarised in Table 22.

TABLE 22

Mean plasma PK parameters obtained in oral pharmacokinetic study in rats.

| Salt | $t_{1/2}$ (h) | $t_{max}$ (h) | $C_{max}$ (ng/ml) | $AUC_{last}$ (h * ng/ml) | $AUC_{Inf}$ (h * ng/ml) | $AUC_{Extr}$ (%) | F (%) |
|---|---|---|---|---|---|---|---|
| no salt (free form) | 4.23 | 3.67 | 17263 | 166522 | 170145 | 2.10 | 35 |
| potassium(I) | 4.21 | 1.33 | 34733 | 244450 | 248674 | 1.68 | 51 |
| meglumine | 3.87 | 1.00 | 36833 | 190795 | 192897 | 1.09 | 39 |
| Tris | 4.02 | 1.33 | 37367 | 246642 | 250596 | 1.49 | 51 |
| tert-butylamine | 4.18 | 1.67 | 32000 | 287306 | 292817 | 1.83 | 59 |
| ammonium | 3.62 | 1.00 | 44033 | 313832 | 317034 | 0.932 | 64 |
| ethanolamine | 4.32 | 1.00 | 52733 | 396535 | 405006 | 1.92 | 82 |
| lysine | 5.76 | 1.33 | 38733 | 301740 | 320917 | 5.30 | 65 |

$C_{max}$ is the maximum blood plasma concentration.

$t_{1/2}$ is the amount of time for the blood plasma level to decrease to half of the $C_{max}$ level beginning at administration.

$t_{max}$ is the time to maximum blood plasma concentration from administration.

$AUC_{Inf}$ is the extrapolated area under the curve.

F = fraction absorbed (bioavailability); F was based on the calculation of $AUC_{Inf}$.

The obtained data demonstrated that the ethanolamine and ammonium salts of (E)-2-[[3-(3-methoxy-4-propargyloxy)phenyl)-1-oxo-2-propenyl]amino]benzoic acid achieved the highest maximum plasma concentration ($C_{max}$). The results further showed that the ethanolamine, lysine, ammonium and tert-butylamine salts of (E)-2-[[3-(3-methoxy-4-propargyloxy)phenyl)-1-oxo-2-propenyl]amino]benzoic acid had the highest oral bioavailability of the tested compounds. The ethanolamine salt of (E)-2-[[3-(3-methoxy-4-propargyloxy)phenyl)-1-oxo-2-propenyl]amino]benzoic acid was observed to have an unexpectedly high oral bioavailability of 82%, demonstrating superior pharmacokinetic properties of this salt. The results demonstrated that oral bioavailability of the ethanolamine salt of (E)-2-[[3-(3-methoxy-4-propargyloxy)phenyl)-1-oxo-2-propenyl]amino]benzoic acid (82%) is about 2.3× greater than oral bioavailability of the free form of (E)-2-[[3-(3-methoxy-4-propargyloxy)phenyl)-1-oxo-2-propenyl]amino]benzoic acid (35%).

The invention claimed is:

1. A crystalline form of a pharmaceutically acceptable salt of the compound of Formula (I):

Formula (I)

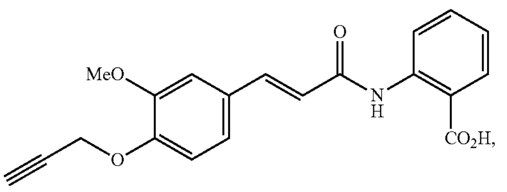

wherein the crystalline form has a water sorption of from 0.49% to 8.82% at 25° C. and 80% relative humidity as determined by dynamic vapor sorption.

2. The crystalline form according to claim 1, wherein the pharmaceutically acceptable salt is selected from the group consisting of: a meglumine salt, an ethanolamine salt, a tris(hydroxymethyl)aminomethane salt, and a tert-butylamine salt.

3. A pharmaceutical composition comprising the crystalline form according to claim 1 and at least one pharmaceutically acceptable excipient.

4. A solid form of a pharmaceutically acceptable salt of the compound of Formula (I):

Formula (I)

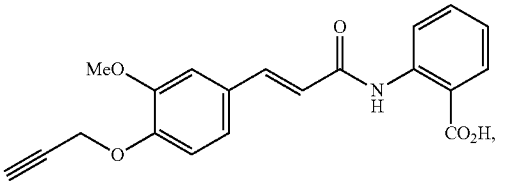

having a bioavailability of at least 1.4× compared to a bioavailability of a free acid form of the compound of Formula (I).

5. The solid form according to claim 4, having a bioavailability of from 1.4× to 3.0× compared to a bioavailability of a free acid form of the compound of Formula (I).

6. The solid form according to claim 4, wherein the solid form is a crystalline form.

7. The crystalline form according to claim 6, wherein the crystalline form is an ethanolamine salt of the compound of Formula (I).

8. A pharmaceutical composition comprising the solid form according to claim 4 and at least one pharmaceutically acceptable excipient.

9. A crystalline form of a pharmaceutically acceptable salt of the compound of Formula (I):

Formula (I)

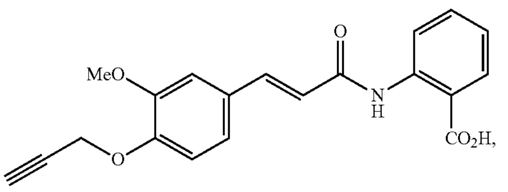

wherein the crystalline form exhibits an X-ray powder diffraction pattern having (i) at least two peaks selected from 8.4±0.2, 14.0±0.2, and 17.5±0.2 degrees 2θ, (ii) at least two peaks selected from 7.5±0.2, 12.9±0.2, 15.3±0.2, and 23.9±0.2 degrees 2θ, or (iii) at least two peaks selected from 5.8±0.2, 12.2±0.2, 15.9±0.2, and 17.2±0.2 degrees 2θ.

10. The crystalline form according to claim 1, wherein the crystalline form has a water sorption of from 0.49% to 6.93% at 25° C. and 80% relative humidity as determined by dynamic vapor sorption.

11. The crystalline form according to claim 1, wherein the crystalline form has a water sorption of from 0.49% to 6.05% at 25° C. and 80% relative humidity as determined by dynamic vapor sorption.

12. The crystalline form according to claim 1, wherein the crystalline form has a water sorption of from 0.49% to 1.61% at 25° C. and 80% relative humidity as determined by dynamic vapor sorption.

13. The crystalline form according to claim 1, wherein the crystalline form has a water sorption of from 0.49% to 1.07% at 25° C. and 80% relative humidity as determined by dynamic vapor sorption.

14. The crystalline form according to claim 1, wherein the crystalline form has a water sorption of 8.8%, 6.9%, 6.1%, 1.6%, 1.1%, or 0.50% at 25° C. and 80% relative humidity as determined by dynamic vapor sorption.

15. The solid form according to claim 4, having a bioavailability of at least 2.3× compared to a bioavailability of a free form of the compound of Formula (I).

16. A pharmaceutical composition comprising a pharmaceutically acceptable salt of the compound of Formula (I):

Formula (I)

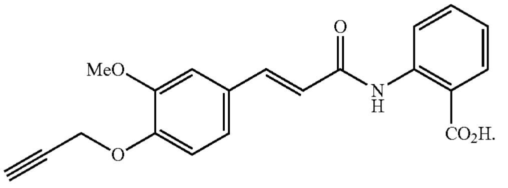

and at least one pharmaceutically acceptable excipient, wherein at least 80% of the pharmaceutically acceptable salt of the compound of Formula (I) is the crystalline form of according to claim 1.

17. A pharmaceutical composition comprising a pharmaceutically acceptable salt of the compound of Formula (I):

Formula (I)

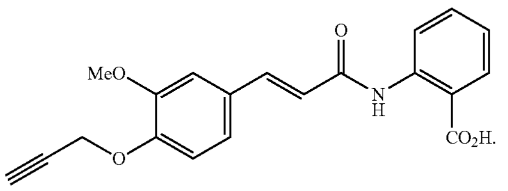

and at least one pharmaceutically acceptable excipient, wherein at least 90% of the pharmaceutically acceptable salt of the compound of Formula (I) is the crystalline form of according to claim 1.

18. A pharmaceutical composition comprising a pharmaceutically acceptable salt of the compound of Formula (I):

Formula (I)

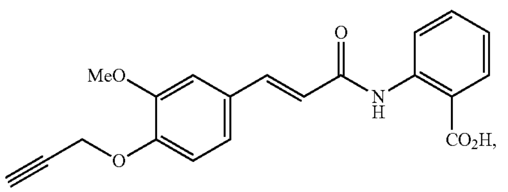

and at least one pharmaceutically acceptable excipient, wherein at least 95% of the pharmaceutically acceptable salt of the compound of Formula (I) is the crystalline form of according to claim 1.

19. The pharmaceutical composition according to claim 16, wherein the crystalline form has a bioavailability of at least 1.4× compared to a bioavailability of the free form of the compound of Formula (I).

20. The pharmaceutical composition according to claim 16, wherein the crystalline form has a bioavailability of from 1.4× to 3.0× compared to a bioavailability of the free form of the compound of Formula (I).

21. The pharmaceutical composition according to claim 16, wherein the crystalline form has a bioavailability of at least 2.3× compared to a bioavailability of the free form of the compound of Formula (I).

22. A crystalline form of a pharmaceutically acceptable salt of the compound of Formula (I):

Formula (I)

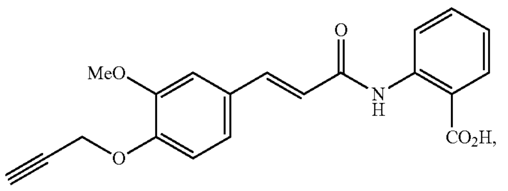

wherein the crystalline form has at least one of (i) an endothermic onset of from 29° C. to 187° C. as measured by differential scanning calorimetry and (ii) a melting point of from 57° C. to 199° C. as measured by differential scanning calorimetry.

23. The crystalline form according to claim 22, wherein the crystalline form has at least one of (i) an endothermic onset of from 116° C. to 187° C. as measured by differential scanning calorimetry and (ii) a melting point of from 155° C. to 199° C. as measured by differential scanning calorimetry.

24. A crystalline form of a pharmaceutically acceptable salt of the compound of Formula (I):

Formula (I)

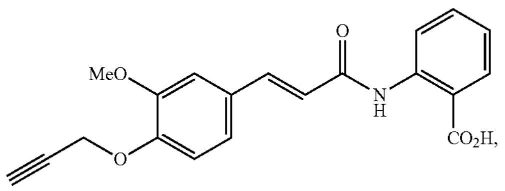

wherein the crystalline form exhibits an X-ray powder diffraction pattern having (i) at least two peaks selected from 9.8±0.2, 10.6±0.2, 14.1±0.2, and 25.1±0.2 degrees 2θ (±0.2 degrees 2θ), (ii) at least two peaks selected from 8.1±0.2, 11.7±0.2, 17.6±0.2, and 26.6±0.2 degrees 2θ, or iii) at least two peaks selected from 11.8±0.2, 14.5±0.2, 18.6±0.2, and 27.2±0.2 degrees 2θ.

25. A method of treating, preventing, or ameliorating a fibrotic, inflammatory, or proliferative disease or condition in a subject, comprising administering to the subject a therapeutically effective amount of the crystalline form of claim 9.

26. The method of claim 25, wherein the fibrotic, inflammatory, or proliferative disease or condition is a kidney disease or is scleroderma.

27. A method of treating, preventing, or ameliorating a fibrotic, inflammatory, or proliferative disease or condition in a subject, comprising administering to the subject a therapeutically effective amount of the crystalline form of claim 24.

28. The method of claim 27, wherein the fibrotic, inflammatory, or proliferative disease or condition is a kidney disease or is scleroderma.

29. A method of making a pharmaceutical composition, the method comprising combining a pharmaceutically acceptable salt of the compound of Formula (I):

Formula (I)

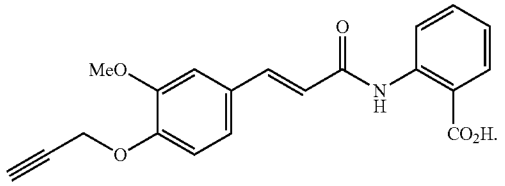

and at least one pharmaceutically acceptable excipient, wherein at least 80% of the pharmaceutically acceptable salt of the compound of Formula (I) is the crystalline form of according to claim 1.

30. A method of making the crystalline form of claim 1, the method comprising:

contacting the compound of Formula (I) with a source of counter-ions in a solvent at a first temperature; and crystallizing the crystalline form of the pharmaceutically acceptable salt of the compound of Formula (I) at a second temperature.

* * * * *